(12) United States Patent
Zador et al.

(10) Patent No.: US 12,031,127 B2
(45) Date of Patent: Jul. 9, 2024

(54) MULTIPLEXED ANALYSIS OF NEURON PROJECTIONS BY SEQUENCING

(71) Applicant: Cold Spring Harbor Laboratory, Cold Spring Harbor, NY (US)

(72) Inventors: Anthony Zador, Cold Spring Harbor, NY (US); Justus Kebschull, Cold Spring Harbor, NY (US)

(73) Assignee: COLD SPRING HARBOR LABORATORY, Cold Spring Harbor, NY (US)

( * ) Notice: Subject to any disclaimer, the term of this patent is extended or adjusted under 35 U.S.C. 154(b) by 735 days.

(21) Appl. No.: 16/091,913

(22) PCT Filed: Apr. 5, 2017

(86) PCT No.: PCT/US2017/026055
§ 371 (c)(1),
(2) Date: Oct. 5, 2018

(87) PCT Pub. No.: WO2017/176829
PCT Pub. Date: Oct. 12, 2017

(65) Prior Publication Data
US 2019/0071666 A1    Mar. 7, 2019

Related U.S. Application Data

(60) Provisional application No. 62/320,386, filed on Apr. 8, 2016.

(51) Int. Cl.
| | |
|---|---|
| *C12N 15/10* | (2006.01) |
| *C07K 14/18* | (2006.01) |
| *C12N 5/0793* | (2010.01) |
| *C12N 15/09* | (2006.01) |
| *C12Q 1/6806* | (2018.01) |
| *C40B 70/00* | (2006.01) |

(52) U.S. Cl.
CPC ...... *C12N 15/1065* (2013.01); *C07K 14/1808* (2013.01); *C12N 5/0619* (2013.01); *C12N 15/09* (2013.01); *C12N 15/10* (2013.01); *C12N 15/102* (2013.01); *C12Q 1/6806* (2013.01); *C40B 70/00* (2013.01); *C12N 2770/36143* (2013.01)

(58) Field of Classification Search
CPC .................................. A61K 38/16; C12Q 1/02
See application file for complete search history.

(56) References Cited

U.S. PATENT DOCUMENTS

| | | |
|---|---|---|
| 2010/0304364 A1 | 12/2010 | Wickersham et al. |
| 2013/0058871 A1* | 3/2013 | Kim ........................ A61P 25/30 424/9.6 |

FOREIGN PATENT DOCUMENTS

| | | |
|---|---|---|
| EP | 1281718 A2 | 2/2003 |
| EP | 1281718 A3 | 1/2005 |
| WO | WO 2016-040594 A1 | 3/2016 |

OTHER PUBLICATIONS

Kim et al., mGRASP Enables Mapping Mammalian Synaptic Connectivity With Light Microscopy, Nature Methods, epub 2011, 9(1), 96-104. (Year: 2011).*
Kim et al., mGRASP Enables Mapping Mammalian Synaptic Connectivity With Light Microscopy, Supplementary Information, Nature Methods, epub 2011, 9(1), 96-104. (Year: 2011).*
Moon et al., Imaging Single mRNA Dynamics in Live Neurons and Brains, Methods in Enzymology, 2016, 572, 51-64. (Year: 2016).*
Marblestone et al., Rosetta Brains: A Strategy for Molecularly-Annotated Connectomics, arXiv: Neurons and Cognition, 2014, 1-18. (Year: 2014).*
Peikon et al., In vivo Generation of DNA Sequence Diversity For Cellular Barcoding, Nucleic Acids Research, 2014, 42(16), 1-10. (Year: 2014).*
Zador et al., Sequencing the Connectome, PLoS One, 2012, 10(10, 1-7. (Year: 2012).*
International Search Report dated Jul. 20, 2017 in connection with PCT International Application No. PCT/US2017/026055.
Written Opinion of the International Searching Authority dated Jul. 20, 2017 in connection with PCT International Application No. PCT/US2017/026055.
Zador, AM et al., "Sequencing the Connectome", PLoS Biology, Oct. 23, 2010, vol. 10, No. 10.
Wang, H et al., "Calling Cards for DNA-Binding Proteins", Genome Research, Aug. 2007, vol. 17, No. 8; pp. 1202-1209.
Craven, SE et al., "Synaptic Targeting of the Postsynaptic Density Protein PSD-95 Mediated by a Tyrosine-based Trafficking Signal", Journal of Biological Chemistry, Jun. 30, 2000, vol. 275, No. 26, pp. 20045-20051.
Jul. 30, 2021 Extended European Search Report issued in connection with counterpart European Patent Application No. 17779705.7.
Feb. 25, 2020 Reply to Communication Pursuant to Rule 70(2) and 70a(2) EPC filed in connection with counterpart European Patent Application No. 17779705.7.
Dec. 4, 2020 Communication Pursuant to Article 94(3) issued in connection with counterpart European Patent Application No. 17779705.7.
Apr. 12, 2021 Reply to Dec. 4, 2020 Communication Pursuant to Article 94(3) filed in connection with counterpart European Patent Application No. 17779705.7.
Aug. 19, 2021 Communication Pursuant to Article 94(3) issued in connection with counterpart European Patent Application No. 17779705.7.
Jean-Livet et al: "Transgenic strategies for combinatorial expression of fluorescent proteins in the nervous system", Nature, vol. 450, No. 7166, Nov. 1, 2007 (Nov. 1, 2007), pp. 56-62, XP055502994, Longon ISSN: 0028-0836, DOI1 10.1038/nature06293.
Feb. 25, 2022 Reply to Aug. 19, 2021 Communication Pursuant to Article 94(3) filed in connection with counterpart European Patent Application No. 17779705.7.

(Continued)

*Primary Examiner* — Amy M Bunker
(74) *Attorney, Agent, or Firm* — Gary J. Gershik

(57) ABSTRACT

The present invention provides a composition comprising a plurality of labeled neurons, each of which is labeled by an expression construct that encodes a unique barcoded nucleic acid.

17 Claims, 40 Drawing Sheets
Specification includes a Sequence Listing.

(56) References Cited

OTHER PUBLICATIONS

Jun. 14, 2023 Communication Pursuant to Article 94(3) filed in connection with counterpart European Patent Application No. 17779705.7.
Jun. 14, 2023 Response to First Examination Report filed in connection with Australian Patent Application No. 2017246638.
Jun. 29, 2023 Notice of Acceptance issued in connection with Australian Patent Application No. 2017246638.
Aug. 4, 2023 Response to Apr. 5, 2023 Office Action filed in connection with Canadian Patent Application 3,020,317.

* cited by examiner a  b

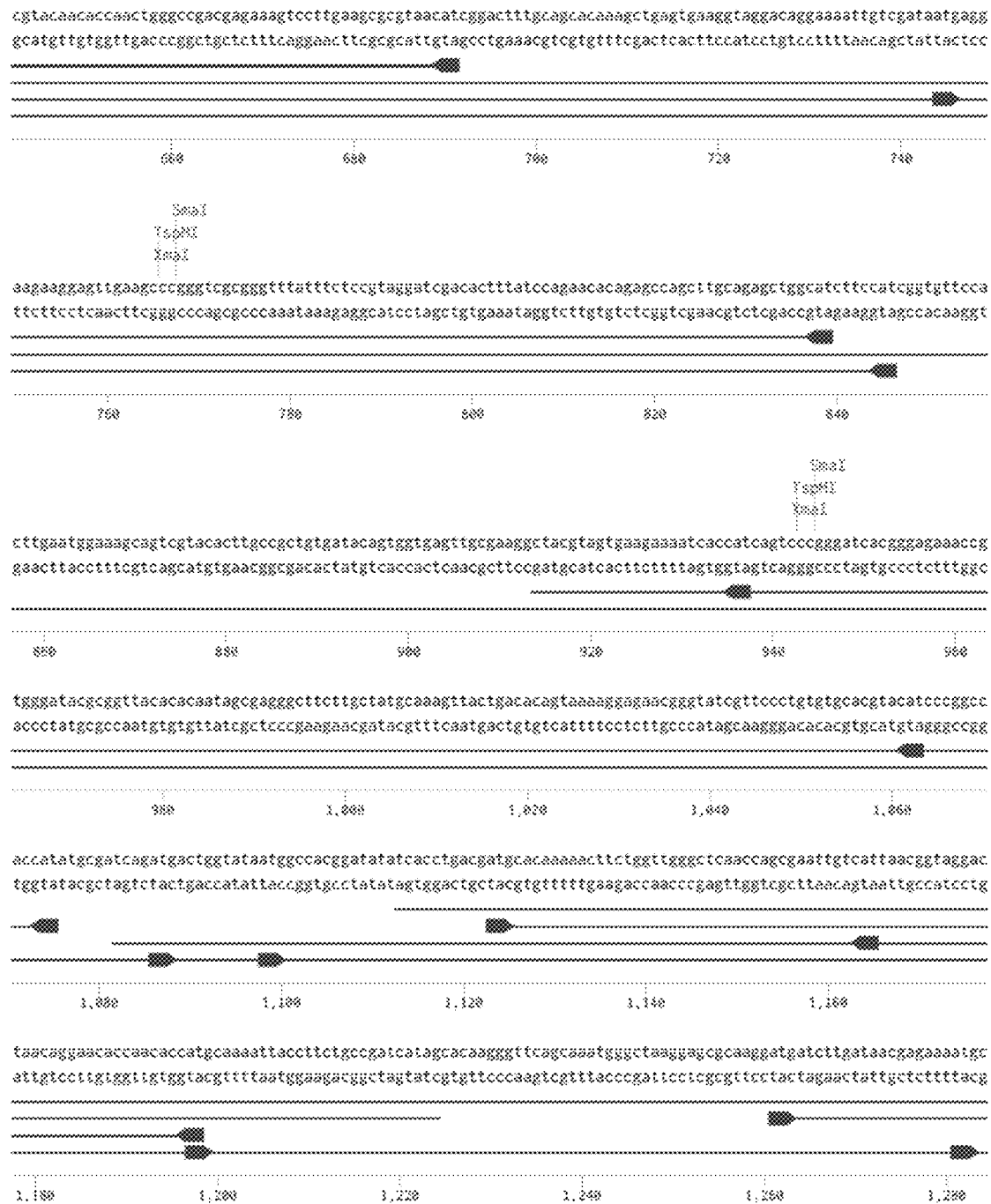
Figure 21 con't.

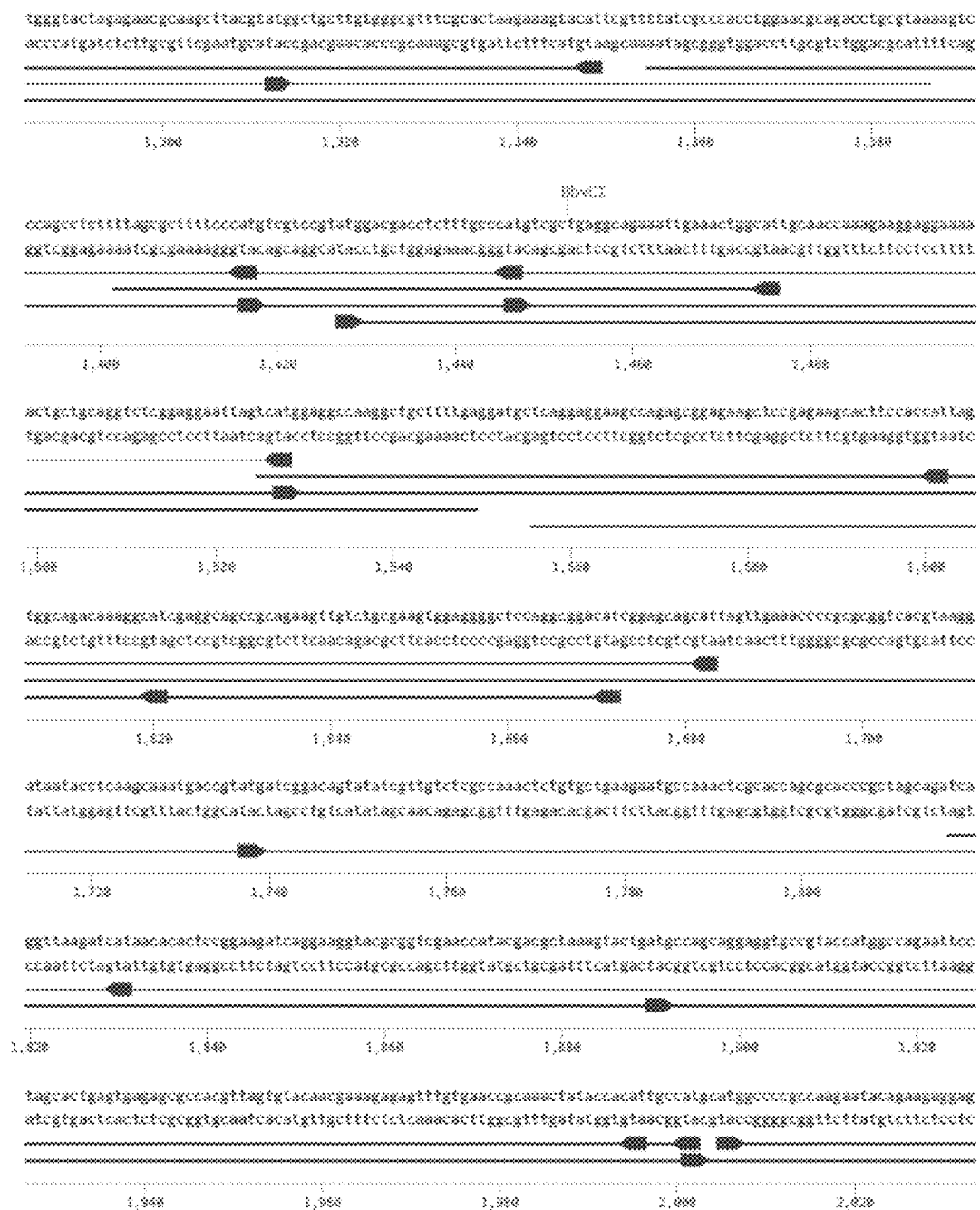
Figure 21 con't.

Figure 21 con't.

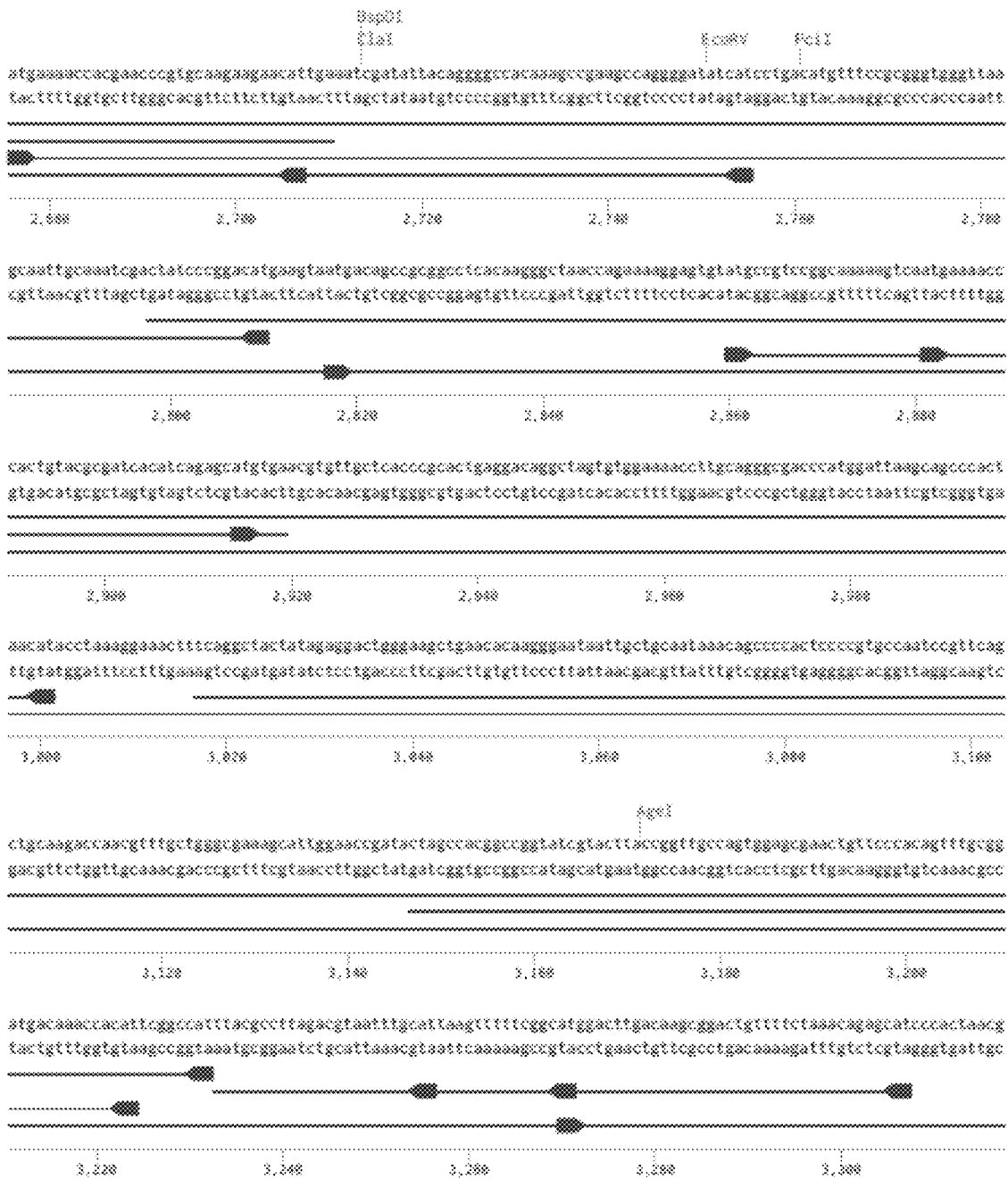
Figure 21 con't.

Figure 21 con't.

Figure 21 con't.

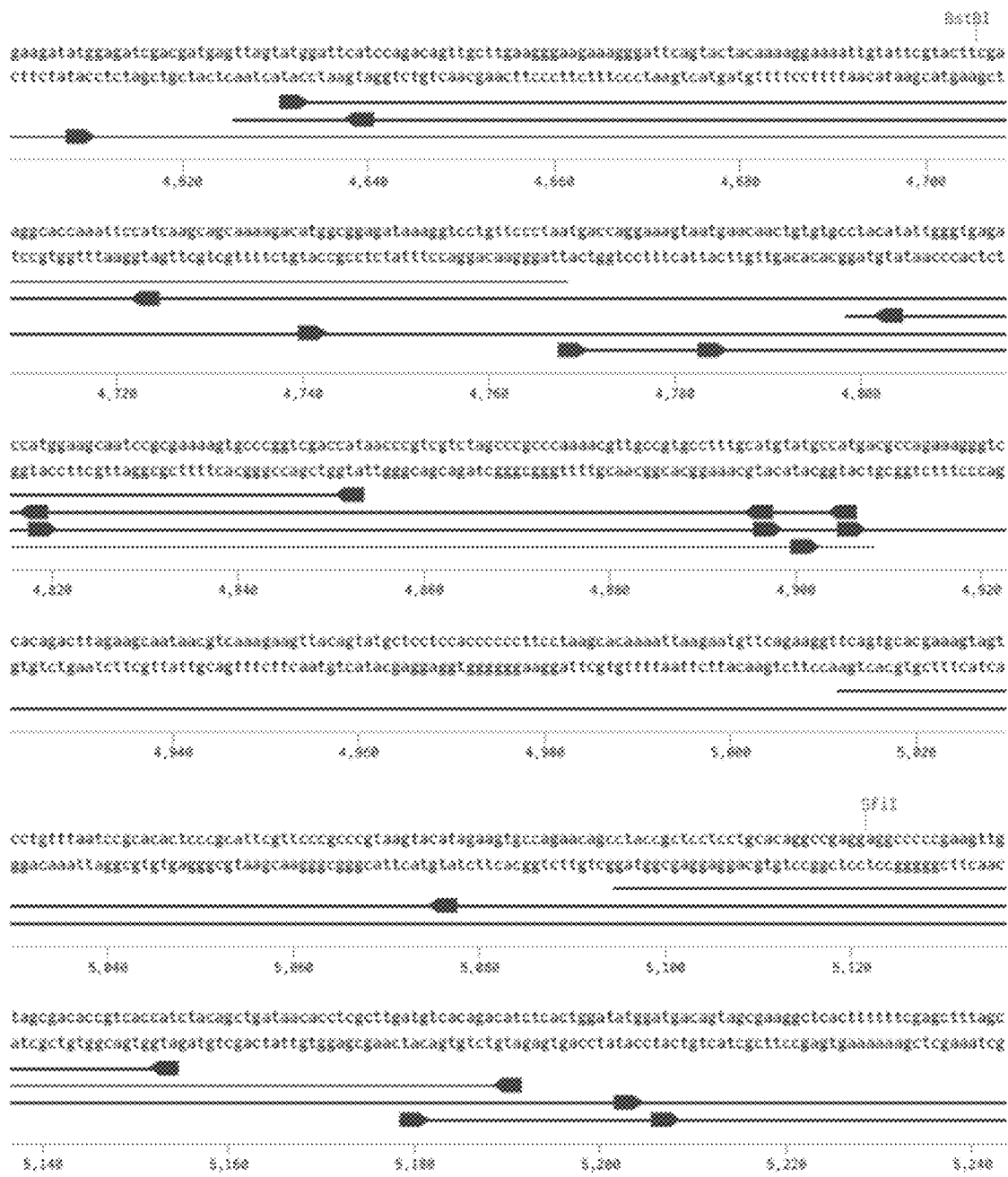
Figure 21 con't.

Figure 21 con't.

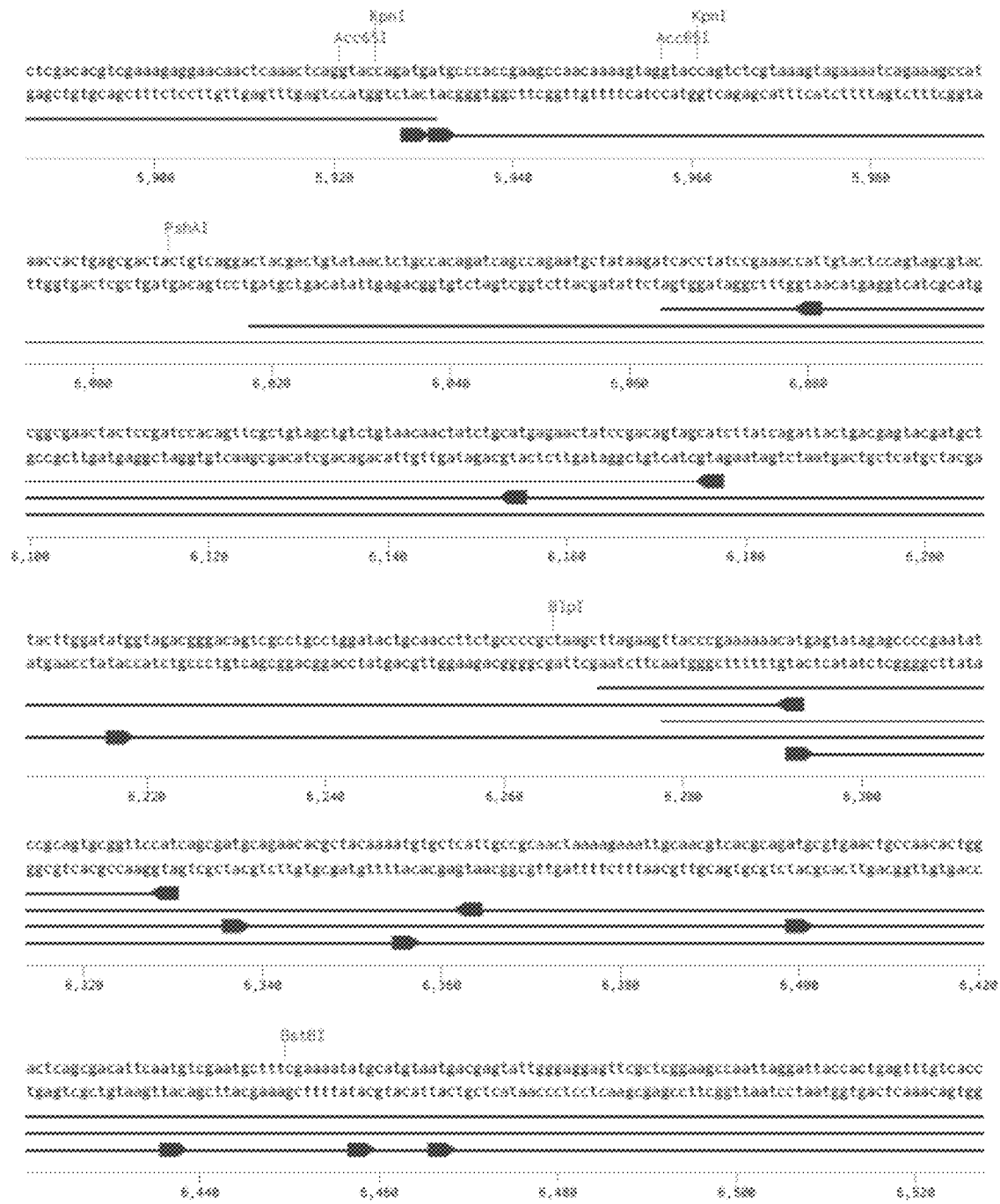
Figure 21 con't.

Figure 21 con't.

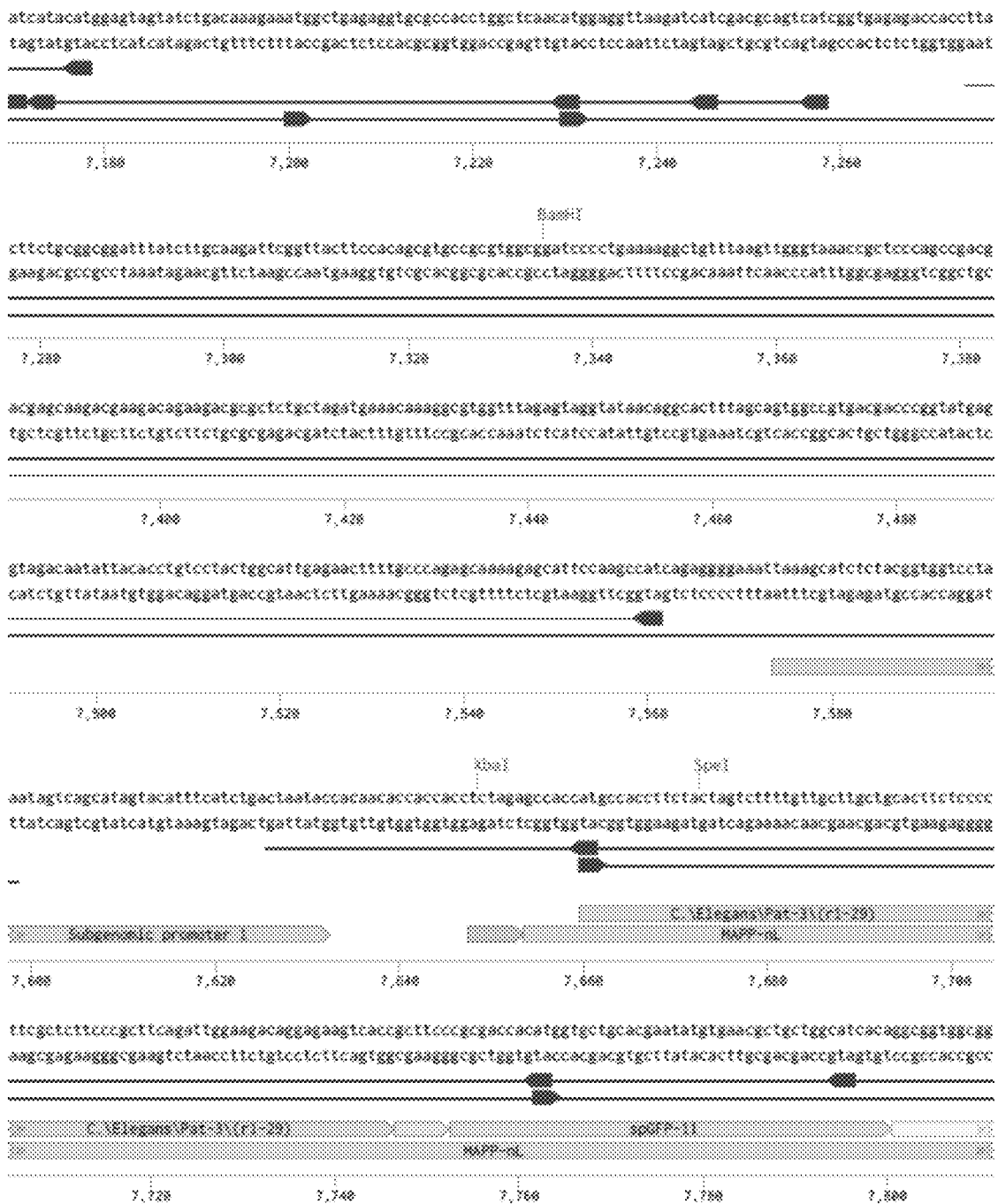
Figure 21 con't.

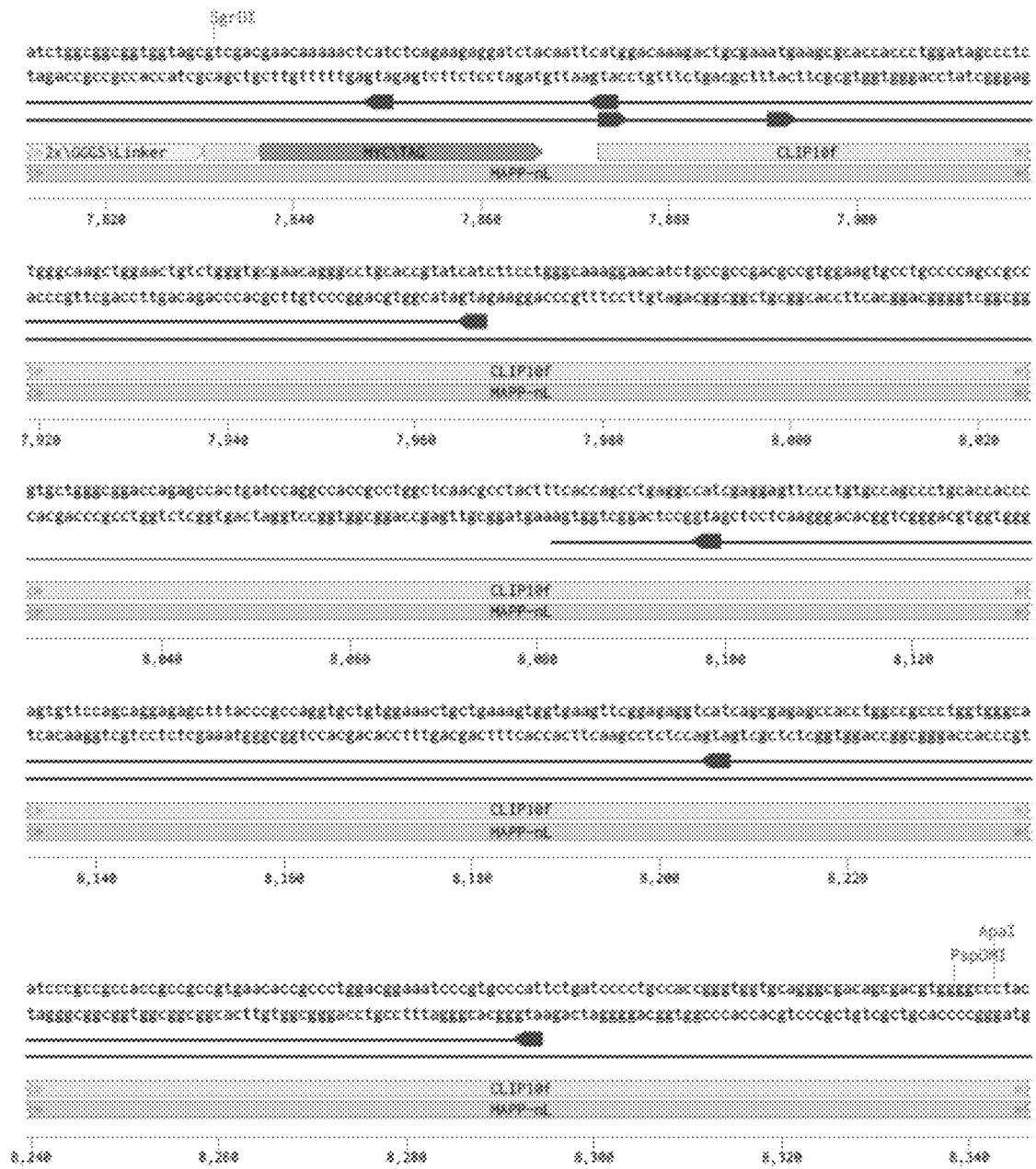
Figure 21 con't.

Figure 21 con't.

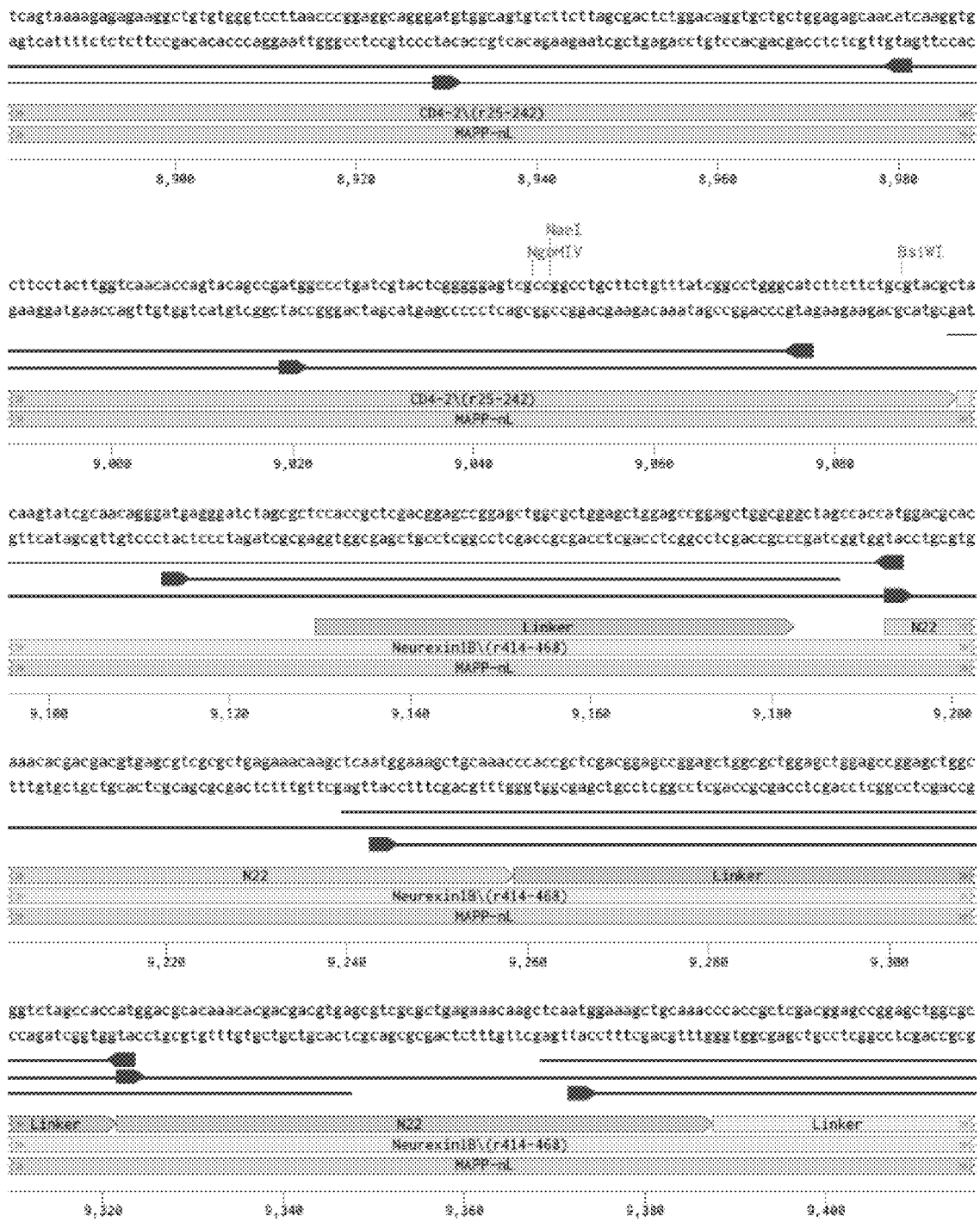
Figure 21 con't.

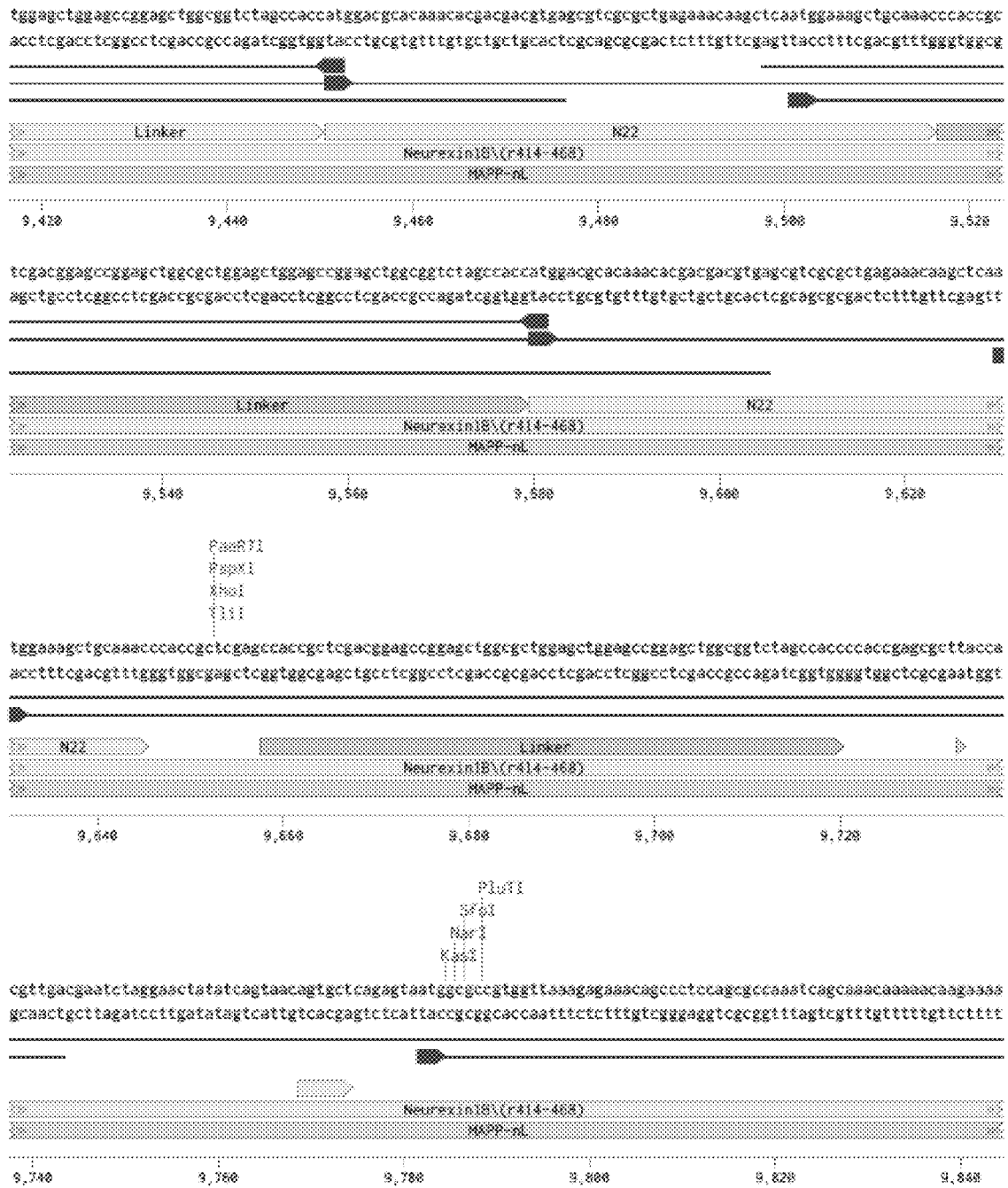
Figure 21 con't.

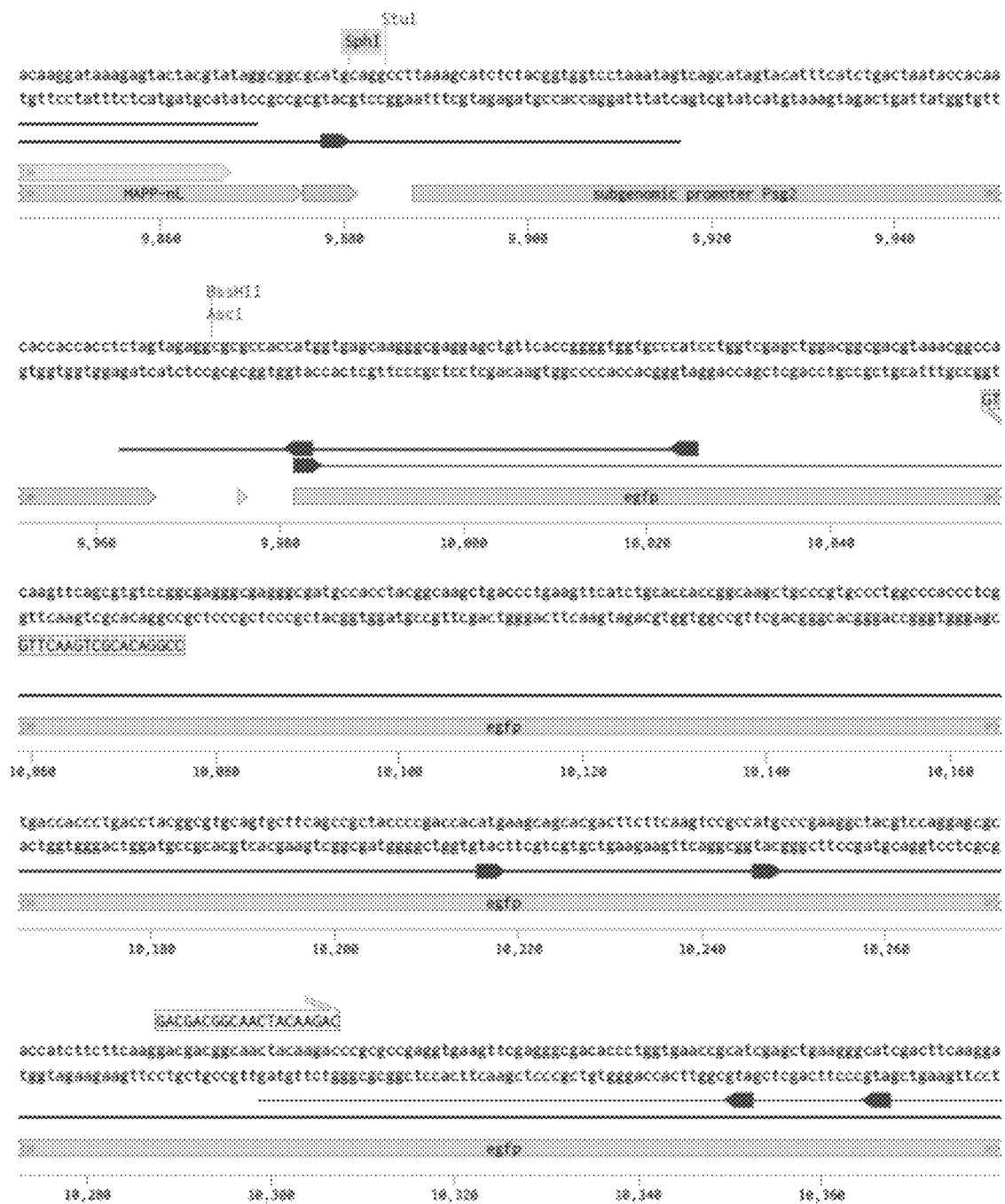
Figure 21 con't.

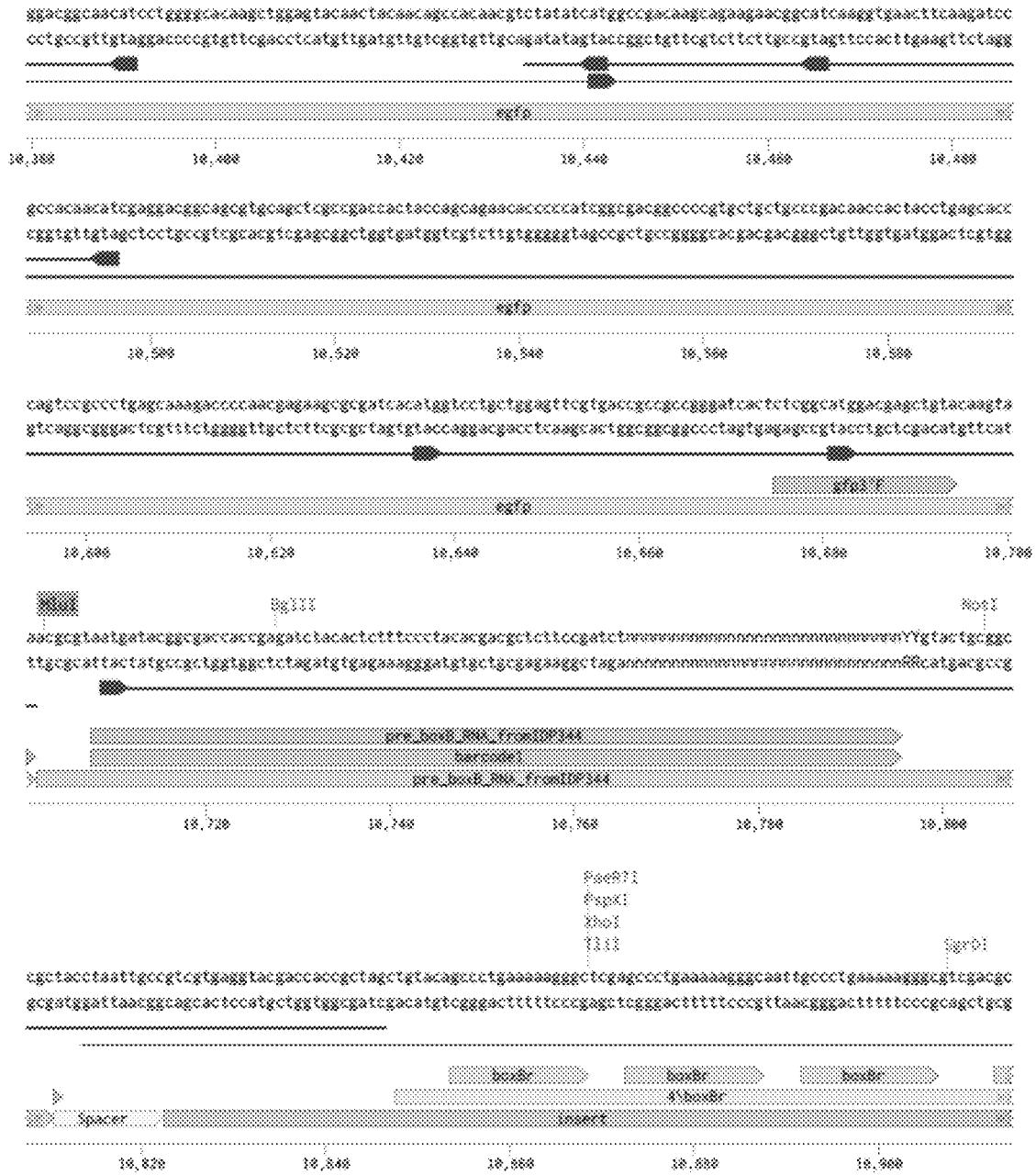
Figure 21 con't.

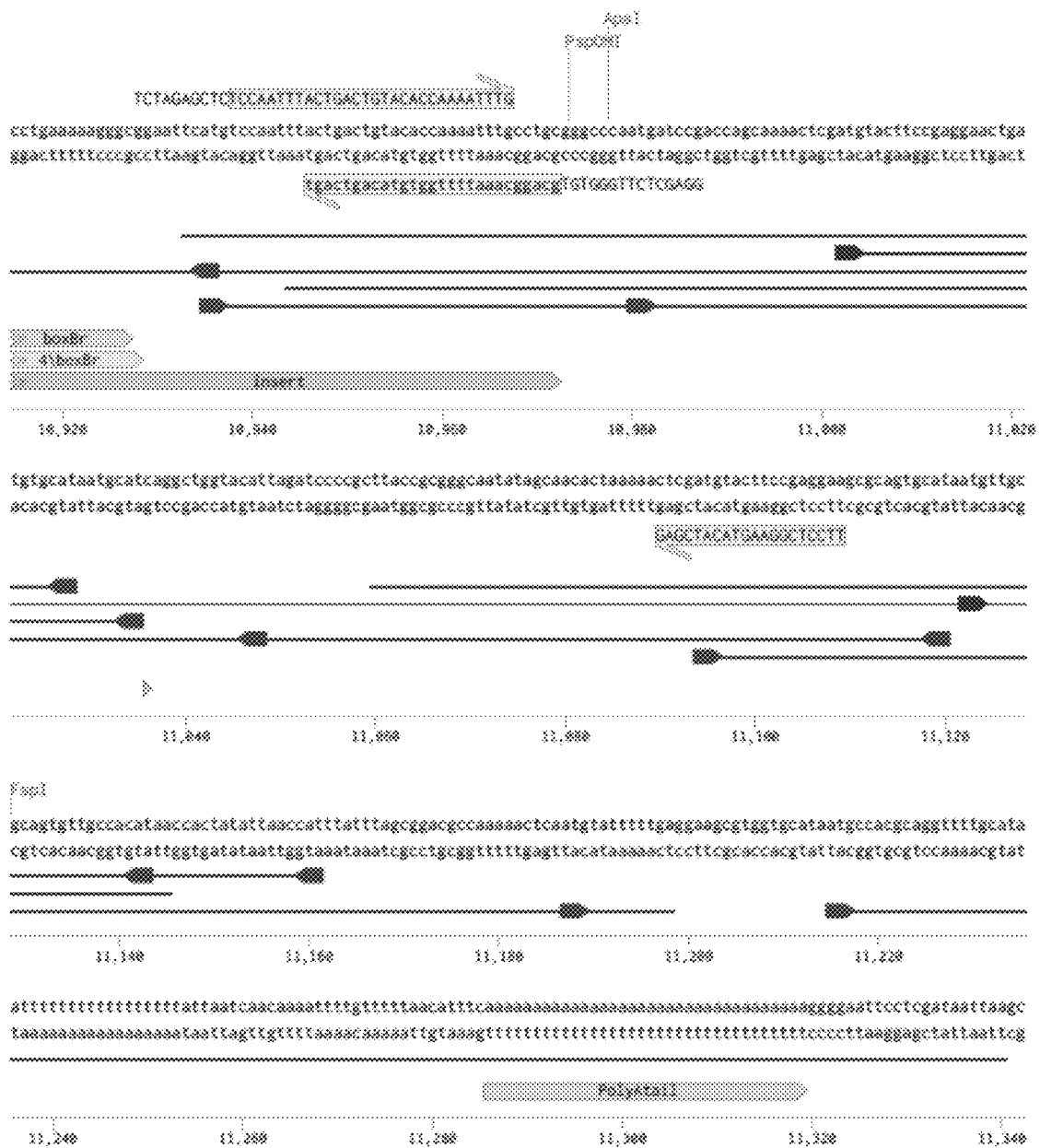
Figure 21 con't.

Figure 21 con't.

MULTIPLEXED ANALYSIS OF NEURON PROJECTIONS BY SEQUENCING

This application is a § 371 national stage of PCT International Application No. PCT/US2017/026055, filed Apr. 5, 2017, and claims priority of U.S. Provisional Patent Application No. 62/320,386, filed Apr. 8, 2016, the entire contents of each of which are hereby incorporated herein by reference.

This invention was made with government support under grant number NS073129, DA036913 and CA045508 awarded by the National Institutes of Health. The government has certain rights in the invention.

This application incorporates-by-reference nucleotide and/or amino acid sequences which are present in the file named "181005_88293-PCT-US_Sequence_Listing CAE.txt", which is 22.2 kilobytes in size, and which was created Oct. 5, 2018 in the IBM-PC machine format, having an operating system compatibility with MS-Windows, which is contained in the text file filed Oct. 5, 2018 as part of this application.

Throughout this application, various publications are referenced, including referenced in parenthesis. Full citations for publications referenced in parenthesis may be found listed at the end of the specification immediately preceding the claims. The disclosures of all referenced publications in their entireties are hereby incorporated by reference into this application in order to more fully describe the state of the art to which this invention pertains.

BACKGROUND OF INVENTION

Area-to-area connections have been mapped out systematically in the mouse brain, but only using bulk labeling techniques that obscure the diversity of single neuron projections arising from intermingled heterogeneous populations. Here a novel approach is described in which random nucleotide sequences ("barcodes") are introduced into neurons to convert projection-mapping into a form that exploits high-throughput sequencing (HTS) technology. In Multiplexed Analysis of Projections by Sequencing (MAPseq), single neuron axonal projections are labeled by viral expression of RNA barcodes, resulting in an efficient and massively parallel method for determining the projection targets of large ensembles of individual neurons. MAPseq was applied to the locus coeruleus (LC) and it was demonstrated that most individual LC neurons have preferred cortical targets. By recasting neuroanatomy, which is traditionally viewed as a problem of microscopy, as a problem of sequencing, MAPseq harnesses advances in HTS to permit high-throughput interrogation of brain circuits.

SUMMARY OF THE INVENTION

Neurons transmit information to distant brain regions via long-range axonal projections. In some cases, functionally distinct populations of neurons are intermingled within a small region. For example, nearby hypothalamic nuclei mediate basic drives including appetite, aggression, and sexual attraction (Kennedy et al., 2014; Sternson, 2013), and neurons from these nucleic acid project to distinct targets. In visual cortical area V1, responses to visual stimuli are matched to the properties of the higher visual areas to which the neurons project (Glickfeld et al., 2013; Movshon and Newsome, 1996). Findings such as these suggest that the information transmitted by individual neurons may be tailored to their targets. However, there is currently no high-throughput method for determining the diverse projection patterns of neurons.

At present, there is a steep tradeoff between throughput and resolution in anatomical approaches to mapping long-range connections. In conventional brain mapping studies, a fluorescent or enzymatic label is used to enable visualization of cell bodies and distal projections by light microscopy. Maximal throughput is achieved using bulk labeling techniques, which sample the aggregate architecture of a neuronal population (Oh et al., 2014). Such methods are fast, and there have been several large-scale efforts to map mesoscopic connectivity systematically (Oh et al., 2014; Zingg et al., 2014). However, such bulk methods obscure the diversity of single neuron projections arising from heterogeneous populations of neurons. Consider, for example, a single source area that projects to three downstream areas (FIG. 1a). This projection pattern implies that neurons in the source area can send information to the three downstream areas. However, identical bulk projection patterns could arise in multiple ways: from a one-to-one architecture, in which each neuron targets only a single downstream area (left); from a one-to-many architecture, in which each neuron targets every downstream area (middle); or from more complicated architectures (right). Although bulk-labeling approaches can be refined by exploiting transgenic animals engineered to express markers (such as recombinases) in genetically defined subsets of neurons (Tasic et al., 2016), such strategies presuppose that the markers target functional classes of neurons.

Distinguishing among the architectures shown in FIG. 1a requires single neuron resolution. Current methods for achieving single neuron resolution require labeling one or at most a few cells per brain individually (Economo et al., 2016), a labor-intensive approach that affords high resolution at the cost of low throughput. Although single-neuron tracing can be multiplexed by labeling individual neurons with different colored fluorophores (Ghosh et al., 2011; Livet et al., 2007), in practice the extent of multiplexing is limited by the number of colors—at most 5-10—that can be resolved by microscopy.

MAPseq is a novel approach in which brain mapping is recast as a problem of high-throughput DNA sequencing, achieving multiplexing by using short, random RNA barcodes to disambiguate individual neurons (Mayer et al., 2015; Walsh and Cepko, 1992; Zador et al., 2012) (FIG. 1b). The key advantage of using barcodes is that their diversity grows exponentially with the length of the sequence. The pool of unique barcode identifiers is effectively infinite; even a 30 nucleotide (nt) sequence has a potential diversity of $4^{30} \approx 10^{18}$ barcodes, far surpassing the $\sim 10^8$ neurons in the mouse brain (Herculano-Houzel et al., 2006). Because high-throughput sequencing can quickly and inexpensively distinguish these barcodes, MAPseq has the potential read out the projections of thousands or even millions of individual neurons in parallel within a single brain (FIG. 1c).

In MAPseq, neurons are uniquely labeled in a source region by injecting a viral library encoding a diverse collection of barcode sequences. The barcode mRNA is expressed at high levels and is transported into the axon terminals at distal target projection regions (FIG. 1d). Barcode mRNA is extracted from the injection site and from each target region of interest, then the extracted barcode mRNA is sequenced to read out single neuron projection patterns. Spatial resolution is limited mainly by the precision of target dissection. Using this procedure, the brain-wide map of projections from a given area can be determined in less than a week.

DETAILED DESCRIPTION OF THE INVENTION

The present invention provides a composition comprising a plurality of labeled neurons, each of which is uniquely labeled by an expression construct that encodes a barcoded nucleic acid.

In some embodiments, wherein the barcoded nucleic acid contains a binding region that is specifically recognized by a nucleic acid-binding domain.

In some embodiments, wherein the binding region is a boxB motif.

In some embodiments, wherein the binding region is a MS-2 stem-loop motif.

In some embodiments, wherein the expression construct also expresses a chimeric protein containing
   i) a nucleic acid binding domain that specifically binds the barcoded nucleic acid in the neuron; and
   ii) a synaptic trafficking signal,
thereby facilitating transport of the barcoded nucleic acid to the axon terminals of the neuron.

In some embodiments, wherein the chimeric protein is a modified presynaptic protein.

In some embodiments, wherein the presynaptic protein is pre-mGRASP.

In some embodiments, wherein the nucleic acid-binding domain is nλ.

In some embodiments, wherein the nucleic acid-binding domain is a portion of the MS-2 coat protein.

In some embodiments, wherein the chimeric protein further comprises a Myc epitope tag.

In some embodiments, wherein the chimeric protein further comprises a CLIP-tag domain.

In some embodiments, wherein the chimeric protein is MAPP-nλ.

In some embodiments, wherein the chimeric protein is CLAP-1x-nλ.

For example, both MAPP-nλ and CLAP-1x-nλ contain the synaptic trafficking signal sequence of mouse NRXN1b with a nλ RNA binding domain added at a specific position which has previously been reported to not disrupt NRXN1b trafficking (Fairless, 2008). Nonetheless, not every sequence inserted at this position allows proper trafficking of the resulting fusion protein, which is the reason for using only one copy of nλ in CLAP-1x-nλ as opposed to four copies of nλ used in MAPP-nλ. Ideally, simply switching the nλ sequence for the sequence of another RNA binding domain will be sufficient to switch the system, though some trial and error search for linker sequences which join the carrier protein to the RNA binding domain may be necessary. Conversely, adding an RNA binding domain to any other presynaptic protein at a position that does not disrupt endogenous trafficking would be sufficient to turn this protein into a MAPseq carrier protein. Any highly specific RNA binding domain-recognition site pair can be used for this purpose. Thus, Example 6 provides two MAPseq carrier protein sequences, however, other such carrier proteins will be readily understood by any person of skill in the art of molecular biology.

Figure 18:
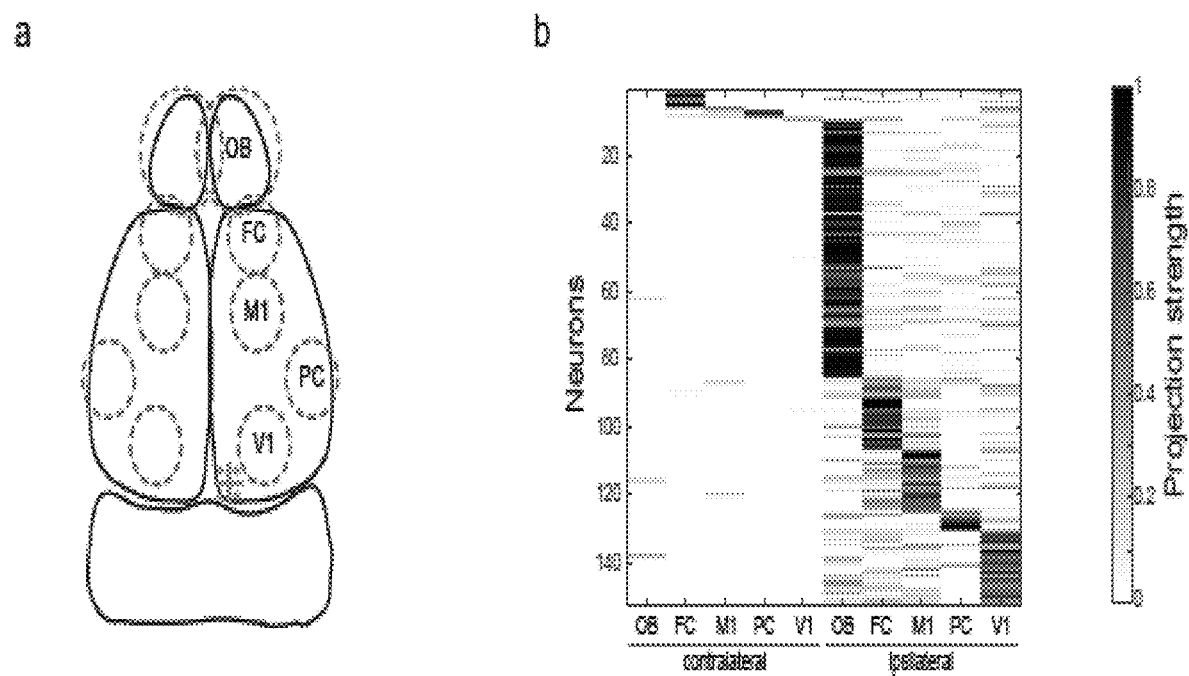
FIG. 18: MAPseq can be performed on small target areas. (a) Schematic of dissected areas. FC=frontal cortex; M1=primary motor cortex; PC=piriform cortex; V1=primary visual cortex. (b) A heatmap of all ~140 neurons traced across 3 independent animals using DH(26S)5' SIN packaged MAPseq virus. All ectopically infected cells (see FIG. 9f) that could have confused tracing results were removed by an abundance cutoff of 1000. Preferential targeting of different ipsilateral areas is clearly evident.
Figure 19:
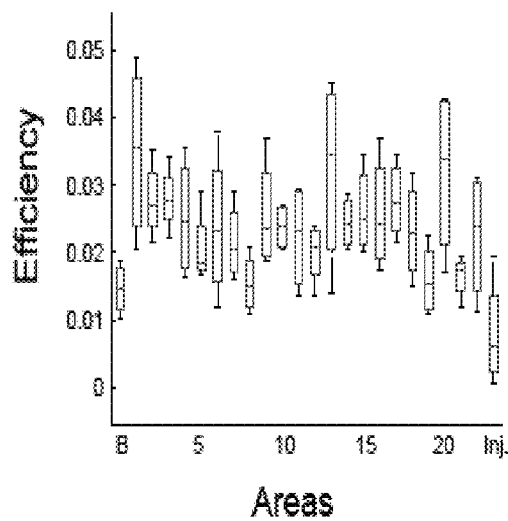
FIG. 19: Efficiency of barcod recovery from total RNA samples. Efficiency of recovery is low and relatively constant across areas (a; n=4 animals) and animals (b).
Figure 19:
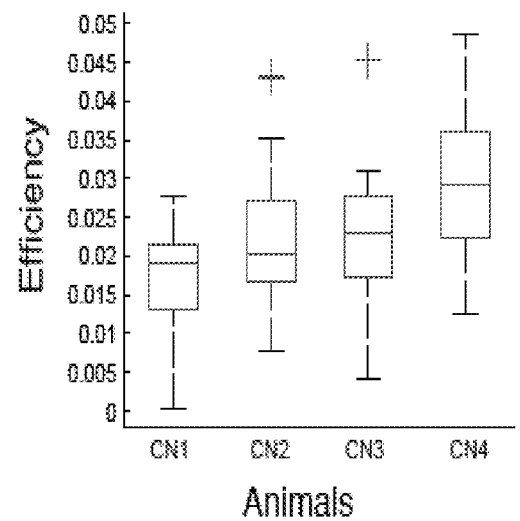

In some embodiments, wherein the expression construct is a modified Sindbus virus. For example, the expression construct depicted in FIGS. 18 and 19 is one such construct which may be used, however variations of this construct will be understood by any person of ordinary skill in the art. Notably, any method which delivers barcodes to the synapse can be utilized for MAPseq. For instance, in addition to Sindbus virus, a number of ways to deliver transgenes to neurons, such as viruses including but not limited to adeno-associated virus (AAV), lentivirus, herpes simplex virus (HSV), pseudorabies virus (PRV), chicken anaemia virus (CAV) or rabies may be used for MAPseq. Other methods of delivery include electroporation and transgenesis, as well as several other methods known to a person of ordinary skill in the art.

In some embodiments, wherein the modified Sindbus virus is produced using a defective helper RNA which produces virions that are neurotropic and propagation-incompetent.

In some embodiments, wherein the modified Sindbus virus is produced using the defective helper RNA DH-BB(5' SIN;TE12ORF).

In some embodiments, wherein at least 50%, more preferably at least 75%, more preferably at least 80%, more preferably at least 90%, more preferably at least 95%, 96%, 97%, 98% or 99% of the labeled neurons are uniquely labeled with a barcoded nucleic acid.

In some embodiments, wherein the barcode in each of the barcoded nucleic acids has a length of (k) nucleotides, wherein $4^k$ is greater than the number of neurons to be labeled.

In some embodiments, wherein the barcoded nucleic acid contains a barcode region that is about 30 nucleotides in length.

In some embodiments, wherein the barcoded nucleic acid encodes a fluorescent marker.

In some embodiments, wherein the barcoded nucleic acid is RNA.

The invention also provides a method for obtaining a plurality of labeled neurons, comprising infecting neurons with a modified, barcoded Sindbus virus library. In some embodiments, neurons in the brain are labeled by injecting the barcoded virus library into only a specific portion or structure of the brain or brain-stem. For example, the LC is an example of one such specific site, however, any other specific site or location of the brain may be injected. In other embodiments, the barcoded virus library is injected into more than one portion or structure of the brain.

In some embodiments, wherein the library is sufficiently diverse to uniquely label at least 50%, more preferably at least 75%, more preferably at least 80%, more preferably at least 90%, more preferably at least 99% of the total number of neurons that are infected.

In some embodiments, wherein the neurons are infected with a barcoded Sindbus virus library at a multiplicity of infection (MOI) of about 1.

In some embodiments, further comprising infecting the neurons with a library which is capable of altering gene expression.

In some embodiments, wherein the functional library is a CRISPR library.

In some embodiments, wherein the functional library is a shRNA library.

In some embodiments, wherein a drug is applied to the plurality of labeled neurons to determine if the drug is capable of counteracting a wiring defect in a neuron caused by the altered gene expression from the functional library.

The invention also provides a process for obtaining a map of single neuron projections in a region containing projections of the plurality of labeled neurons, comprising
  i) dissecting the region containing projections of the plurality of barcoded neurons into sections;
  ii) isolating the barcoded nucleic acids from each dissected section;
  iii) amplifying the isolated barcoded nucleic acids;
  iv) sequencing the amplified barcoded nucleic acids; and
  v) determining associations between identical barcode sequences
thereby obtaining a map of single neuron projections in the region. The region being mapped may have projections from neurons belonging to the central nervous system or peripheral nervous system. Thus, a neuronal map of any region e.g., any organ or tissue, for example muscle or gut tissue, which neurons project through may be obtained using MAPseq.

In some embodiments, wherein in step (i) the region is dissected by a gross dissection method.

In some embodiments, wherein in step (i) the region is dissected by a laser-capture microdissection method.

In some embodiments, wherein in step (ii) the barcoded nucleic acids are isolated by TIVA tagging.

In some embodiments, wherein in step (ii) a known amount of spike-in nucleic acid molecules is added to every sample of isolated barcoded nucleic acids in order to determine the efficiency of barcode sequence recovery.

In some embodiments, wherein step (ii) further comprises reverse transcription of the isolated barcoded nucleic acids.

In some embodiments, wherein step (ii) further comprises adding a slice specific identifier (SSI) to the barcoded nucleic acids from a dissected area.

In some embodiments, wherein step (ii) further comprises adding a unique molecular identifier (UMI) to each barcoded nucleic acid from each dissected area.

In some embodiments, wherein the sequences of the barcoded nucleic acids are obtained by a FISSEQ method.

In some embodiments, wherein in step (v) a threshold of true, non-contaminating barcode expression is determined by the number of barcode sequences recovered from cells that lack a barcoded construct.

In some embodiments, wherein in step (v) the barcode sequences in the injection site (reference barcodes) are matched with the barcode sequences in the target sites to create a barcode matrix of size [number of reference barcodes]×[number of target sites+number of injection sites].

In some embodiments, wherein each target area of the barcode matrix is normalized by the number of unique spike-in molecules detected in each.

In some embodiments, wherein each target area of the barcode matrix is normalized by the amount of β-actin per µl of total RNA.

In some embodiments, wherein all barcodes are normalized to sum to 1 across all target areas.

In some embodiments, wherein in step (v) peaks of barcode molecule counts are defined by
i) being at least half as high as the maximal barcode count across all target sites;
ii) being separated by at least three slices; and
iii) rising at least their half maximal height from their surroundings ('prominence')
thereby defining peaks for use in determining associations between identical barcode sequences.

In some embodiments, wherein the labeled neurons belong to the central nervous system.

In some embodiments, wherein the labeled neurons belong to the peripheral nervous system.

In some embodiments, a map of single neuron projections.

In some embodiments, a method for ascertaining the effects of a drug on neurons comprising obtaining a map of single neuron projections before and after exposure of the neurons to a drug.

Each embodiment disclosed herein is contemplated as being applicable to each of the other disclosed embodiments. Thus, all combinations of the various elements described herein are within the scope of the invention.

TERMS

Unless otherwise defined, all technical and scientific terms used herein have the same meaning as commonly understood by a person of ordinary skill in the art to which this invention belongs.

As used herein, and unless stated otherwise or required otherwise by context, each of the following terms shall have the definition set forth below.

As used herein, "about" in the context of a numerical value or range means ±10% of the numerical value or range recited or claimed, unless the context requires a more limited range.

The terms "template", "nucleic acid", and "nucleic acid molecule", are used interchangeably herein, and each refers to a polymer of deoxyribonucleotides and/or ribonucleotides. "Nucleic acid" shall mean any nucleic acid, including, without limitation, DNA, RNA and hybrids thereof. The nucleic acid bases that form nucleic acid molecules can be the bases A, C, G, T and U, as well as derivatives thereof. "Genomic nucleic acid" refers to DNA derived from a genome, which can be extracted from, for example, a cell, a tissue, a tumor or blood.

As used herein "contig" and "continguous" refers to a set of overlapping sequence or sequence reads.

As used herein, the term "amplifying" refers to the process of synthesizing nucleic acid molecules that are complementary to one or both strands of a template nucleic acid. Amplifying a nucleic acid molecule typically includes denaturing the template nucleic acid, annealing primers to the template nucleic acid at a temperature that is below the melting temperatures of the primers, and enzymatically elongating from the primers to generate an amplification product. The denaturing, annealing and elongating steps each can be performed once. Generally, however, the denaturing, annealing and elongating steps are performed multiple times (e.g., polymerase chain reaction (PCR)) such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplified nucleic acid molecule" refers to the nucleic acid molecules, which are produced from the amplifying process.

As used herein, the term "read" or "sequence read" refers to the nucleotide or base sequence information of a nucleic acid that has been generated by any sequencing method. A read therefore corresponds to the sequence information obtained from one strand of a nucleic acid fragment. For example, a DNA fragment where sequence has been generated from one strand in a single reaction will result in a single read. However, multiple reads for the same DNA strand can be generated where multiple copies of that DNA fragment exist in a sequencing project or where the strand has been sequenced multiple times. A read therefore corresponds to the purine or pyrimidine base calls or sequence determinations of a particular sequencing reaction.

As used herein, the terms "sequencing", "obtaining a sequence" or "obtaining sequences" refer to nucleotide sequence information that is sufficient to identify or characterize the nucleic acid molecule, and could be the full length or only partial sequence information for the nucleic acid molecule.

As used herein the term "sequencing library" refers to a mixture of DNA fragments comprising the total genomic DNA from a single organism for use in sequencing. Next-generation sequencing libraries are generally size-selected and ligated to sequencing adaptors prior to sequencing.

As used herein, the term "sequencing adaptor" refers to oligos bound to the 5' and 3' end of each DNA fragment in a sequencing library. Adaptors may contain platform-dependent sequences that allow amplification of the fragment as well as sequences for priming the sequencing reaction.

As used herein, the term "barcode" may generally refer to any nucleic acid sequence used for identification purposes. A barcode can be a sequence used to identify a source of origin, for example a cell, genome, sample or another nucleic acid to which it is attached. In the context of MAPseq, a barcode may refer to a stretch of expressed, randomized nucleic acids which is used to uniquely label an individual neuron. Thus, a barcoded nucleic acid contains a barcode portion as well as other portions, e.g. protein-encoding portions. In addition, a sequencing barcode, also known as a sequencing index, refers to a unique DNA sequence, for instance within a sequencing adaptor, which is used to identify the genomic origin of each amplicon in a sequencing library. Similarly, other types of barcodes used in this application include a slice specific identifier (SSI) and a unique molecular identifier (UMI).

As used herein, the term "multiplex" refers to pooling or otherwise mixing amplicons generated from multiple sources, sequencing the entire collection of amplicons in a single sequencing run and subsequently sorting and identifying the source of each read by a barcode sequence.

As used herein, the term "uniquely labeled neuron" in the context of MAPseq refers to a neuron which contains a barcoded nucleic acid that is not found in any other labeled neuron in the plurality of labeled neurons. In a practical application of MAPseq, at least 50%, more preferably at least 75%, more preferably at least 802, more preferably at least 90%, more preferably at least 95%, 96%, 97%, 98% or 99% of the neurons labeled with a barcoded nucleic acid are uniquely labeled neurons.

As used herein, the term "expression construct" or "expression vector" refers to any engineered nucleic acid which is introduced into a cell and is capable of expressing an RNA or protein. Non-limiting examples of expression constructs include recombinant plasmids and recombinant viral nucleic acids. Introduction of an engineered nucleic acid into a cell can be accomplished by a variety of methods including, but not limited to, transformation and transfection techniques, viral transduction, electroporation, chemically-induced uptake of exogenous nucleic acids, hydrodynamic delivery, lipofection, sonoporation and other methods known to a person of ordinary skill in the field of molecular biology. In one embodiment of MAPseq, Sindbus virus is used to label neurons with unique barcodes, however, a variety of methods for transgene delivery and expression such as those listed above may also be used for this purpose.

As used herein, the term "chimeric protein," also known as a "fusion protein," refers to any protein sequence which contains sequences from different sources. In MAPseq, a chimeric protein is used to bind a barcoded nucleic acid in a neuron and transport the barcoded nucleic acid to the synapse or axon of the neuron. The chimeric protein may be a modified synaptic or non-synaptic protein. Notably, transport by the chimeric protein should not be necessary when expression of the barcoded nucleic acid is high enough to reach axon terminals.

As used herein, the term "nucleic acid binding domain" refers to a protein domain or motif which is capable of recognizing and binding to a specific region of a nucleic acid. Examples of nucleic acid binding domains include nλ, which binds a boxB RNA motif, and MS-2 bacteriophage coat protein, which binds an MS-2 RNA stem-loop motif. Other RNA-binding protein domains which can be utilized in a chimeric carrier protein for MAPseq will be known to any person of ordinary skill in the art, including, but not limited to, customizable PUF class RNA-binding domains and PP7 bacteriophage coat protein binding site cassettes (Chen and Varani, 2013; Larson et al., 2011).

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All publications and other references mentioned herein are incorporated by reference in their entirety, as if each individual publication or reference were specifically and individually indicated to be incorporated by reference. Publications and references cited herein are not admitted to be prior art.

This invention will be better understood by reference to the Experimental Details which follow, but those skilled in the art will readily appreciate that the specific experiments detailed are only illustrative of the invention as defined in the claims which follow thereafter.

Experimental Details

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Methods—MAPP-nλ

MAPP-nλ is a modified version of pre-mGRASP (Kim, 2011). The pre-mGRASP protein was stripped of the 2A-cerulean fusion and four repeats of the nλ RNA binding domain (Daigle and Ellenberg, 2007) were added in the cytoplasmic tail after amino acid 287 of the original pre-mGRASP sequence. A Myc epitope tag followed by the CLIP-tag domain (New England Biolabs) was also added after amino acid 59 of the original pre-mGRASP protein.

Methods—Sindbis Virus Barcode Library

The virus used in this study is based on a dual promoter pSinEGdsp construct (Kawamura, 2003). MAPP-nλ was inserted after the first subgenomic promoter. Downstream of the second subgenomic promoter, the GFP coding region was inserted followed by closely spaced NotI and MluI restriction sites and four repeats of the boxB motif (Daigle and Ellenberg, 2007). Using this construct, a high diversity plasmid library was produced by inserting a diverse pool of double stranded ultramers (Integrated DNA Technologies) with sequence 5'-AAG TAA ACG CGT AAT GAT ACG GCG ACC ACC GAG ATC TAC ACT CTT TCC CTA CAC GAC GCT CTT CCG ATC TNN NNN NNN NNN NNN NNN NNN NNN NNN NNN NYY GTA CTG CGG CCG CTA CCT A-3' between the NotI and MluI sites. Sindbis virus was produced as previously described (Kebschull, 2015) using either the conventional DH(26S)5' SIN helper (Bredenbeek, 1993) or the new DH-BB(5' SIN;TE12) (Kebschull, 2015) helper. The titer of the resulting virus was determined by qPCR as previously described (Kebschull, 2015) and the viral library diversity was determined by Illumina sequencing of the RNaseI protected genomic virus RNA.

Methods—Injections

Animal procedures were approved by the Cold Spring Harbor Laboratory Animal Care and Use Committee and carried out in accordance with National Institutes of Health standards.

180 nl of $2\times10^{10}$ GC/ml barcoded Sindbis virus was pressure injected uni- or bilaterally into LC of 8-10 week old C57BL/6 males (Jackson Labs) as described (Cetin, 2007). The animal skulls were leveled on two axes using lambda and bregma for the AP axis and two millimeters laterally from the midpoint between lambda and bregma for the lateral axis. The coordinates AP=−5.4 mm, ML=0.8 mm, DV=2.9 mm and 3.1 mm were used for LC and the depth was measured from the surface of the brain. Each DV coordinate was injected with 90 nl of virus, waiting ten minutes in between each depth. Animals were sacrificed 44 h post injection. For immunofluorescence, RNA in situ and histology, animals were transcardially perfused with ice cold saline (9 g/l) followed by 4% PFA (Electron Microscopy Sciences) in 0.1M Phosphate buffer. For RNA work the fresh brain was extracted and flash froze on dry ice.

For measurements of MAPseq efficiency, red retrobeads (Lumafluor) were injected into the right OB of 8-12 week old C57BL/6 males (Jackson Labs). Briefly, the center of the right OB was roughly determined, and measuring +/−mm from the center in the AP axis, two craniotomies 2 mm apart were performed. The beads were sonicated for 20 minutes prior to injection in order to homogenize the solution. 210 nl of stock concentration of beads was injected at three different depths (0.3 mm, 0.6 mm and 0.9 mm DV from the surface of the OB) as described (Cetin, 2007). Twenty-four hours later, barcoded Sindbis virus was injected into right LC as above. The animals were sacrificed 44-48 h after Sindbis injection.

Methods—Immunofluorescence and ISH

Anti-GFP staining and RNA in situ hybridization was performed on 6 μm thick paraffin sections. For immunofluorescence, a rabbit anti-GFP antibody ab290 (Abcam) was used after heat induced antigen retrieval. In situ hybridization was performed using the Panomics ViewRNA ISH Tissue kit (Affymetrix) using anti-GFP probe VF1-10141 according to the manufacturer's protocol (10 minutes boiling and 10 minutes protease treatment). Anti-TH staining was performed on floating 70 μm vibratome sections using rabbit anti-TH antibody SAB4300675 (Sigma-Aldrich).

Methods—Spike-in RNA

To produce spike-in RNA, a double stranded ultramer (Integrated DNA Technologies) with sequence 5'-GTC ATG ATC ATA ATA CGA CTC ACT ATA GGG GAC GAG CTG TAC AAG TAA ACG CGT AAT GAT ACG GCG ACC ACC GAG ATC TAC ACT CTT TCC CTA CAC GAC GCT CTT CCG ATC TNN NNN NNN NNN NNN NNN NNN NNN NAT CAG TCA TCG GAG CGG CCG CTA CCT AAT TGC CGT CGT GAG GTA CGA CCA CCG CTA GCT GTA CA-3' was created. The resulting dsDNA was then in vitro transcribed using the mMessage mMachine T7 in vitro transcription kit (Thermo Fisher) according to the manufacturer's instructions.

Methods—qPCR

Total RNA was reverse transcribed using oligodT primers and Superscript III reverse transcriptase (Thermo Fisher) according to the manufacturer's instructions. The amount of barcode and β-actin cDNA was quantified by qPCR in SYBR green power master mix (Thermo Fisher) according to the manufacturer's instructions using primers 5'-GAC GAC GGC AAC TAC AAG AC-3' and 5'-TAG TTG TAC TCC AGC TTG TGC-3' for barcode cDNA and 5'-CGG TTC CGA TGC CCT GAG GCT CTT-3' and 5'-CGT CAC ACT TCA TGA TGG AAT TGA-3' for β-actin cDNA.

Methods—MAPseq

300 μm thick coronal sections of fresh frozen brains were cut using a Leica CM 3050S cryostat at −12° C. chamber temperature and −10° C. object temperature. To avoid cross-contamination between samples, each section was cut with a fresh, unused part of the blade. Each section was melted onto a clean microscope slide and rapidly froze on dry ice before dissecting out the cortex on dry ice using a cold scalpel blade. During dissection, known fiber tracts were avoided to minimize the contamination of our dataset with fibers of passage. After sample collection, all samples were processed out of order to avoid sample cross-contamination from impacting interpretation of MAPseq results.

Total RNA from tissue samples was extracted using Trizol reagent (Thermo Fisher) according to the manufacturer's instructions. The total RNA from the tissue samples was mixed with spike-in RNA. ds-cDNA produced as previously described (Morris, 2011) using a gene specific primer of form 5'-CTT GGC ACC CGA GAA TTC CAN NNN NNN NNN NNX XXX XXT GTA CAG CTA GCG GTG GTC G-3', where XXXXXX is one of 65 trueseq like SSI and $N_{12}$ is the UMI. The reaction was cleaned using the Qiagen MinElute PCR purification kit according to the manufacturer's instructions and treated the eluted ds cDNA with ExonucleaseI (New England Biolabs) to remove remaining primers. The barcode amplicons were amplified by nested PCR using primers 5'-CTC GGC ATG GAC GAG CTG TA-3' and 5'-CAA GCA GAA GAC GGC ATA CGA GAT CGT GAT GTG ACT GGA GTT CCT TGG CAC CC GAG AAT TCC A-3' for the first PCR and primers 5'-AAT GAT ACG GCG ACC ACC GA-3' and 5'-CAA GCA GAA GAC GGC ATA CGA-3' for the second PCR in Accuprime Pfx Supermix (Thermo Fisher). The amplicons were gel extracted using the Qiagen MinElute Gel extraction kit according to the manufacturer's instructions and pooled the individual sequencing libraries based on qPCR quantification using primers 5'-AAT GAT ACG GCG ACC ACC GA-3' and 5'-CAA GCA GAA GAC GGC ATA CGA-3'. The pooled libraries were then sequenced on an Illumina NextSeq500 high output run at paired end 36 using the SBS3T sequencing primer for paired end 1 and the Illumina small RNA sequencing primer 2 for paired end 2.

Methods—Efficiency Measurements and Single Cell Isolation

After transcardial perfusion with ice-cold aCSF (127 mM NaCl, 25 mM NaHCO$_3$, 1.25 mM NaPO$_4$, 2.5 mM KCl, 2 mM CaCl$_2$, 1 mM MgCl$_2$, and 25 mM D-glucose) the unfixed brain was extracted and the bead-injected OB was flash froze on dry ice before processing it for sequencing as described above. 400 μm thick acute sagittal slices of the remaining right hemisphere were cut in dissection solution (110 mM choline chloride, 11.6 mM ascorbic acid, 3.1 mM Na pyruvic acid, 25 mM NaHCO$_3$, 1.25 mM NaPO$_4$, 2.5 mM KCl, 0.5 mM CaCl$_2$), 7 mM MgCl$_2$, and 25 mM D-glucose) using a Microm HM650V vibratome. Sections containing LC were incubated in aCSF (126 mM NaCl, 20 mM NaHCO$_3$, 3 mM KCl, 1.25 mM NaH$_2$PO$_4$, 2 mM CaCl$_2$, 2 mM MgSO$_4$, and 20 mM D-glucose) containing synaptic blockers (0.05 mM APV, 0.02 mM DNQX and 0.1 μM TTX) for 20 minutes at room temperature. The slices were then digested in aCSF with *Streptomyces griseus* protease (Sigma P5147) at 1 mg/ml at room temperature for 30 min. After washing in aCSF with synaptic blockers, LC was dissected from the digested section and the tissue was triturated to produce a single cell suspension. Individual cells were picked by hand using an inverted fluorescent microscope (Zeiss Observer) and deposited directly into lysis buffer (2.4 μl 0.2% triton, 1 μl 10 mM dNTPs, 1 μl 10 mM RT primer per cell). Sequencing libraries were prepared from the cells as described above for tissue samples.

| Methods - Animals used | | |
|---|---|---|
| Number of animals | Manipulation | Figures based on these animals |
| 4 | Right LC injection with MAPseq virus; dissection of right cortex and olfactory bulb; qPCR and sequencing of barcode RNA | FIG. 3e, 4, 5, 7, 8, 9, 13, 14, 16, 19 |

Methods - Animals used

Figure 1:
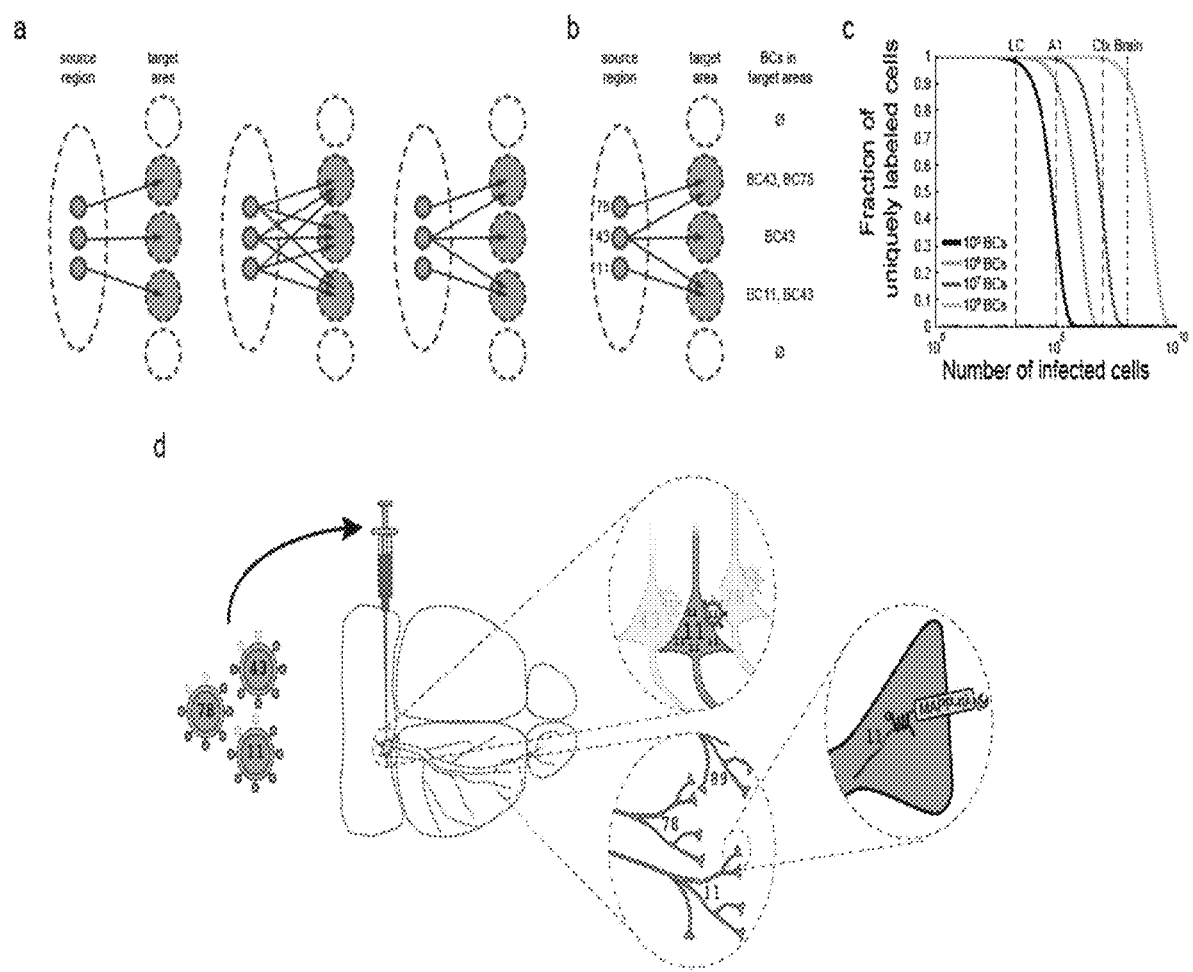
FIG. 1: Barcoding allows high-throughput single neuron tracing. (a) Identical bulk mapping results can arise from different underlying projection patterns. (b) Single neuron resolution can be achieved by randomly labeling neurons with barcodes and reading out barcodes in target areas. (c) The expected fraction of uniquely labeled cells is given by $F=(1-1/N)^{(k-1)}$, where N is the number of barcodes and k is the number of infected cells, assuming a uniform distribution of barcodes. The number of neurons for various mouse brain areas are indicated according to the references Herculano-Houzel et al. (2006) and Schüz and Palm (1989) (A1=primary auditory cortex; Ctx=neocortex). (d) In MAPseq, neurons are infected at low MOI with a barcoded virus library. Barcode mRNA is expressed, trafficked and can be extracted from distal sites.
Figure 2:
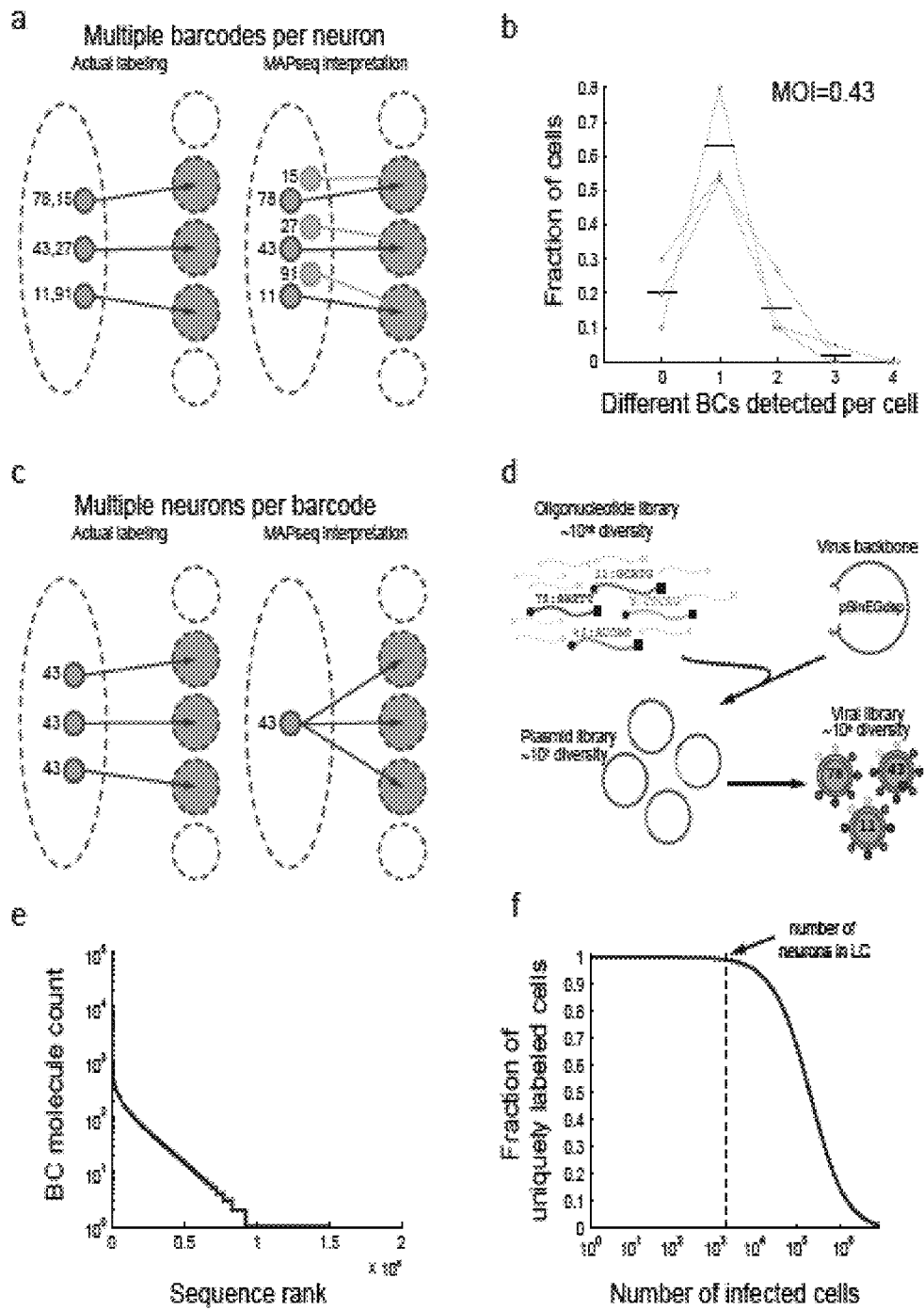
FIG. 2: Random labeling of neurons with a barcoded virus library can achieve unique labeling of many neurons. (a) Illustration of non-unique labeling of neurons where neurons are labeled with several barcodes and its impact on MAPseq readout. (b) Single cell isolation of barcoded neurons, followed by sequencing of their barcode complement, reveals a low chance of double infection. N=3 animals. Mean and individual datapoints are plotted. (c) Illustration of non-unique labeling where several neurons share the same barcode and its impact on MAPseq readout. (d) High diversity Sindbis virus libraries are produced by shotgun cloning random oligonucleotides into a plasmid followed by virus production. (e) The virus library used in this work has a diversity of ~$10^6$ different barcodes (BC). Based on this empirical barcode distribution, (f) it was determined that the virus library used is sufficiently diverse to uniquely label all of LC with low error rate.
Figure 3:
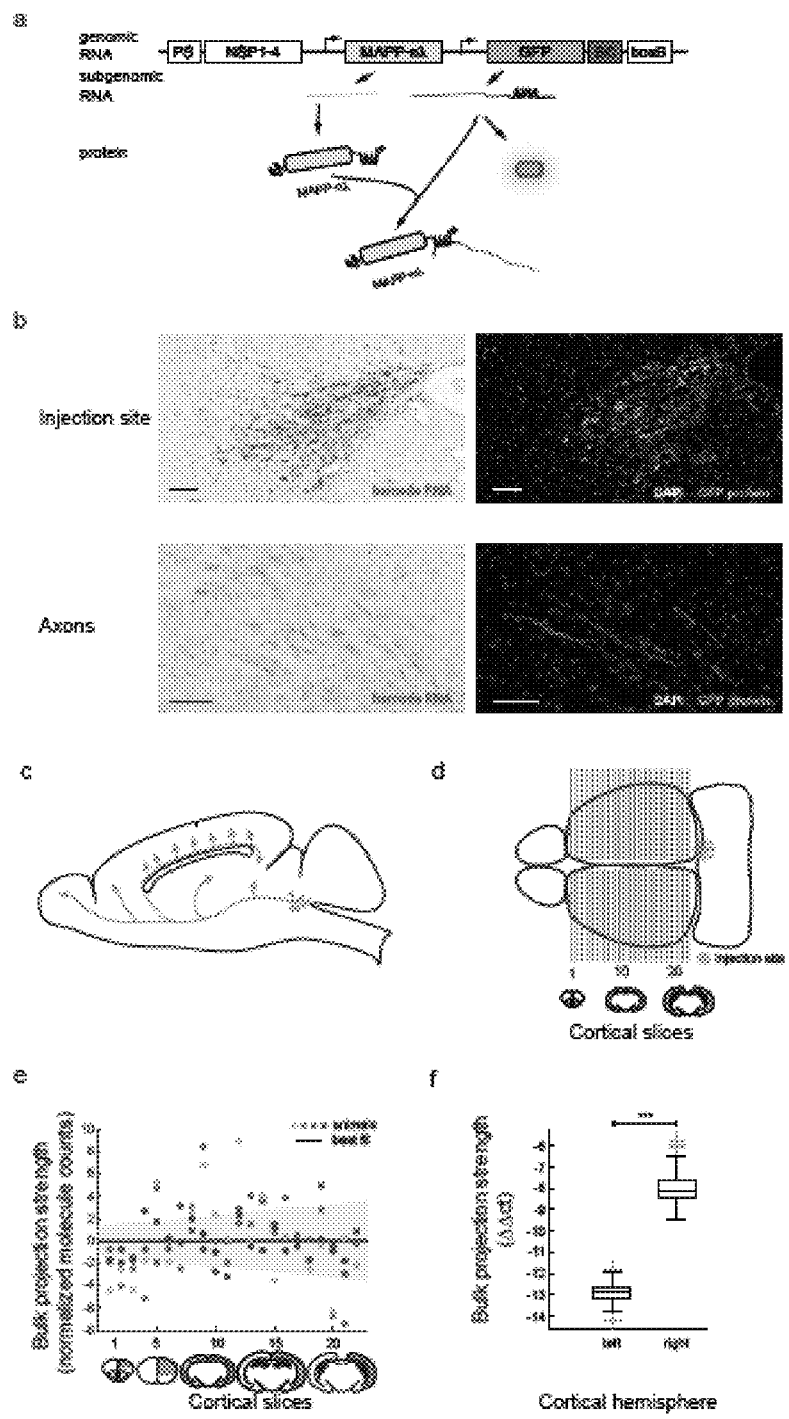
FIG. 3: Barcoded Sindbis virus can be used for projection mapping. (a) A dual promoter Sindbis virus, encoding GFP, barcodes and MAPP-nλ, is used to deliver barcodes to neurons. (b) Barcode mRNA labeling of LC neurons is comparable to GFP labeling of these neurons in an adjacent 6 µm slice both at the injection site (top) and in the axon tract (bottom). Scale bar=100 µm. Representative data from 3 animals. (c) Axons from LC project rostrally from the cell body, before changing direction and innervating cortex. LC axons that project to frontal cortices have accordingly traveled only about half as long as axons innervating visual cortex. (d) The right LC was injected with MAPseq virus and the cortex was dissected along the anterior-posterior axis as shown. (e) Bulk projection strength of LC to ipsilateral cortex as measured by barcode mRNA is independent of the anterior-posterior position of the cortical slice suggesting a uniform RNA fill of LC axons. N=4. (f) qPCR for barcode mRNA shows approximately 30× stronger LC projections to ipsi- than to contralateral cortex. N=2 animals and 21 cortical slices per animal.
Figure 4:
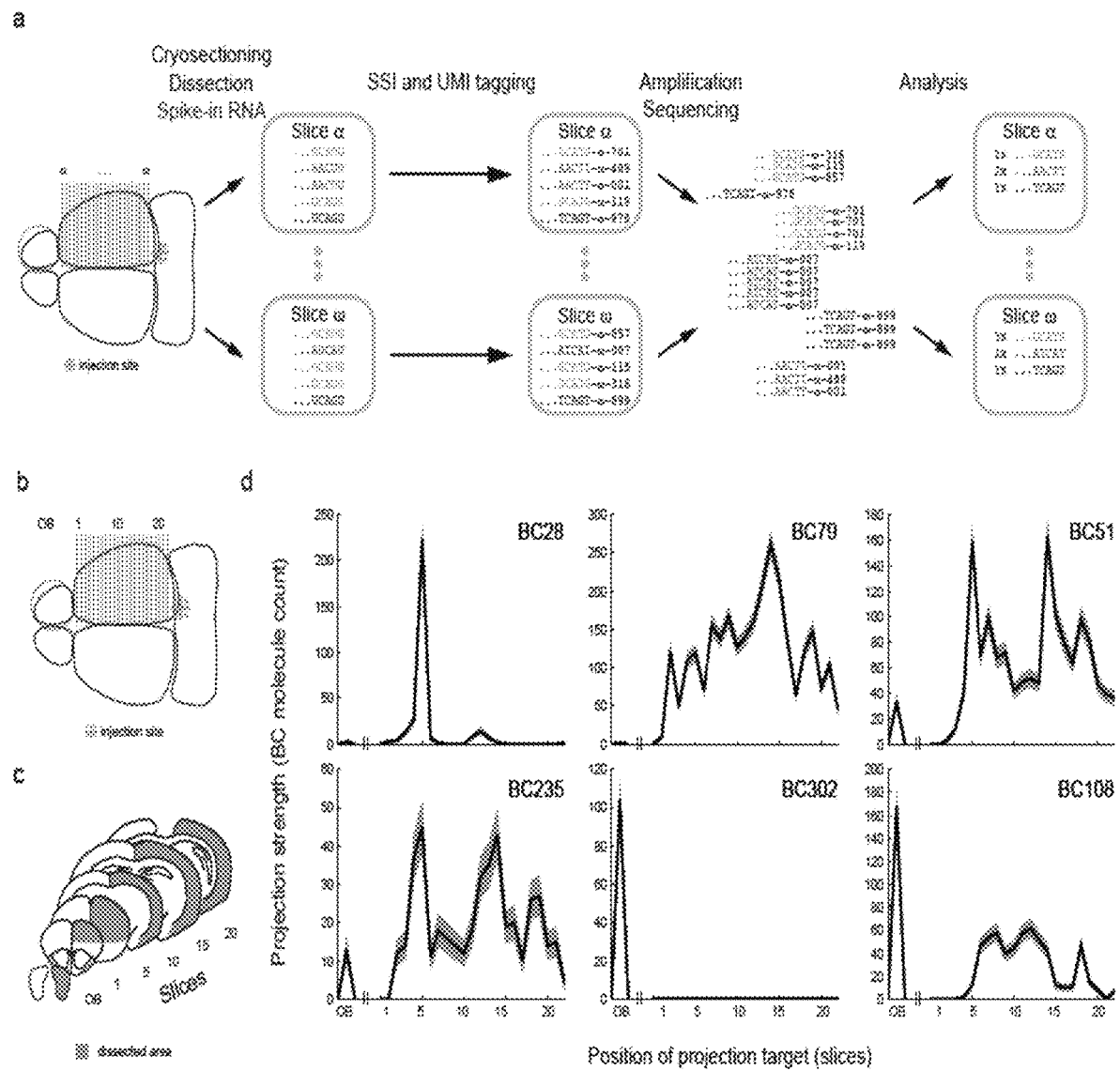
FIG. 4: MAPseq reveals large diversity of projections from LC. (a) Barcode mRNAs from target areas are sequenced as described (SSI=slice specific identifier, UMI=unique molecular identifier). (b,c) Barcodes from ipsilateral olfactory bulb and cortex show projection patterns (d) with single or multiple peaks in cortex and/or olfactory bulb. The shaded area indicates Poisson error bars given by the square root of BC counts per slice.
Figure 5:
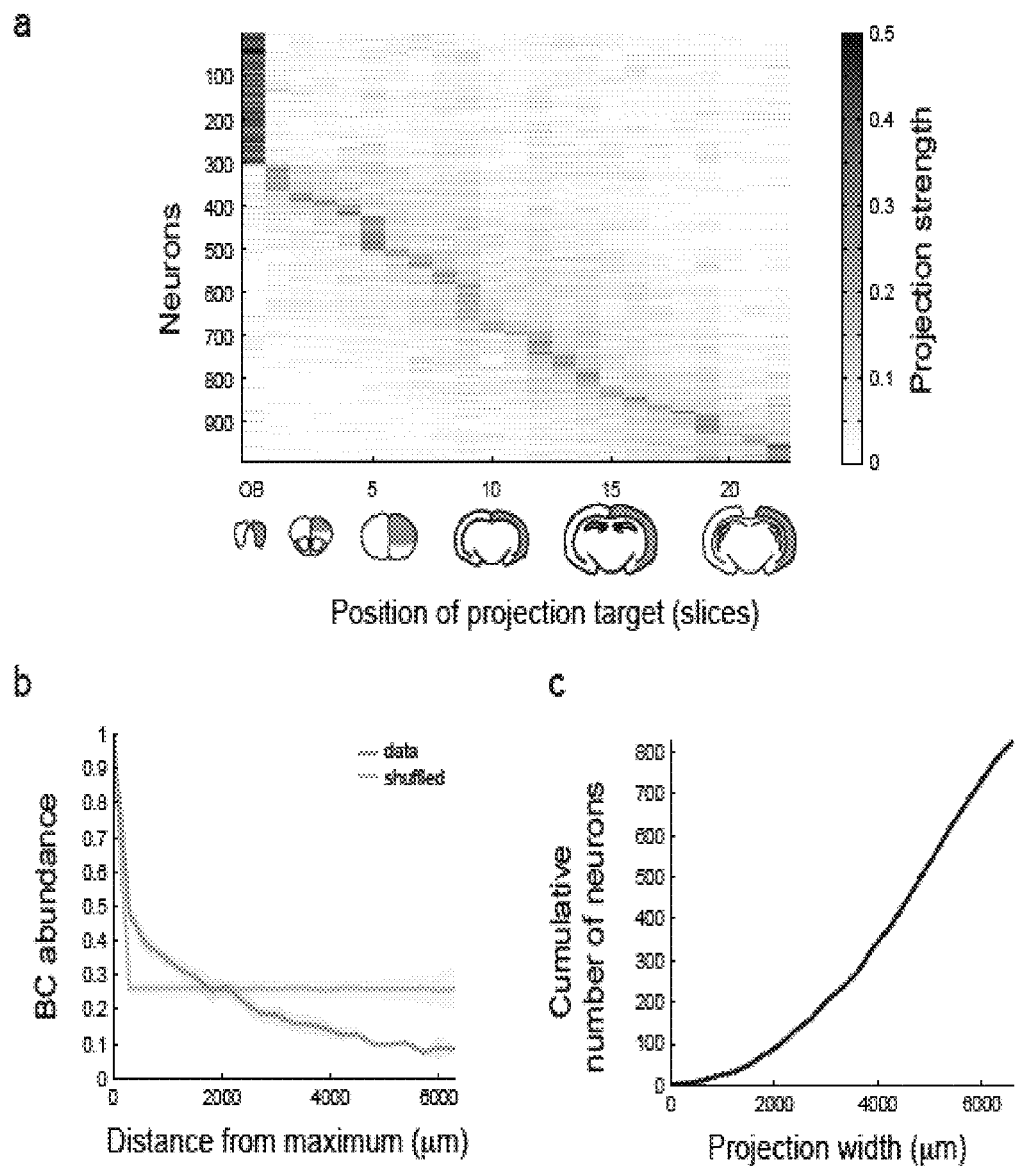
FIG. 5: (a) A heatmap of all 995 projection patterns from 4 animals shows a strong diagonal component after sorting by maximum projection site. Barcode abundances are normalized to sum to one across target areas and are colour-coded as indicated. (b) Average cortical drop-off rate from maximum for all barcodes shows a rapid drop-off and a structure that is different from the drop-off after randomly shuffling slices for all neurons. N=4. (c) Cumulative distribution of cortical projection widths indicates a broad low intensity innervation of cortex by individual LC neurons. (BC=barcode).
Figure 6:
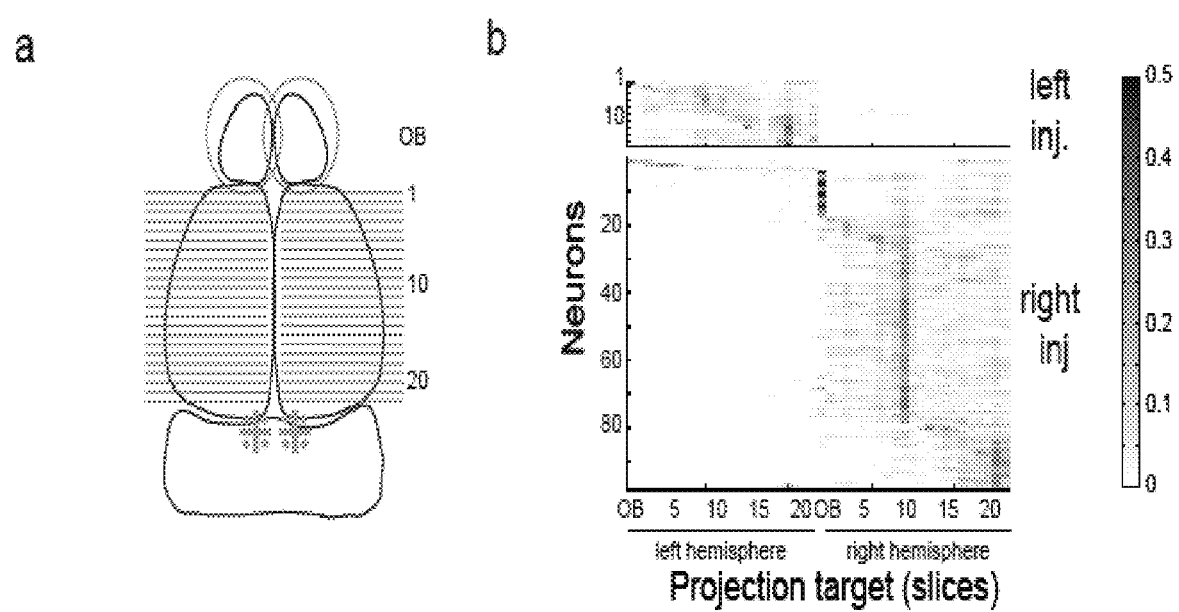
FIG. 6: MAPseq can be multiplexed to several injection sites. (a) Following bilateral injection of barcoded Sindbis virus into LC, left and right olfactory bulb and cortex were dissected as before. (b) Bilateral injections produce the projection pattern expected from unilateral injections. Differences in the number of neurons traced from the left and right LC arise from injection variability.
Figure 7:
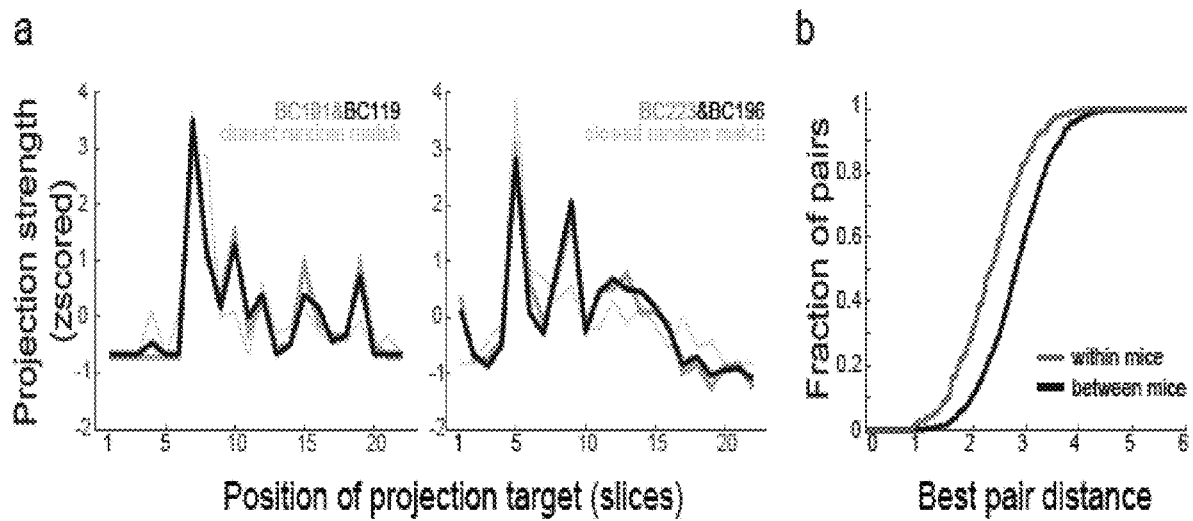
FIG. 7: MAPseq is a robust readout of single neuron projection patterns. (a) Two representative pairs of barcodes with projection patterns more similar than expected by chance for two distinct neurons. Their striking similarity suggests that MAPseq reads out single neuron projection patterns reliably. A closest match across animals is indicated in grey for comparison. (b) Cumulative distribution of distances between the beset barcode pairs within one animal and across animals. Representative data from one animal.
Figure 8:
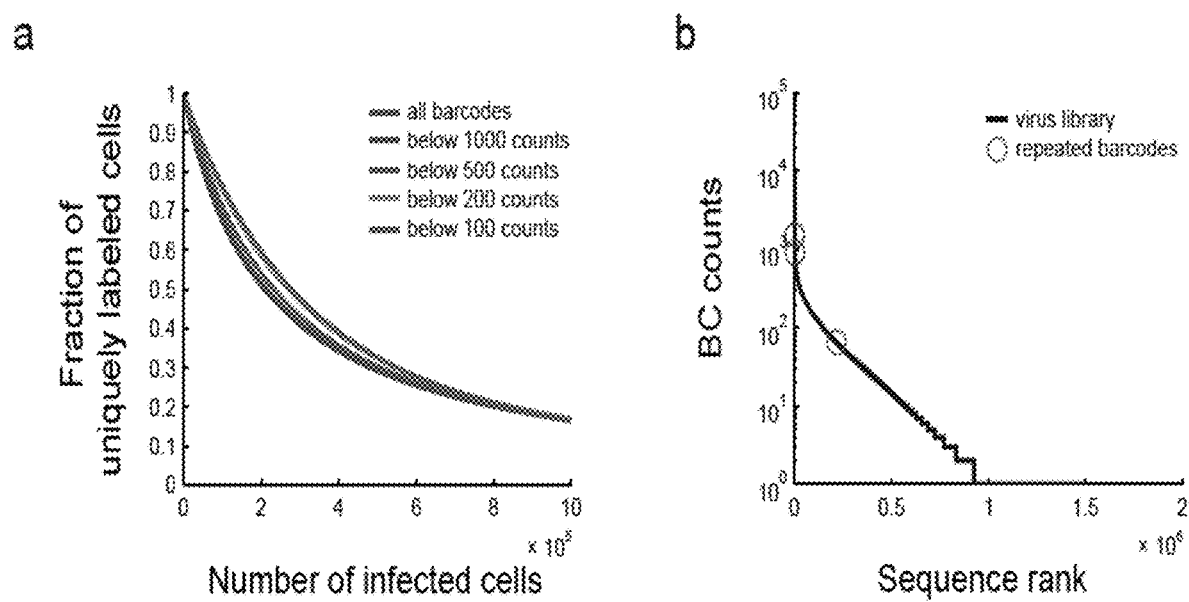
FIG. 8: Diversity of virus library is sufficient to uniquely label many cells. (a) The number of cells that can be uniquely labeled using our virus library does not change dramatically when overrepresented barcodes from the library are bioinformatically removed. The legend indicates which barcodes are still considered for labeling. (b) Position of the three barcodes that were traced in more than one of four animals. Two of the three are highly abundant in the virus library.
Figure 9:
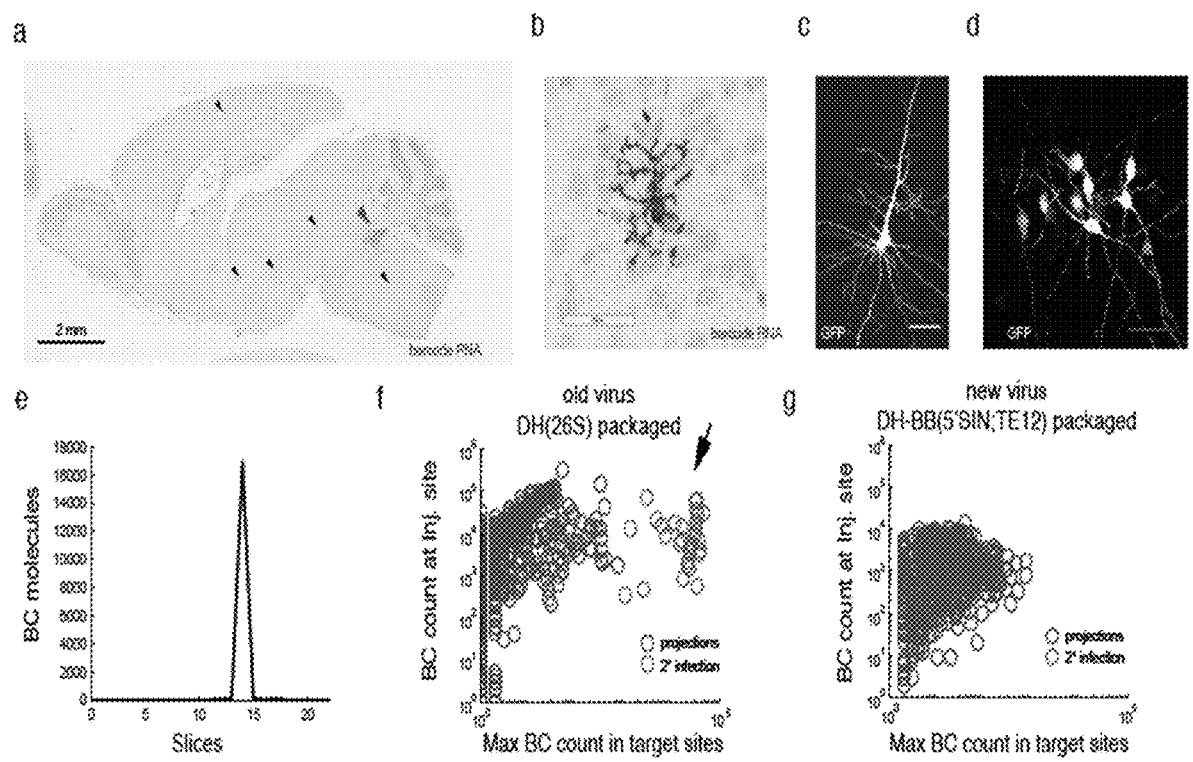
FIG. 9: The replacement of the conventional packaging system, DH(26S)5' SIN, with a modified packaging system we developed, DH-BB(5' SIN;TE12ORF), largely eliminates infection of cells distal to the injection site. After injection of conventionally packaged virus, (a,b) in situ hybridization for barcode mRNA labels cells far away from the injection site. Pink arrow=primary injection site; black arrows=secondary infection. (c,d) Similarly, GFP positive cells or clusters of cells far away from the injection site can be detected after injection of conventionally produced virus. Scale bar=50 µm. (e) MAPseq data produced using DH(26S) 5' SIN packaged virus shows spurious barcodes with extremely high abundance in a single target site only ("spikes"), which arise from barcodes expressed in cortical somata secondarily infected by propagation of viral particles from the axons of infected LC neurons. (f) Expression levels of these high abundance barcodes are comparable to that of barcodes in the injection site. (g) Changing the packaging system to the new DH-BB(5' SIN;TE12ORF) produces a propagation incompetent Sindbis virus and eliminates these high abundance barcodes. All MAPseq results described in this manuscript made use of this new virus.
Figure 11:
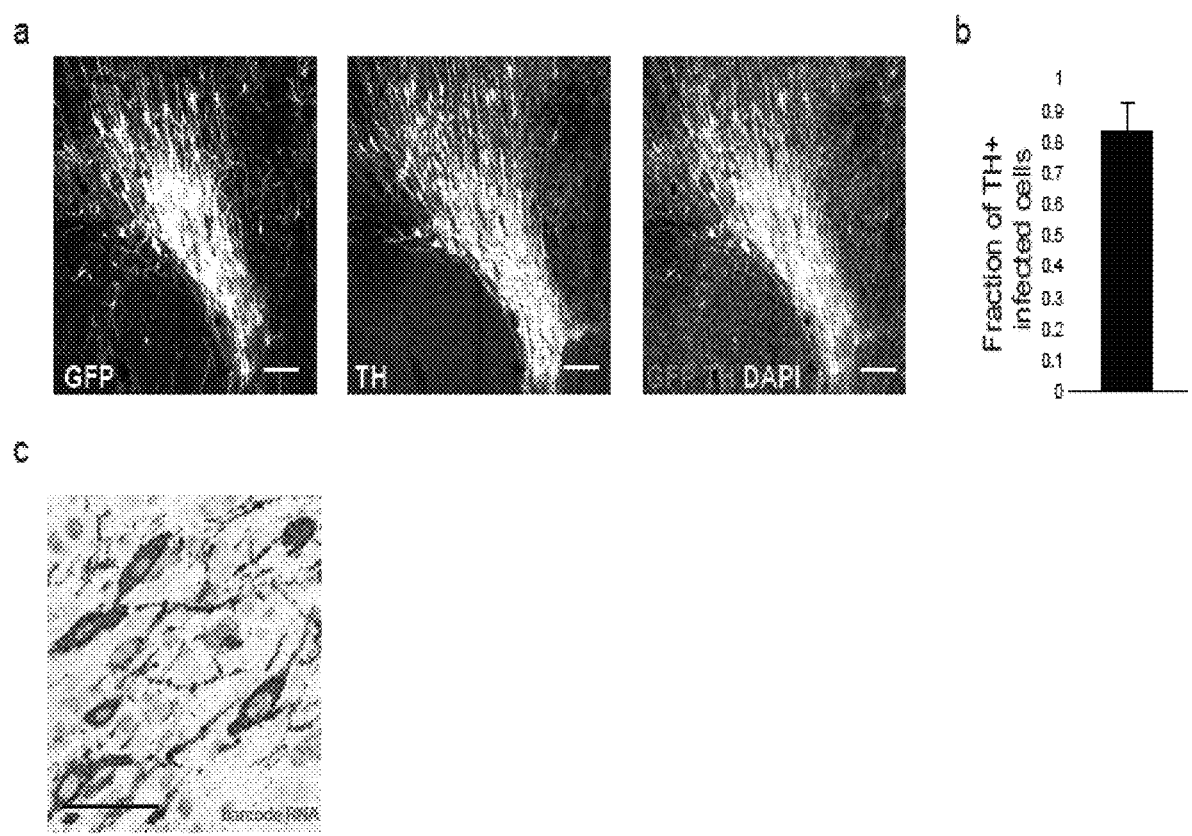
FIG. 11: Stereotaxic injection of Sindbis virus reliably infects LC and fills cell bodies and axons with barcode mRNA. (a) Maximum z-projection of a representative Sindbis injection shows excellent overlap with the TH-stained LC, confirming successful stereotactic targeting of the nucleus. Scale bar=100 µm. (b) Quantification of the fraction of infected cells that are also TH+, confirms reliable targeting of LC by streotactic injection. N=6. (c) RNA in situ of barcode mRNA showing good fills of cell bodies at the injection site. Scale bar=50 µm.
Figure 17:
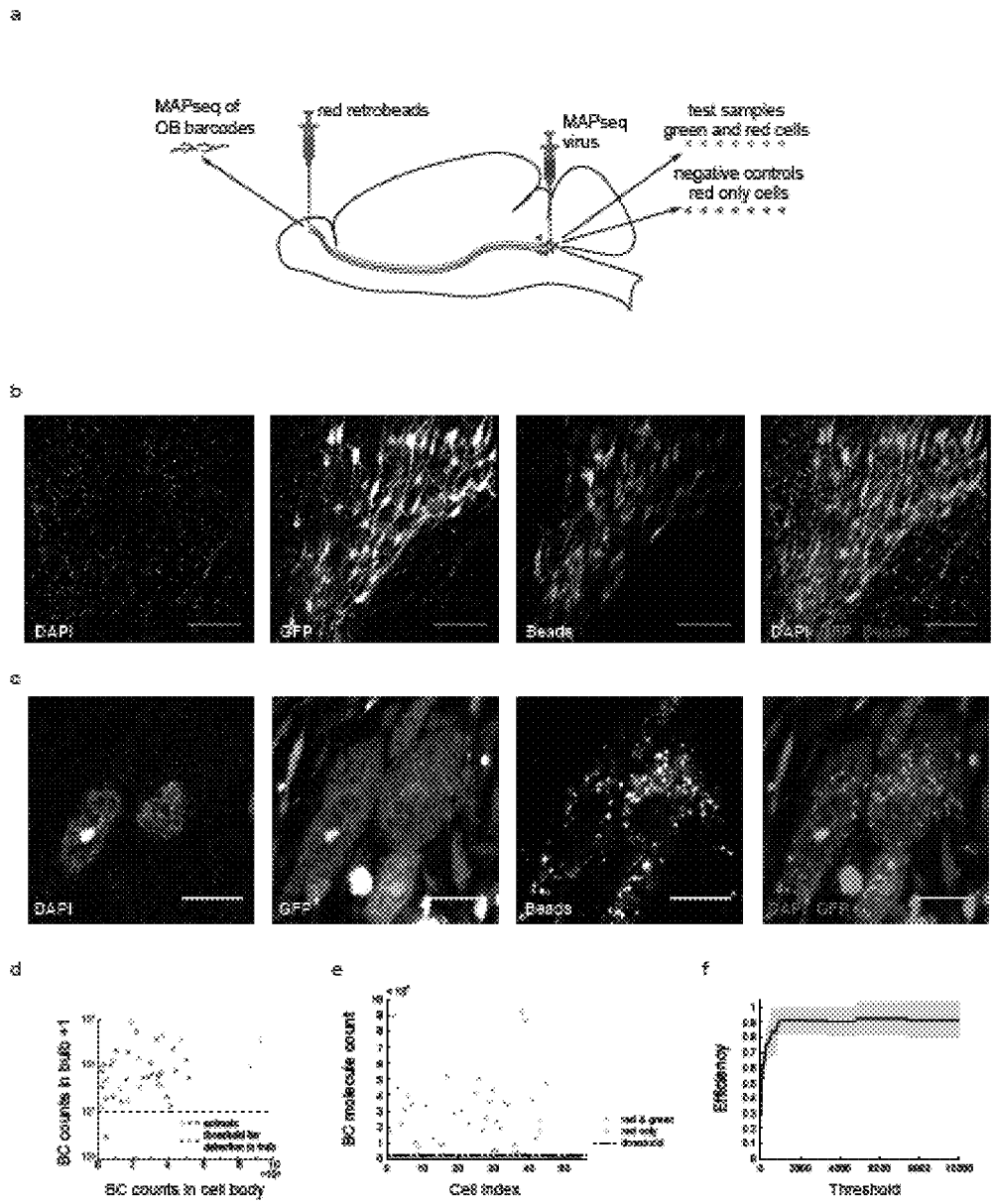
FIG. 17: Sequencing of single LC cells reveals low MOI and high MAPseq efficiency. (a) Overview of the experimental design. Red Lumafluor retrobeads label bulb projecting cells in LC. Barcodes present in these cells should also be present in the bulb. (b) overview image of LC, showing bead and GFP labeling of cells. Scale bar=100 µm. (c) Detailed image of retrobeads and GFP labeled cells. Scale bar=10 µm. (d) Scatter plot showing the relationship of barcode abundance in the olfactory bulb to barcode abundance in individual cells. The dashed line indicates the minimum barcode abundance in the bulb chosen as detection threshold. (e) Scatter plot of abundance of all barcodes found in the sequenced single cells for both bead and Sindbis labeled cells (n=45 from 3 animals, green) and negative control cells (bead labeled only; n=9 from 3 animals; red). Dotted line indicates the height of the most abundant barcode from red only cells, the threshold chosen to distinguish real from artefactual barcodes. (f) MAPseq efficiency as a function of an increasingly stringent noise threshold. The MAPseq efficiency estimate is not very sensitive to changes in the threshold value. Shaded area indicates s.d. across animals.

| Number of animals | Manipulation | Figures based on these animals |
|---|---|---|
| 2 | Right LC injection with MAPseq virus; dissection of right and left cortex; qPCR of barcode RNA | FIG. 3f |
| 1 | Bilateral LC injection with MAPseq virus; dissection of right and left cortex and olfactory bulb; qPCR and sequencing of barcode RNA | FIG. 6 |
| 3 | Right LC injection with MAPseq virus and retrobeads injection into right olfactory bulb; single cell isolation from LC | FIG. 2b, 17 |
| 3 | Right LC injection with DH(26S)5'SIN packaged MAPseq virus and dissection of olfactory bulb and sequencing of barcode RNA | FIG. 9, 18 |
| 6 | Right LC injection with DH(26S)5'SIN packaged MAPseq virus. TH staining of LC and quantification of overlap and count of TH+ neurons | FIG. 11 |
| 3 | Right LC injection with MAPseq virus; ISH for barcode RNA and IF for GFP protein | FIG. 3b, 11c |

Example 1. Application of MAPseq to the Locus Coeruleus

As a proof-of-principle, MAPseq was applied to the locus coeruleus (LC), a small nucleus in the brainstem that is the sole source of noradrenaline to the neocortex (Foote and Morrison, 1987). Early bulk tracing experiments revealed that the LC projects broadly throughout the ipsilateral hemisphere, leading to the view that the LC broadcasts a generalized signal that modulates overall behavioral state (Foote and Morrison, 1987; Foote et al., 1983; Loughlin et al., 1982; Waterhouse et al., 1983). This view has recently been supported by more sophisticated retrograde bulk tracing experiments, which reinforce the view that individual LC neurons project throughout the entire ipsilateral hemisphere (Schwarz et al., 2015). However, other recent reports have challenged this view. Using double retrograde labeling methods, these experiments uncovered separate populations of LC neurons projecting to different areas of cortex (Chandler et al., 2014; Chandler and Waterhouse, 2012), thus raising the possibility that the LC exerts differential control over different cortical areas. To resolve this controversy, MAPseq was applied to LC to obtain a large number of projection patterns at single neuron resolution.

In what follows, the feasibility of MAPseq is first established. The theoretical and practical constraints of randomly labeling large numbers of neurons with a viral library of barcodes are examined and it is shown that long-range projections of neurons can be determined using barcode RNAs. MAPseq is applied to LC and it is found that individual neurons have strong projections to preferential targets in cortex and the olfactory bulb (OB), with broad but weak projections to large areas of cortex. MAPseq is multiplexed to two injections in the same animal and finally the false positive and negative rates of our method are investigated.

Unique Labeling of Neurons with Barcodes

In traditional single-neuron tracing, the main challenge to multiplexing is the low diversity of labels (e.g. fluorophores or enzymes) available to disambiguate individual neurons. To overcome this challenge, MAPseq labels neurons with short, random RNA barcodes. Ideally, each labeled neuron should have exactly one unique barcode. Here the factors that could lead to deviations from this ideal scenario are considered: (i) more than one barcode per neuron (multiple labeling); and (ii) more than one neurons per barcode (non-unique or degenerate labeling). As discussed below, deviations resulting from multiple labeling are much less of a concern than those resulting from degenerate labeling.

A neuron may express more than one barcode if it is infected by more than one viral particle. Such multiple labeling will lead to an overestimate of the number of neurons identified, but will not distort the projection patterns recorded for individual neurons (FIG. 2a). Furthermore, even estimates of the relative abundances of different neuronal classes will, on average, be accurate. Assume for example that two neurons A and B are each labeled with 10 different barcodes. In this scenario, MAPseq will discover 10 instances of neuron A and 10 of B; but even though the absolute number of neurons is incorrect, the facts that neurons A and B have distinct projection patterns, and that these patterns occur in a 1:1 ratio, are accurately inferred (Example 2). Thus multiple labeling will not, on average, lead to mischaracterization of neuronal classes or of their relative frequency.

Nevertheless, to simplify the interpretation of MAPseq, the multiplicity of infection (MOI) was minimized by titrating the concentration and volume of virus injected. To estimate the MOI, individual neurons were isolated and the barcodes within each neuron were sequenced. On average, infected LC neurons contained 1.2+/−0.1 barcodes each, implying MOI of 0.43 (FIG. 2b). Only 21+/−11% contained more than one barcode.

The second deviation from the ideal scenario is non-unique labeling. If two neurons share the same barcode, then MAPseq interprets this as a single neuron whose projection pattern is given by the union of the projection patterns of the two infected neurons (FIG. 2c). The probability that two neurons are infected by the same barcode depends on the number of infected cells relative to the number of available barcodes. Trivially, if the number of infected cells is larger than the number of available barcodes, unique labeling of all neurons cannot be achieved. Conversely, if the number of available barcodes is much higher than the number of infected cells, every neuron will be labeled with a different barcode purely by chance.

To determine where we are relative to these two extremes, we quantified the number of cells in LC and counted 1985+/−132 (N=6 animals) neurons expressing tyrosine hydroxylase, a noradrenergic marker. This number is well below the theoretical diversity of a library of 30-nucleotide barcodes ($\sim 10^{18}$) suggesting that under ideal circumstances unique labeling is certain. In practice, however, the actual diversity of the library is limited by bottlenecks in plasmid and viral generation (FIG. 2d). Assuming that all barcodes are equally abundant in the library, the expected fraction F of uniquely labeled neurons is:

$$F=(1-(1/N))^{k-1}$$

where k is the number of infected neurons, and N is the barcode diversity (see Example 3). Thus if k=1000 LC neurons were infected with a library of diversity of N=$10^6$, on average 99.9% of all neurons would be labeled uniquely. Although in principle overrepresentation of a subset of barcodes in the library reduces the effective diversity, sequencing of the viral library (FIG. 2e) revealed that in practice these deviations had only a minor effect. Thus, under the conditions used in this example, the vast majority (>99%) of neurons will be uniquely labeled (FIG. 2f; Example 2; FIG. 8a).

A second more empirical approach was used to estimate the extent of degenerate labeling. Since the same viral library was used to infect neurons in different animals, barcode sequences found in more than one animal represent degeneracy. We therefore looked for overlap in the recovered barcodes from four independent injections of the same virus library. Out of the 992 unique barcodes used for projection mapping, only three barcodes were present in more than one animal, and no barcode was present in more than two animals. Moreover, two of the three repeated barcodes were among the most abundant barcodes in the virus library (FIG. 8b), and would thus be expected a priori to have the highest probability of double labeling. This analysis provides an independent confirmation that the error rate due to non-unique labeling by the barcode library is very low.

Using RNA to Trace Neurons

Traditional neuroanatomical tracing methods rely on filling neurons with dyes or proteins, so that neural processes can be resolved by microscopy. An implicit assumption of these techniques—albeit one that has rarely been rigorously tested—is that the tracer fills the neuron abundantly and uniformly, so that the strength of the signal corresponds to the quantity of labeled neural process, independent of distance from the soma. Here, two strategies were used to maximize the abundance and uniformity of barcode mRNA in distal processes.

First, we engineered a protein, which is denoted MAPP-nλ, to facilitate transport of barcode mRNA into axon terminals. To generate MAPP-nλ we began with pre-mGRASP, a protein engineered to localize at the presynaptic terminal due to fusion with trafficking signals from an endogenous presynaptic protein (Kim 2011). Four copies of an nλ domain (Daigle and Ellenberg, 2007) were then inserted on the cytoplasmic domain of mGRASP. The nλ domain is a 22 amino acid peptide ligand derived from the phage $\lambda_{N22}$ which binds to a 15-nt RNA hairpin, termed boxB, with very high affinity ($K_d$=22 nM). Four copies of the boxB sequence were added to the mRNA barcode.

Figure 10:
FIG. 10: Barcode Structure. (a) Differences in the sequence of viral barcodes and spike-in RNA allow easy discrimination of the two. (b) Structure of the final sequencing amplicon.
Figure 20:
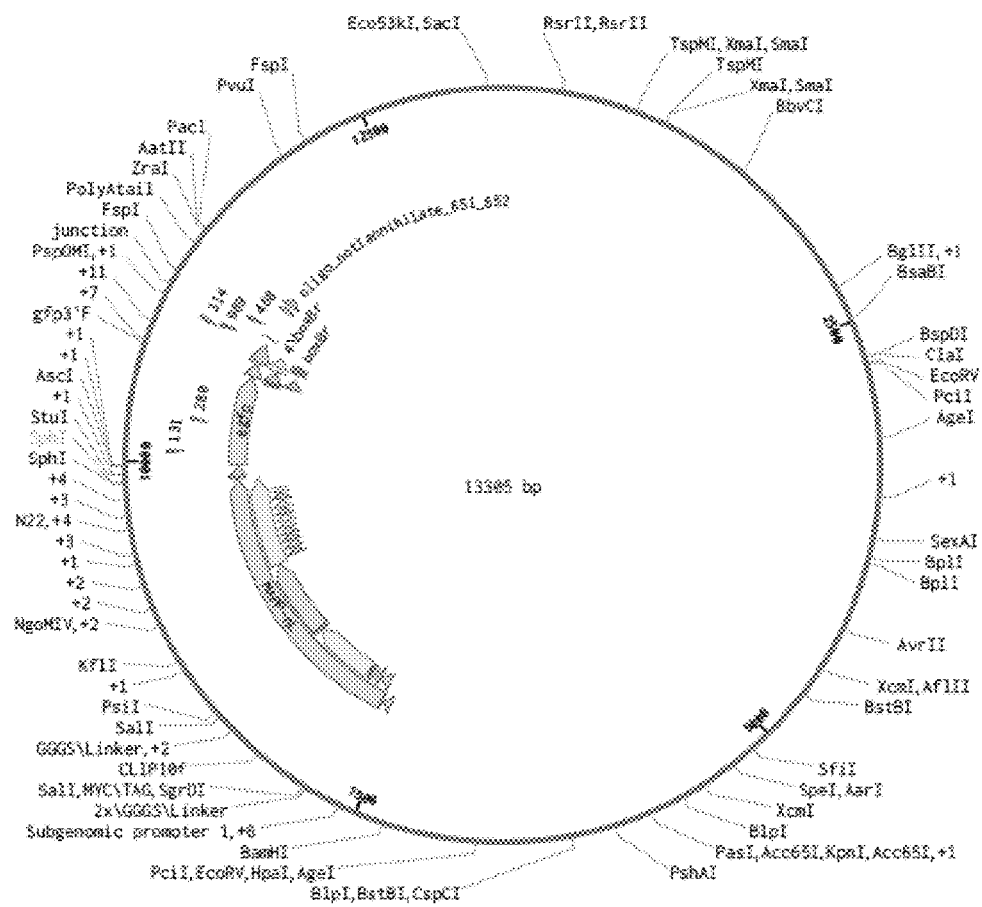
FIG. 20: Vector map of modified pSinEGdsp Sindbus virus construct which expresses MAPP-nλ and labels neurons with unique barcoded nucleic acids.
Figure 21:
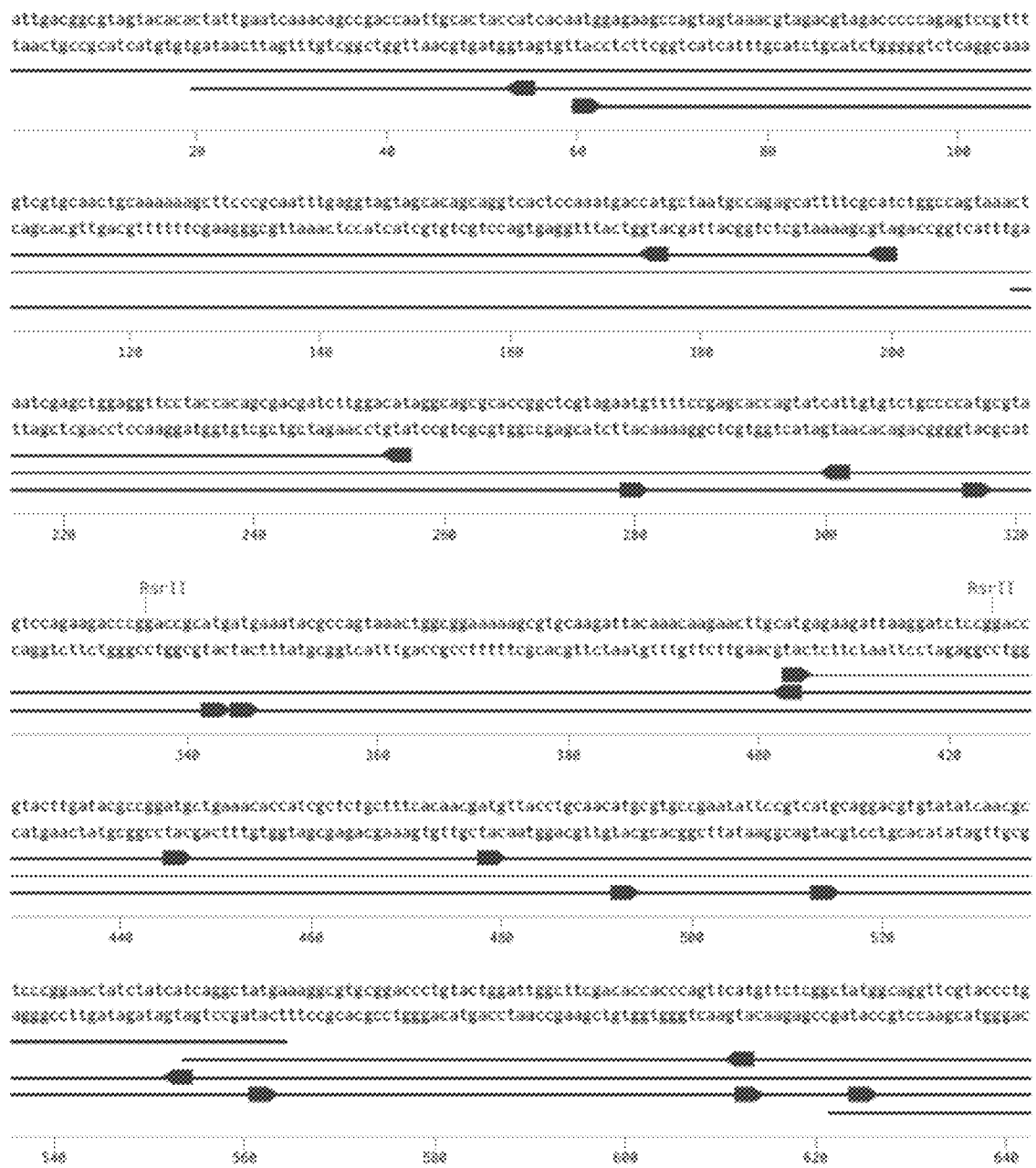
FIG. 21: Annotated sequence of vector map of modified pSinEGdsp Sindbus virus construct shown in FIG. 18.

Second, recombinant Sindbis virus was used, which can rapidly achieve very high expression, to deliver the barcode mRNA (FIG. 3a; Example 3). We used a novel Sindbis packaging system which, unlike previous systems, is both neurotropic and propagation incompetent (Kebschull et al., 2015) (FIG. 9). A dual promoter virus was used to generate two subgenomic RNAs. The first encodes a random 30-nt barcode, as well as the boxB sequence, downstream of a GFP marker (FIG. 3a; FIG. 10; FIG. 20; and FIG. 21). The other RNA encodes the MAPP-nλ protein. It is reasoned that by combining these two strategies, although each of them should be effective to localize barcode mRNA to axons independently, maximizes the ability to reliably detect barcode mRNA in distal processes.

Barcoded virus was injected into right LC (FIG. 11) and barcode localization was examined by in situ RNA hybridization 44 hours after injection. Robust barcode mRNA localization in the soma and neuronal processes was observed, in a pattern similar to that of co-expressed GFP (FIG. 3b). This suggested that barcode mRNA could effectively fill local neuronal processes.

The particular anatomy of LC projection neurons was exploited to determine whether the barcode mRNA fills distal neuronal processes uniformly. LC neurons that project to cortex send their processes all the way to the rostral end of the brain, before changing direction and moving caudally to innervate cortical areas (FIG. 3c). Axons that project to visual cortex are therefore approximately twice as long as those that project to frontal cortices. From bulk tracing studies it is known that LC innervation is homogeneous along the rostro-caudal axis (Schwarz et al., 2015; Waterhouse et al., 1983). Thus if barcode mRNA was not efficiently transported to distal processes, it would be expected to find more barcode mRNA in rostral regions of cortex. To assess this, barcoded virus was injected into LC. 300 μm coronal slices of the entire cortex were then cut (FIG. 3d) and the amount of barcode mRNA from each ipsilateral and contralateral slice was quantified. Consistent with previous results using GFP and other tracing methods (Schwarz et al., 2015; Waterhouse et al., 1983) it was found that approximately uniform projections throughout the ipsilateral cortex (p=0.972 vs. constant model; FIG. 3e); in particular, no evidence that distal processes were more weakly labeled than proximal processes was found. Also consistent with previous results, much weaker (30.6-fold less; $p=4\times10^{-31}$ paired student's t-test) projections to the contralateral cortex (FIG. 3f) were observed. As with conventional GFP tracing, MAPseq does not distinguish between synaptic connections and fibers of passage. These results suggest that barcode mRNA fills distal and proximal process with about equal efficacy, so that the amount of barcode mRNA can be interpreted in the same way as fluorophores or dyes in conventional tracing studies.

Barcode RNAs Sequencing Reveals Diverse Single Neuron Projection Patterns

Figure 12:
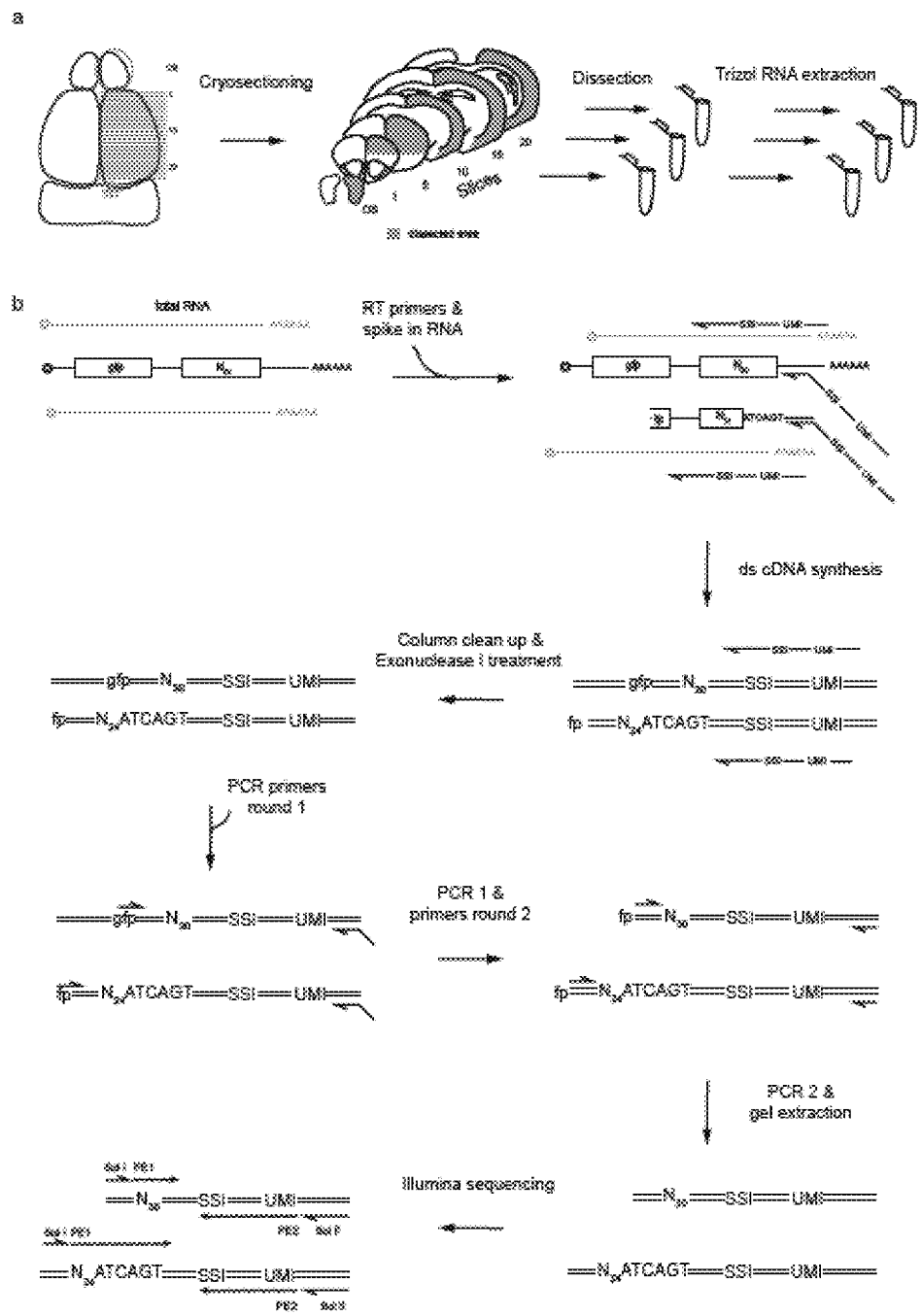
FIG. 12: MAPseq workflow. (a) A flash frozen brain is cryosectioned and areas of interest are dissected out. Total RNA from every area is then extracted individually. (b) A known amount of spike-in RNA and RT primers containing unique SSI and UMIs are added to the total RNA from every area. Double stranded cDNA is produced and leftover RT primers are digested using Exonuclease I to avoid UMI containing primers to participate in subsequent PCR reactions. Two rounds of nested PCR are performed, bringing in the PE2 sequencing primer binding site and P7 sequence as 5' overhangs of the reverse primer. After gel extraction, the amplicons are ready for Illumina sequencing.
Figure 13:
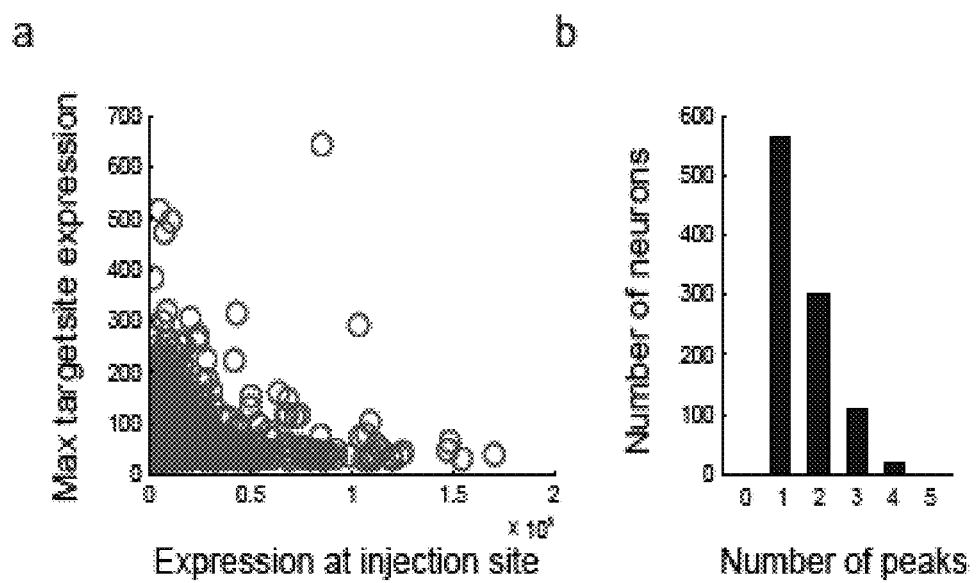
FIG. 13: Aggregate projection of MAPseq traced neurons reproduces homogeneous bulk projection, but individual projection patterns are non-homogeneous. (a) There is no correlation between the expression level of a barcode at the injection site and its maximum projection strength to a target area. (b) Histogram of the number of detected peaks for all MAPseq traced neurons. For peak definitions see Example 4.

The goal of MAPseq is to quantify the projection patterns of large populations of neurons in parallel. Therefore, a method to determine the amount each barcode in each target was developed (FIG. 4a). Forty-four hours after injection of barcoded virus into right LC, reverse transcription (RT) was performed on barcode mRNA extracted from dissected cortical target regions. To overcome distortions introduced during amplification (Kebschull and Zador, 2015), and to allow a precise count of barcode cDNA molecules, RT primers were designed to tag each individual barcode mRNA molecule with a random 12-nt unique molecular identifier (UMI). A 6-nt slice-specific identifier (SSI) was also added to allow multiplexing of samples within a single high-sequencing flow cell. These SSI-UMI-barcode cDNAs were then amplified, pooled and sequenced (FIG. 12). A conservative computational pipeline to minimize noise due to RNA contamination and to correct for sequencing and other errors was developed (Example 4). Finally, barcode abundance in the target areas was converted to a matrix of single neuron projection patterns.

In total, the projection patterns of 995 LC neurons from four animals were obtained. For each animal, the barcode mRNA extracted and amplified from 300 μm ipsilateral coronal cortical slices and from the olfactory bulb was analyzed (FIG. 4b,c). Because individual barcode mRNA molecules are tagged with a UMI before amplification, a precise quantification (subject to Poisson counting statistics; see Example 5) of the projection strength to each target was obtained. For each neuron, MAPseq therefore provides a reliable estimate of the projection pattern, i.e. of the relative projection strength to each target. For example, 223 copies of BC28 were recovered in slice 5, but none in slice 20, indicating that the projection strength to slice 5 is at least 200× higher than our detection floor (FIG. 4d). There was no correlation between expression level in the LC and in the projection strength to cortex, as would have been expected if differences across neurons were dominated by expression levels (R=−0.06; p=0.09; FIG. 13a).

Inspection of the projection patterns immediately revealed that, in contrast to the simplest prediction from conventional bulk tracing, single neurons did not project uniformly throughout the ipsilateral hemisphere. Instead, neurons projected in diverse and idiosyncratic ways to select target areas, innervating some areas hundreds of times more than others. Some neurons (e.g. BC28; FIG. 4d) showed specific projections to only a small part of cortex, whereas others (e.g. BC79; FIG. 4d) projected more broadly, or projected to multiple areas (e.g. BC51; FIG. 4d). Projections to the olfactory bulb appeared independent of projections to cortex, with some neurons projecting exclusively to the olfactory bulb (e.g. BC302; FIG. 4d) and others projecting to both (e.g. BC 108; FIG. 4d).

All traced neurons were sorted by their maximum projection (FIG. 5a). The maximum projections of individual LC neurons tile the entire cortex. Only in the aggregate do these projections recreate the apparently homogeneous LC innervation of cortex previously described by bulk methods (FIG. 2e). Consistent with previous results (Shipley et al., 1985), a considerable fraction (23+/−4.7%) of all mapped neurons projected to the olfactory bulb.

The average number of projection peaks per neuron was 1.6+/−0.8 (FIG. 13b), and the fall-off to half the maximum projection strength of individual neurons occurred on average in <300 µm (FIG. 5b). In addition to these tightly defined preferred projection targets, many neurons also had weaker but detectable projections to a considerable fraction of cortex, so that on average neurons projected to 65+/−23% of cortex (FIG. 5c).

Figure 14:
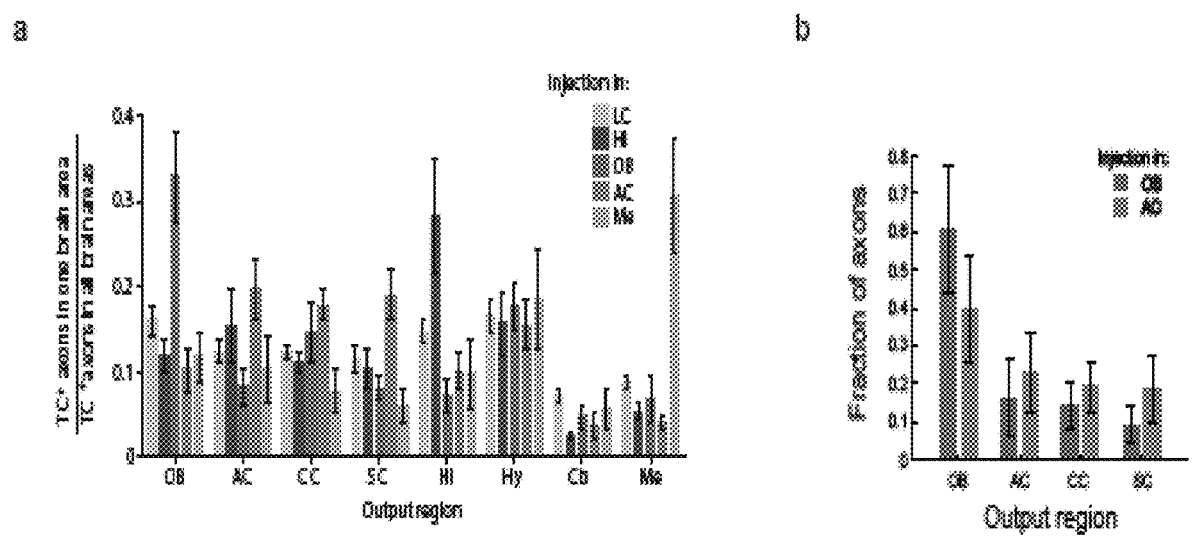
FIG. 14: Simulation of CAV-cre injection and axon tracing from MAPseq data reproduces the non-specific output pattern of LC neurons reported by Schwarz et al. (a) Reproduction of FIG. 4d of Schwarz et al. Briefly, Schwarz et al. injected retrograde CAV-cre virus into a number of areas including olfactory bulb and auditory cortex (AC), and cre dependent TVA-mCherry-AAV into LC. They then counted the number of mCherry labeled LC axons in a number of output areas and normalized the number of axons across all output areas. They could thereby quantify the projection strength of groups of LC neurons defined by their projection to the injection site and found that most groups of LC neurons project equally to all output areas. (b) Results of our MAPseq result based simulation of the experiment performed by Schwarz et al., plotted in the same way. Briefly, we simulated CAV-cre injections into olfactory bulb or auditory cortex (AC) by labeling barcodes that are present at more than 50 counts in either olfactory bulb or AC. The normalized counts of the labeled barcodes in slices containing the output regions were summed and the resulting projection strength across all output regions was normalized, thus mimicking the counting of labeled axons in output regions. In contrast to the idiosyncratic single cell projection pattern reported by MAPseq, this simulation recapitulates the findings of Schwarz et al., highlighting the importance of single neuron resolution in connectivity mapping. CC=cingulate cortex; SC=somatosensory cortex.

The fact that many neurons had a strong preferred cortical target, but also projected weakly to a much broader area, provides a way to reconcile apparently conflicting results about the specificity of LC projections. Experiments using TRIO, in which retrograde viral labeling is combined with anterograde tracing, concluded that LC neurons project nonspecifically throughout cortex (Schwarz et al., 2015). However, a neuron labeled retrogradely from a weak projection is indistinguishable from one labeled from a strong projection, so at the level of the population it may appear that projections are nonspecific. Thus, although the results of TRIO may naively appear to contradict those obtained by MAPseq at single neuron resolution, simulation demonstrate that there is no contradiction (FIG. 14).

MAPseq Scales to Several Injection Sites

Figure 15:
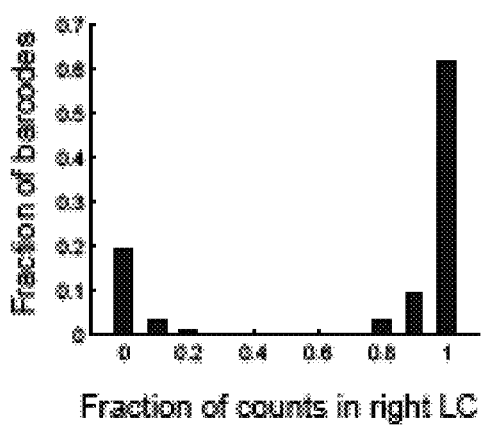
FIG. 15: MAPseq is multiplexable to multiple injection sites. (a) Histogram of the fraction of barcode counts in the right vs. left injection site across barcodes. Barcodes show strong abundance differences in the left and right injection sites allowing them to be assigned to one of the two sites.
Figure 16:
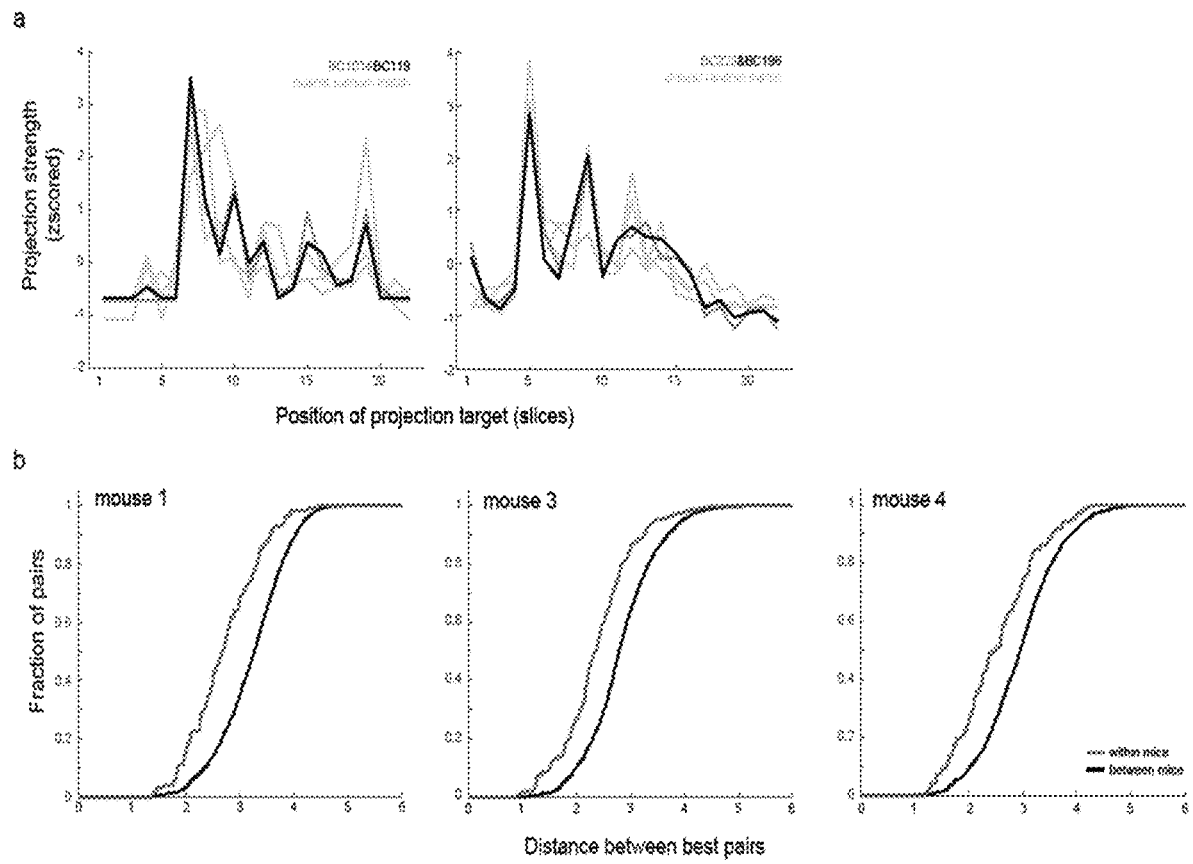
FIG. 16: MAPseq provides a robust readout of single neuron projection patterns. (a) The same example pairs of barcode profiles that are more similar than expected by chance as shown in FIG. 7a. In grey we indicated the five (5) best matches the barcode profiles across animals from five (5) independent samplings of the comparison animal. (b) Cumulative distribution function of distances of best barcode pairs within and across animals for animals 1, 3 and 4.

MAPseq can readily be extended to determine the projections of two or more regions in a single animal. As a proof-of-principle, virus was injected bilaterally into the LC (FIG. 6a). Each barcode was expressed predominantly in either the left or right LC (FIG. 15); barcode expression at the site contralateral to the injection, due to contralaterally projecting fibers and/or contamination, is much lower. Thus, each barcode can be reliably assigned to the appropriate injection site. As expected, parallel injections recapitulated the projection pattern observed with single injections (FIG. 6b). Multiplexing MAPseq to dozens of injections per animal may be feasible, reducing the labor and cost of brain-wide projection mapping efforts and eliminating the need to map data from multiple animals to an average reference brain (Oh et al., 2014; Zingg et al., 2014).

MAPseq is Precise

In the present work we sought to limit the number of neurons that were labeled with more than one barcode for reasons of interpretability. Nevertheless, double-infected neurons provide an opportunity to test the robustness of MAPseq projection mapping by effectively allowing for the independent measurement of the projection pattern of individual neurons several times. From single cell sequencing, it is estimated that infected neurons carry on average 1.2 different barcodes. Roughly 20% of all mapped neurons therefore are double labeled, which should manifest as different barcodes with very similar projection patterns. A number of barcode pairs within animals that have projection patterns that are remarkably similar were found, and indeed statistically significantly more similar than expected for projection patterns of two separate neurons (FIG. 7a, FIG. 16a). The total number of barcode pairs that is expected to come from double labeled neurons is able to be estimated by comparing the distributions of minimum pairwise distances between projection patterns within and across animals. These numbers indeed closely match our expectations from single cell sequencing (FIG. 7b, FIG. 16b).

MAPseq False Negative and Positive Rates

Like every experimental method, MAPseq is susceptible to both false negatives and false positives. First, we sought to relate the efficiency of MAPseq and thus its false negative rate to established neuroanatomical methods. MAPseq is conceptually closest to GFP-based methods (Oh et al., 2014; Zingg et al., 2014), in which a genetically-encoded fluorophore is expressed in a neuronal population, and fluorescence is detected in targets. The sensitivity and selectivity of such fluorophore-based methods depend on many factors, including expression level, imaging conditions, background fluorescence, etc. To our knowledge there has not been a rigorous and precise quantification of the sensitivity and selectivity of such methods, which would allow us to compute e.g. the probability of detecting a small axon for e.g. a given fluorophore expression level, etc; nor indeed is it clear how one would ground-truth such a quantification. Moreover, direct comparison of MAPseq and fluorophore-based methods on a section-by-section basis would be challenging because the optimal conditions for imaging and RNA extraction differ. Thus, a quantitative comparison of the efficiency of MAPseq with that of fluorophore-based methods was not attempted.

Instead, the efficiency of MAPseq was compared to that of another well-established method, Lumaflour retrobeads. Briefly, red retrobeads were injected into the olfactory bulb and MAPseq Sindbis virus into LC (FIG. 17). Retrobeads taken up by axons in the olfactory bulb are actively transported back to cell bodies and label bulb-projecting cells. Barcodes from infected LC cells that are labeled with retrobeads should therefore be present in the bulb. The fraction of barcodes recovered from retrobead-labeled LC neurons that are also detected in the olfactory bulb by MAPseq thus provides a neuron-by-neuron estimate of the MAPseq false-negative rate.

To calculate this measure of efficiency, we performed MAPseq on the olfactory bulb and sequenced the barcode complement of individual bead and Sindbis labeled LC cells by dissociating LC, and picking individual red and green cells using glass pipets (Sugino et al., 2006). Producing a single cell suspension from tissue slices involves digestion of the extracellular matrix and trituration of the tissue, which inevitably leads to breaking of processes and release of barcode mRNA into the bath. Given the very high expression levels of Sindbis virus, it is critical to obtain a noise distribution of barcodes present freely floating in the bath or in cell debris, as these barcodes will be collected alongside the labeled cells and sequenced, and will later be indistinguishable from cell resident barcodes except for their abundance. This noise distribution was measured by collecting cells that were GFP-negative, but were bead labeled. Since GFP-negative neurons do not express barcodes, any barcodes recovered from such cells represent contamination. The level of such contamination was used to establish the threshold for true barcode expression in intact isolated neurons.

45 neurons that were labeled with both GFP/barcodes and with red retrobeads were collected from the olfactory bulb, as well as 9 neurons labeled only with red retrobeads, to determine the background noise level of barcode expression. It was found that MAPseq efficiency is high: 91.4+/−6% (mean+/−std error) of all barcodes from cells that project to the bulb as determined by bead labeling also appear to project to the bulb by sequencing (across 3 animals; FIG. 17d). This estimate is robust over a large range of reasonable estimates for the level of background barcode contamination (FIG. 17f). It is therefore concluded that the false negative rate of MAPseq is 8.6+/−6%.

A false positive event in MAPseq is the detection of a barcode in a target area to which the neuron expressing the barcode does not project. There are two potential sources of false positives. First, a barcode that does indeed target this particular area might correctly be detected, but is perhaps mistakenly identified as a different barcode (due e.g. to sequencing errors). Alternatively, barcodes that arise from other samples (slices), or from outside sources, might contaminate the target sample. (A third kind of error, those arising from insufficient barcode diversity, might also be considered a special case of false positives, but are considered separately above in "Unique labeling of neurons with barcodes").

Due to the large combinatorial space of barcodes, it is exceedingly unlikely to mistake one barcode for another because of PCR or sequencing errors (see Example 4). Contamination, however, is a concern and needs to be quantified.

LC neurons project primarily to the ipsilateral hemisphere (Waterhouse et al., 1983), and only a small fraction of LC neurons project to both ipsilateral and contralateral cortex (Room et al., 1981). Quantifying the projection strength of neurons to the contralateral hemisphere relative to their projection to the ipsilateral hemisphere therefore provides an upper bound on the rate of contamination, and thus on the false positive rate of MAPseq. Note that samples from the ipsi and contralateral hemisphere were processed intermixed and out of order. Cross-contamination between samples from the ipsi and contralateral side should therefore be comparable to contamination between samples from the ipsilateral side only, and should be a good measure of overall contamination levels.

The MAPseq dataset of the bilaterally injected animal (FIG. 6) was used to calculate this upper bound to the false positive rate. Briefly, the ratio of the total number of barcode molecules detected in the contralateral hemisphere to the total number of barcode molecules detected in the ipsilateral hemisphere was calculated for all barcodes that projected more strongly to the ipsi than contralateral side (n=115). The mean ratio, and thus upper bound to the MAPseq false positive rate is 1.4+/−0.8% (mean+/−std error). Note that the assumption that LC neurons project only ipsilaterally is conservative; violations of this assumption would increase the estimated false positive rate. Thus it is concluded that MAPseq has a low false positive rate.

These results indicate that MAPseq provides both sensitive and reliable mapping of a large number of neurons.

Example 2. Labeling Neurons with Barcodes

In MAPseq neurons are randomly labeled with barcodes from a viral library to provide them with a unique identity. Ideally, every infected neuron would have a single, unique barcode. There are two deviations from this ideal scenario: (i) multiple neurons per barcode; and (ii) multiple barcodes per neuron. The implications of each are considered below.

Multiple Neurons Per Barcode

Multiple neurons per barcode, i.e. non-unique labeling, is problematic as it leads to incorrect results. Consider for example two neurons, A and B, that project to distinct cortical target areas. If by chance A and B are labeled with the same barcode (e.g. barcode 11), then MAPseq will return the merged projection pattern of A and B as the projection pattern of barcode 11. While this is indeed the projection pattern of barcode 11, it cannot be interpreted as the projection of a single neuron. Errors of this type can be avoided by using sufficiently diverse viral libraries, thereby minimizing the probability the same barcode will label two different neurons. This implies that the requisite diversity of the viral library depends on the number of neurons infected.

The mathematical problem is formulated here: Given a population of k neurons, labeled randomly from a pool of N barcodes, what is the probability that a given neuron will be uniquely labeled? This is closely related to the problem: What is the probability that a given barcode will appear in more than one neuron? These problems are related to the classical problem of drawing balls with replacement from an urn, where every ball corresponds to a barcode sequence, and the probability of drawing each ball is determined by the abundance of this barcode in the library.

First, consider a simplified case in which it is assumed that every barcode is equally abundant in the virus library, i.e. that the barcode probability distribution is uniform. What then is the expected number of neurons that share a barcode with at least one other labeled cell? If there are only two neurons A and B, then the probability of neuron B having the same barcode as neuron A is $P(A)=1/N$, so the probability that A's barcode is unique is $1-P(A)$. Generalizing to k infected neurons, the probability that A's barcode is unique is $(1-P(A))^{(k-1)}$, and the probability that it is not unique is $1-(1-P(A))^{(k-1)}$. As the expected value of a sum is the sum of its expected values, the expected number of non-uniquely labeled neurons is $$E(X)=k(1-(1-P(A))^{(k-1)}).$$

The fraction of uniquely labeled neurons F is then $$F=1-E(X)/k=(1-P(A))^{(k-1)}=(1-1/N)^{(k-1)}.$$

Similarly, the expected number D of barcodes used more than once is $$D=(k^2)/(2N),$$

where N is the number of barcodes and k is the number of infected cells, and it is assumed that $N \gg k$.

Now, let us consider the more realistic case, in which the distribution of barcode abundance is not uniform, so neurons are more likely to be labeled with some barcodes than others. To calculate the expected value of non-uniquely labeled neurons in this case, the reasoning above is generalized by including a sum over all barcodes, weighted by their probability. E(X) is then given by $$E(X)=k*\sum_{i=1}^{N}p_i(1-(1-p_i)^{k-1})$$

where $p_i$ is the probability of barcode $i=1 \ldots N$, k is the number of infected neurons and N is the total number of barcodes in the virus library.

To determine the empirical distribution of barcodes in the virus library, the genomic RNA of an aliquot of the previously described Sindbis virus was directly sequenced.

Sequencing was performed at sufficient depth to overcome Poisson sampling introduced by Illumina sequencing. After error correction, the absolute abundance of different barcode sequences is a direct measure of the barcode probability distribution (FIG. 2e). Despite error correction, there is a chance of including erroneous barcode sequences when counting barcodes that have a very low molecule count. Therefore, for all calculations a conservative threshold was chosen and at least 3 counts for barcodes were required in order to be included in the virus library. Based on this empirically determined distribution of barcode abundances, the fraction of uniquely labeled cells was calculated as a function of the number of infected cells (FIG. 2f). Simulations indicate that removing the most abundant barcodes have little effect on the capacity of the library to label neurons uniquely (FIG. 8a). These results indicate that the observed non-uniformity in the abundance of barcodes in the library does not substantially interfere with the capacity of the library to uniquely label large numbers of cells.

Example 3. Sindbis Virus

MAPseq requires that a propagation-incompetent virus be used for barcode delivery, i.e. after a neuron is infected with a particular barcode, the virus carrying this barcode should not propagate and spread to other cells. If the virus did propagate, barcodes would spread from cell to cell, and unique labeling of neurons by barcodes would break down as many neurons would now share the same barcode.

Initial Sindbis virus libraries prepared with the conventional helper construct DH(26S)5' SIN induced GFP labeling not only at the injection site, but also occasionally at sites far away from the primary site of injection (FIG. 9). Such distal labeling has previously been interpreted as retrograde infection (Furuta, 2001), however, it has been recently shown that it does not arise from retrograde spread but rather is due to secondary infection (Kebschull, 2015). Consistent with secondary spread, a subset of barcodes showed unexpectedly high expression levels in single target areas ("spikes"; FIG. 9e) when MAPseq was performed with barcoded virus packaged using the conventional helper construct. Indeed, the barcode expression level in these spikes is comparable to the expression level of the same barcodes at the primary injection site (FIG. 9f). These observations strongly suggested that the observed spikes originate from ectopically infected cell bodies that are labeled with the same barcode as a neuron at the injection site. Given the high diversity of the viral library, such double labeling is exceedingly unlikely to occur by chance if labeling were due to retrograde infection, but would be expected if the virus used propagated inside the brain.

Therefore, a new helper construct was designed, DH-BB (5' SIN;TE12ORF) (Kebschull, 2015), to eliminate secondary spread. When this modified helper construct was used, which minimized co-packaging, secondary infection was almost completely eliminated and we were unable to detect any more spikes by sequencing (FIG. 9g). Sindbis virus packaged by DH-BB(5' SIN;TE12ORF) thus fulfills the requirements for use in MAPseq. Viral libraries prepared with the modified helper virus were used in all subsequent MAPseq experiments.

Example 4. Bioinformatics

Raw MAPseq data consist of two .fastq files containing Illumina sequencing results, where paired end 1 covers the barcode sequence, and paired end 2 covers the 12 nt UMI and the 6 nt SSI (FIGS. 10 and 12). To convert these sequencing data into projection maps, the data is first preprocessed in bash before being analyzed in Matlab (Mathworks).

Preprocessing of Sequencing Data

Briefly, the fastq files were stripped of their quality information and the reads were trimmed to the relevant length. Paired end 1 and 2 were then merged into a single file. Each line of this file corresponded to a single read containing the 30 nt barcode, the 2 nt pyrimidine anchor (YY), the 12 nt UMI and the 6 nt SSI. The reads were de-multiplexed based on the SSI using the fastx_barcode_splitter tool and filtered to remove any ambiguous bases. The reads were then collapsed to unique sequences and sorted.

Next, a threshold of how many reads a sequence has to have in order to be considered for analysis was set. Selection of the threshold was guided by earlier work on the effect of PCR amplification during Illumina library generation on next generation sequencing data (Kebschull and Zador, 2015), where it was found that when amplifying a pool of unique barcode sequences by PCR the sequence rank profile of the Illumina results consists of a plateau of sequences with roughly equal read counts followed by a shoulder and a long tail. The tail of this distribution is formed almost exclusively by PCR errors. Therefore, in the MAPseq datasets a manually selected a minimum read threshold was selected to remove the tail of the sequence rank profile from the analysis. This avoids contamination of the dataset with large numbers of PCR and sequencing errors and simplifies subsequent error correction and analysis steps.

The remaining reads (30 nt barcode+YY+12 nt UMI) were collapsed after removal of the 12 nt UMI to convert reads into molecule counts. Note that any potential PCR or sequencing errors in the 12 nt UMI were ignored, which will lead to a slight, but uniform, overestimation of molecule counts as two copies of the same cDNA with an error in the UMI only will be counted as two distinct molecules rather than one.

Split of Barcodes from Spike-Ins

Spike-in molecules are barcodes of length 24 followed by the constant sequence ATCAGTCA, and are therefore easily distinguished from barcodes expressed from the virus (FIG. 10). As they carry different information, the uncorrected barcode data was split into spike-ins (perfect match to $N_{24}$ATCAGTCA) and virally expressed barcodes (no $N_{24}$ATCAGTCA sequence, but $N_{30}$YY) and processed separately.

Error Correction

A random barcode of 30 nt length has a potential diversity of $4^{30} \approx 10^{18}$ different sequences. If a relatively small number of barcodes is sampled from this enormous diversity, the chosen barcodes are likely to be very different from each other. Therefore many mutations to any given barcode are necessary to convert it into any other barcode of the chosen set.

This fact was exploited to correct errors in the sequenced barcodes. An all-against-all mapping of all barcode sequences with >1 counts, allowing up to 3 mismatches, was performed using bowtie. Here, bowtie was forced to output all possible alignments. A connectivity matrix of all barcode sequences was subsequently constructed, where bowtie alignments are the connections between sequences. Matlab was used to find all connected graph components, that is, all barcodes that mapped to each other. The molecule counts of each of the members of such a connected component were collapsed to the sequence of the most abundant member.

Low complexity sequences—a common artifact of Illumina sequencing—were removed by filtering barcodes with stretches of more than 6 identical nucleotides. Finally, all error corrected barcode sequences were compared to the error corrected barcode sequences found in the original virus library. Only those barcodes that had a perfect match in the virus library were kept for analysis.

Code for preprocessing of all MAPseq libraries can be found in preprocessing.sh and matlab_preprocessing.m. The viral library was processed using viruslibrary_preprocessing.sh and viruslibrary_matlabcode.m.

Analyzing the Projection Pattern

The described workflow results in a list of barcode sequences and their molecule counts in each target area and the injection site. Using Matlab, the barcode sequences in the injection site (reference barcodes) were matched with the barcode sequences in the target sites, constructing a barcode matrix of size [# of reference barcodes]×[# of target sites+# of injection sites] which then acts as the basis of all further analysis. Note that barcodes that appear in target areas and not the injection site ('orphans') are very rare and have low abundances, consistent with an interpretation of orphan barcodes as contaminants.

To exclude low confidence projection patterns from analysis, each barcode was required to have more than 100 counts in the injection site and at least one target area with more than 30 counts.

Code can be found in producebarcodematrix_unilateral.m and producebarcodematrix_bilateral.m.

Barcode Matrix Normalization

Raw barcode counts are very useful to survey the data available and to form intuitions about the mapped projection patterns. However, to compute summary statistics, the raw barcode matrix was normalized. First each target area was normalized by the number of unique spike-in molecules detected in each to normalize for varying RT, PCR or library making efficiencies. Then each area was normalized by the amount of β-actin per μl of total RNA (as measured by qPCR) to correct for varying tissue input and RNA extraction efficiencies. Lastly, all barcodes were normalized to sum to 1 across all target areas to correct for different expression levels of different barcodes.

Code for all analysis of the barcode matrix can be found in analyse_unilateralinjections.m and analyse_bilateralinjections.m.

Peak Finding

To summarize LC projection patterns, a number of criteria to define peaks for each barcode were set. First, peaks need be at least half as high as the maximal barcode count across all target sites. Second, peaks need to be separated by at least 3 slices, and third, peaks need to rise at least their half maximal height from their surroundings ('prominence'). Code used to find peaks can be found in detectpeaks.m.

Identification of Double-Infected Cells

In order to identify pairs of barcodes that originated from double-infected cells, we looked for projection profiles from individual mice that are more similar than expected for barcodes from different cells. Briefly, the minimum pairwise Euclidean distance of every barcode profile to any other barcode profile of a particular mouse ("within mouse") was calculated. A null-distribution was then constructed by calculating the minimum pairwise distances for every barcode profile from that mouse to a bootstrapped sample of barcode profiles obtained from the other three mice in this MAPseq dataset ("between mice"). Distances that appear in the "between mice" null-distribution result from the similarity of the projection profiles of different cells. Therefore, distances in the "within mouse" set lower than those explained by this null distribution suggest that the two barcode profiles are more similar than would be expected for two separate cells. The two barcodes that correspond to this low distance probably arise from a single double-infection cell. Accordingly, those barcode pairs were defined as originating from double-infected cells that had distances in the left tail of the null distribution subject to Bonferroni correction for multiple hypothesis testing.

To estimate the overall number of barcodes from double-infected cells in every animal, the point of intersection of the cumulative distribution of "within mouse" and "between mice" distances was calculated. The number of barcode pairs up to this point was taken as an estimate of the number of barcodes in double infected cells, which corresponds roughly to 2× the number of double infected cells.

Single Cell Analysis.

Code for analysis of single cells sequencing data can be found in preprocessing_singlecells.sh, matlab_preprocessing_singlecells.m and analyse_singlecells.m.

False Positive Rate.

Code for the calculation of the false positive rate can be found in analyse_bilateralinjections.m.

Example 5. Spike-in Recovery

To assess the efficiency of barcode recovery in MAPseq, a known amount of spike-in RNA (FIG. 10) was added into every sample (FIG. 4*a*, FIG. 12) and the number of distinct spike in molecules was quantified in the sequencing results. The ratio of the number of recovered spike-in molecules to the number of input molecules then is the probability of detection of any given barcode molecule.

Detection efficiencies are relatively constant across areas and animals (FIG. 19) and average to P(detection)=0.024 for target areas. This implies that when a barcode in an area is not detected, there are less than 123 barcode mRNA molecules present in that sample with a confidence >95%, as dictated by the negative binomial distribution.

Note that this measure of barcode detection probability is based on the efficiency of going from total RNA to sequencing results. It is blind to losses incurred during extraction of total RNA from tissue, such that the overall MAPseq detection efficiency is likely somewhat lower than estimated.

Example 6. Amino Acid Sequences which Encode Carrier Proteins Capable of Transporting Barcoded Nucleic Acids to Axon Terminals MAPP-nλ:
MPPSTSLLLLAALLPFALPASDWKTGEVTASRDHMVLHEYVNAAGITGGG

GSGGGGSVDEQKLISEEDLQFMDKDCEMKRTTLDSPLGKLELSGCEQGLH

RIIFLGKGTSAADAVEVPAPAAVLGGPEPLIQATAWLNAYFHQPEAIEEF

PVPALHHPVFQQESFTRQVLWKLLKVVKFGEVISESHLAALVGNPAATAA

VNTALDGNPVPILIPCHRVVQGDSDVGPYLGGLAVKEWLLAHEGHRLGKP

GLGGGGGSVDFQKASSIVYKKEGEQVEFSFPLAFTVEKLTGSGELWWQAE

RASSSKSWITFDLKNKEVSVKRVTQDPKLQMGKKLPLHLTLPQALPQYAG

SGNLTLALEAKTGKLHQEVNLVVMRATQLQKNLTCEVWGPTSPKLMLSLK

LENKEAKVSKREKAVWVLNPEAGMWQCLLSDSGQVLLESNIKVLPTWSTP

-continued

```
VQPMALIVLGGVAGLLLFIGLGIFFCVRYKYRNRDEGSSAPPLDGAGAGA
GAGAGAGGLATMDAQTRRRERRAEKQAQWKAANPPLDGAGAGAGAGAGAG
GLATMDAQTRRRERRAEKQAQWKAANPPLDGAGAGAGAGAGAGGLATMDA
QTRRRERRAEKQAQWKAANPPLDGAGAGAGAGAGAGGLATMDAQTRRRER
RAEKQAQWKAANPPLEPPLDGAGAGAGAGAGAGGLATPPSAYHVDESRNY
ISNSAQSNGAVVKEKQPSSAKSANKNKKNKDKEYYV*
CLAP-1x-nλ:
MYQRMLRCGADLGSPGGGSGGGAGGREALIWIVPLTLGGLLGVAWGEFEQ
KLISEEDLQFMDKDCEMKRTTLDSPLGKLELSGCEQGLHRIIFLGKCTSA
ADAVEVPAPAAVLGGPEPLIQATAWLNAYFHQPEAIEEFPVPALHHPVFQ
QESFTRQVLWKLEKVVKFGEVISESHLAALVGNPAATAAVNTALDGNPVP
ILIPCHRVVQGDSDVGPYLGGLAVKEWLLAHEGHRLGKPGLGVDGTASSL
```

-continued

```
GAHHIHHFHGSSKHHSVPIAIYRSPASLRGGHAGTTYIFSKGGGQITYKW
PPNDRPSTRADRLAIGFSTVQKEAVLVRVDSSSGLGDYLELHIHQGKIGV
KFNVGTDDIAIEESNAIINDGKYHVVRFTRSGGNATLQVDSWPVIERYPA
GRQLTIFNSQATIIIGGKEQGQPFQGQLSGLYYNGLKVLNMAAENDANIA
IVGNVRLVGEVPSSMTTESTATAMQSEMSTSIMETTTTLATSTARRGKPP
TKEPISQTTDDILVASAECPSDDEDIDPCEPSSGGLANPTRVGGREPYPG
SAEVIRESSSTTGMVVGIVAAAALCILILLYAMYKYRNRDEGSSAPPLDG
AGAGAGAGAGAGGLATMDAQTRRRERRAEKQAQWKAANLEPPLDGAGAGA
GAGAGAGGLATPPSAYHVDESRNYISNSAQSNGAVVKEMQPSSAKSANKN
KKNKDKEYYV*
```

Example 7. RNA Sequence of the Defective Helper RNA DH-BB (5' SIN;TE12ORF)

```
tatagATTGACGGCGTAGTACACACTATTGAATCAAACAGCCGACCAATTGCACTACCATCACAATGG
AGAAGCCAGTAGTAAACGTAGACGTAGACCCCCAGAGTCCGTTTGTCGTGCAACTGCAAAAAAGCTTC
CCGCAATTTGAGGTAGTAGCACAGCAGGTCACTCCAAATGACCATGCTAATGCCAGAGCATTTTCGCA
TCTGGCCAGTAAACTAATCGAGCTGGAGGTTCCTACCACAGCGACGATCTTGGACATAGGCAGCGCAC
CGGCTCGTAGAATGTTTTCCGAGCACCAGTATCATTGTGTCTGCCCCATGCGTAGTCCAGAAGACCCG
GACCGCATGATGAAATACGCCAGTAAACTGGCGGAAAAAGCGTGCAAGATTACAAACAAGAACTTGCA
TGAGAAGATTAAGGATCTCCGGGATCCCCTGAAAAGGCTGTTTAAGTTGGGTAAACCGCTCCCAGCCG
ACGACGAGCAAGACGAAGACAGAAGACGCGCTCTGCTAGATGAAACAAAGGCGTGGTTTAGAGTAGGT
ATAACAGGCACTTTAGCAGTGGCCGTGACGACCCGGTATGAGGTAGACAATATTACACCTGTCCTACT
GGCATTGAGAACTTTTGCCCAGAGCAAAAGAGCATTCCAAGCCATCAGAGGGGAAATAAAGCATCTCT
ACGGTGGTCCTAAATAGTCAGCATAGTACATTTCATCTGACTAATACTACAACACCACCACCATGAAT
AGAGGATTCTTTAACATGCTCGGCCGCCGCCCCTTCCCGGCCCCCACTGCCATGTGGAGGCCGCGGAG
AAGGAGGCAGGCGGCCCCGATGCCTGCCCGCAACGGGCTGGCTTCTCAAATCCAGCAACTGACCACAG
CCGTCAGTGCCCTAGTCATTGGACAGGCAACTAGACCTCAACCCCCACGTCCACGCCCGCCACCGCGC
CAGAAGAAGCAGGCGCCCAAGCAACCACCGAAGCCGAAGAAACCAAAAACGCAGGAGAAGAAGAAGAA
GCAACCTGCAAAACCCAAACCCGGAAAGAGACAGCGCATGGCACTTAAGTTGGAGGCCGACAGATTGT
TCGACGTCAAGAACGAAGACGGAGATGTCATCGGGCACGCACTGGCCATGGAAGGAAAGGTAATGAAA
CCTCTGCACGTGAAAGGAACCATCGACCACCCTGTGCTATCAAAGCTCAAATTTACCAAGTCGTCAGC
ATACGACATGGAGTTCGCACAGTTGCCAGTCAACATGAGAAGTGAGGCATTCACCTACACCAGTGAAC
ACCCCGAAGGATTCTATAACTGGCACCACGGAGCGGTGCAGTATAGTGGAGGTAGATTTACCATCCCT
CGCGGAGTAGGAGGCAGAGGAGACAGCGGTCGTCCGATCATGGATAACTCCGGTCGGGTTGTCGCGAT
AGTCCTCGGTGGCGCTGATGAAGGAACACGAACTGCCCTTTCGGTCGTCACCTGGAATAGTAAAGGGA
AGACAATTAAGACGACCCCGGAAGGGACAGAAGAGTGGTCCGCAGCACCACTGGTCACGGCAATGTGT
TTGCTCGGAAATGTGAGCTTCCCATGCGACCGCCCGCCCACATGCTATACCCGCGAACCTTCCAGAGC
CCTCGACATCCTTGAAGAGAACGTGAACCATGAGGCCTACGATACCCTGCTCAATGCCATATTGCGGT
GCGGATCGTCTGGCAGAAGCAAAAGAAGCGTCACTGACGACTTTACCCTGACCAGCCCCTACTTGGGC
ACATGCTCGTACTGCCACCATACTGAACCGTGCTTCAGCCCTGTTAAGATCGAGCAGGTCTGGGACGA
```

-continued

```
AGCGGACGATAACACCATACGCATACAGACTTCCGCCCAGTTTGGATACGACCATAGCGGAGCAGCAA

GCGCAAACAAGTACCGCTACATGTCGCTTAAGCAGGATCACACCGTTAAAGAAGGCACCATGGATGAC

ATCAAGATTAGCACCTCAGGACCGTGTAGAAGGCTTAGCTACAAAGGATACTTTCTCCTCGCAAAATG

CCCTCCAGGGGACAGCGTAACGGTTAGCATAGTGAGTAGCAACTCAGCAACGTCATGTACACTGGCCC

GCAAGATAAACCAAAATTCGTGGGACGGGAAAAATATGATCTACCTCCCGTTCACGGTAAAAAAATT

CCTTGCACAGTGTACGACCGTCTGAAAGAAACAACTGCAGGCTACATCACTATGCACAGGCCGGGACC

GCACGCTTATACATCCTACCTGGAAGAATCATCAGGGAAAGTTTACGCAAAGCCGCCATCTGGGAAGA

ACATTACGTATGAGTGCAAGTGCGGCGACTACAAGACCGGAACCGTTTCGACCCGCACCGAAATCACT

GGTTGCACCGCCATCAAGCAGTGCGTCGCCTATAAGAGCGACCAAACGAAGTGGGTCTTCAACTCACC

GGACTTGATCAGACATGACGACCACACGGCCCAAGGGAAATTGCATTTGCCTTTCAAGTTGATCCCGA

GTACCTGCATGGTCCCTGTTGCCCACGCGCCGAATGTAATACATGGCTTTAAACACATCAGCCTCCAA

TTAGATACAGACCACTTGACATTGCTCACCACCAGGAGACTAGGGGCAAACCCGGAACCAACCACTGA

ATGGATCGTCGGAAAGACGGTCAGAAACTTCACCGTCGACCGAGATGGCCTGGAATACATATGGGGAA

ATCATGAGCCAGTGAGGGTCTATGCCCAAGAGTCAGCACCAGGAGACCCTCACGGATGGCCACACGAA

ATAGTACAGCATTACTACCATCGCCATCCTGTGTACACCATCTTAGCCGTCGCATCAGCTACCGTGGC

GATGATGATTGGCGTAACTGTTGCAGTGTTATGTGCCTGTAAAGCGCGCCGTGAGTGCCTGACGCCAT

ACGCCCTGGCCCCAAACGCCGTAATCCCAACTTCGCTGGCACTCTTGTGCTGCGTTAGGTCGGCCAAT

GCTGAAACGTTCACCGAGACCATGAGTTACTTGTGGTCGAACAGTCAGCCGTTCTTCTGGGTCCAGTT

GTGCATACCTTTGGCCGCTTTCATCGTTCTAATGCGCTGCTGCTCCTGCTGCCTGCCTTTTTTAGTGG

TTGCCGGCGCCTACCTGGCGAAGGTAGACGCCTACGAACATGCGACCACTGTTCCAAATGTGCCACAG

ATACCGTATAAGGCACTTGTTGAAAGGGCAGGGTATGCCCCGCTCAATTTGGAGATCACTGTCATGTC

CTCGGAGGTTTTGCCTTCCACCAACCAAGAGTACATTACCTGCAAATTCACCACTGTGGTCCCCTCCC

CAAAAATCAAATGCTGCGGCTCCTTGGAATGTCAGCCGGCCGCTCATGCAGACTATACCTGCAAGGTC

TTCGGAGGGGTCTACCCCTTTATGTGGGGAGGAGCGCAATGTTTTTGCGACAGTGAGAACAGCCAGAT

GAGTGAGGCGTACGTCGAATTGTCAGCAGATTGCGCGTCTGACCACGCGCAGGCGATTAAGGTGCACA

CTGCCGCGATGAAAGTAGGACTGCGTATAGTGTACGGGAACACTACCAGTTTCCTAGATGTGTACGTG

AACGGAGTCACACCAGGAACGTCTAAAGACTTGAAAGTCATAGCTGGACCAATTTCAGCATCATTTAC

GCCATTCGATCATAAGGTCGTTATCCATCGCGGCCTGGTGTACAACTATGACTTCCCGGAATATGGAG

CGATGAAACCAGGAGCGTTTGGAGACATTCAAGCTACCTCCTTGACTAGCAAGGATCTCATCGCCAGC

ACAGACATTAGCTACTCAAGCCTTCCGCCAAGAATGTGCATGTCCCGTACACGCAGGCCGCATCAGGA

TTTGAGATGTGGAAAAACAACTCAGGCCGCCCATTGCAGGAAACCGCACCTTTCGGGTGTAAGATTGC

AGTAAATCCGCTCCGAGCGGTGGACTGTTCATACGGGAACATTCCCATTTCTATTGACATCCCGAACG

CTGCCTTTATCAGGACATCAGATGCACCACTGGTCTCAACAGTCAAATGTGAAGTCAGTGAGTGCACT

TATTCAGCAGACTTCGACGGGATGGCCACCCTGCAGTATGTATCCGACCGCGAAGGTCAATGCCCCGT

ACATTCGCATTCGAGCACAGCAACTCTCCAAGAGTCGACAGTACATGTCCTGGAGAAAGGAGCGGTGA

CAGTACACTTTAGCACCGCGAGTCCACAGGCGAACTTTATCGTATCGCTGTGTGGGAAGAAGACAACA

TGCAATGCAGAATGTAAACCACCAGCTGACCATATCGTGAGCACCCCGCACAAAAATGACCAAGAATT

TCAAGCCGCCATCTCAAAAACATCATGGAGTTGGCTGTTTGCCCTTTTCGGCGGCGCCTCGTCGCTAT

TAATTATAGGACTTATGATTTTTGCTTGCAGCATGATGCTGACTAGCACACGAAGATGACCGCTACGC

CCCAATGATCCGACCAGCAAAACTCGATGTACTTCCGAGGAACTGATGTGCATAATGCATCAGGCTCC

TACATTAGATCCCCGCTTACCGCGGGCAATATAGCAACACTAAAAACTCGATGTACTTCCGAGGAAGC
```

-continued

```
GCAGTgCATAATGCTGCGCaGTGTTGCCACATAACCACTATATTAACCATTTATCTAGCGGACGCCAA

AAACTCAATGTATTTCTGAGGAAGCGTGGTGCATAATGCCACGCAGCGTCTGCATAACTTTTATTATT

TCTTTTATTAATCAACAAAATTTTGTTTTAACATTTCAAAAAAAAAAAAAAAAAAAAAAAAAAAAAA

AAAAAAAGGGAATTCc
```

DISCUSSION

MAPseq is the first application of HTS to neuroanatomy and is a simple, rapid, and inexpensive approach to determining the projection patterns of myriad single neurons in one or more injection sites in a single animal. As a proof-of-principle, MAPseq was applied to the LC. In contrast to previous bulk labeling studies that reported diffuse and non-specific projections from the LC, this single neuron resolution analysis reveals that most individual LC neurons have a preferred cortical target, and reconciles a controversy about the specificity of LC projection patterns.

High-Throughput Sequencing and Neuro-Anatomy

The cost of sequencing the human genome was several billion dollars in 2003, but today is less than one thousand dollars—a decrease of over six orders of magnitude in just over a dozen years. This precipitous drop in sequencing costs continues unabated, at a rate faster even than Moore's law (the rate at which computers improve). Advances in high-throughput sequencing revolutionized disparate areas of biology (Reuter et al., 2015). DNA sequencing has evolved from a specialized tool for determining the sequences of genomes, into a technology for determining gene expression levels, discovering new species, tracking cell fates, and understanding cancer growth, among many other applications.

By recasting neuroanatomy, which is traditionally viewed as a problem of microscopy, as a problem of sequencing, MAPseq harnesses advances in high-throughput sequencing to permit efficient interrogation of the structure of brain circuits. MAPseq does not replace conventional approaches, but rather complements them. For example, MAPseq is ideally suited to the discovery of neuron classes defined by long-range projections. Also, because MAPseq is a sequencing-based method, it can readily be combined with other molecular approaches to examine the effects on long-range connections of manipulating single genes.

MAPseq Resolution

Determining projection patterns by MAPseq requires dissection of target areas. The spatial resolution with which the dissection is performed limits the precision with which projection maps can be resolved. In the one embodiment of the invention gross dissection is used, which affords only relatively crude spatial resolution, perhaps to the level of cortical areas (individual cortical areas were successfully dissected, including the primary auditory cortex; See FIG. 18). However, other methods including laser-capture microdissection (Espina et al., 2006), transcriptome in vivo analysis (TIVA) tagging (Lovatt et al., 2014), or fluorescent in situ sequencing (Lee et al., 2014) may be used to determine the location of barcodes in tissue.

The Controversy of LC Projections

The LC sends projections to most ipsilateral brain areas, with the notable exception of the striatum. However, how broadly individual neurons innervate those target areas is subject to debate. Classical retrograde tracing studies suggest a topographic organization of neocortical (Waterhouse et al., 1983) and brainwide (Loughlin et al., 1986) projection neurons in LC. Consistent with this, double retrograde labeling studies report that the LC projections to frontal and motor cortices (Chandler et al., 2014; Chandler and Waterhouse, 2012) overlap minimally. In contrast, other double retrograde studies find overlap between neurons projecting to separate structures along the same processing stream (Simpson et al., 1997), or structures as different as forebrain and cerebellum (Steindler, 1981). Very recent work based on retrograde viral tracing even concluded that LC neurons project nonspecifically throughout both cortex and the rest of the brain (Schwarz et al., 2015).

MAPseq single cell resolution data can reconcile these data. Using MAPseq, it was found that individual LC neurons have very specific projection targets in cortex and olfactory bulb, but are not limited to a single target. It was also observed that many LC neurons that project to cortex innervate a large fraction of it at some level, in addition to having preferred projection targets. It is this feature of single neuron projections that lead Schwarz et al. (Schwarz et al., 2015) to conclude that LC neurons nonspecifically project throughout cortex and the bulb, and indeed MAPseq can recreate their data by simulating retrograde tracing on our single cell dataset.

CONCLUSION

MAPseq, the first application of HTS to neuroanatomy, is a simple, rapid, and inexpensive approach to determining the projection patterns of myriad single neurons in one or more injection sites in a single animal. Application of MAPseq to LC revealed unexpected structure that could not have been resolved by previous methods lacking single neuron resolution. In principle, MAPseq can be expanded to the entire brain by infecting a large fraction of neurons in the brain and dissecting the entire brain in order to determine where each neuron is situated.

Notably, MAPseq can readily be applied to map any neurons, including those associated with the central nervous system or peripheral nervous system. For instance, to gain insight into the neurons in the motor cortex that project to the spinal cord, MAPseq can be performed simply by injecting the motor cortex and dissecting both the motor cortex and the spinal cord in order to determine the projections. Thus, in addition to mapping connections in the brain, MAPseq can also be utilized to identify and map brain-peripheral neural connections e.g., in the gut, simply by separately dissecting the labeled brain and the peripheral target of interest.

Furthermore, MAPseq may also be combined with shRNA or CRISPR libraries to determine functionality on the scale of individual neurons. Such an application may be used for screening of brain-wide wiring defects in models of human disease and screening of drugs that are meant to counteract said wiring defects in those diseases. Such diseases may include, for example, neurodegenerative diseases such as Parkinson's, Alzheimer's, etc.

MAPseq also lays the foundation for using sequencing to decipher local neuron-to-neuron connectivity (Zador et al., 2012). Using DNA sequencing technology, experimenters have gained unprecedented insight into the heterogeneity of cell populations at the single cell level (Navin et al., 2012). By leveraging this sequencing technology, MAPseq empowers neuroscience researchers to efficiently do the same for populations of neuronal projections examined at the single neuron level.

REFERENCES

Bredenbeek, P. J., Frolov, I., Rice, C. M. & Schlesinger, S. Sindbis virus expression vectors: packaging of RNA replicons by using defective helper RNAs. *Journal of Virology* 67, 6439-6446 (1993).

Cetin, A., Komai, S., Eliava, M., Seeburg, P. H. & Osten, P. Stereotaxic gene delivery in the rodent brain. *Nat Protoc* 1, 3166-3173 (2007).

Chandler, D. & Waterhouse, B. D. Evidence for Broad Versus Segregated Projections from Cholinergic and Noradrenergic Nuclei to Functionally and Anatomically Discrete Subregions of Prefrontal Cortex. *Front. Behav. Neurosci.* 6, (2012).

Chandler, D. J., Gao, W. J. & Waterhouse, B. D. Heterogeneous organization of the locus coeruleus projections to prefrontal and motor cortices. *Proceedings of the National Academy of Sciences* 111, 6816-6821 (2014).

Chen, Y. & Varani, G. Engineering RNA-binding proteins for biology. *FEBS J.* 280(16), 3734-3754 (2013).

Daigle, N. & Ellenberg, J. λN-GFP: an RNA reporter system for live-cell imaging. *Nat Meth* 4, 633-636 (2007).

Economo, M. N. et al. A platform for brain-wide imagining and reconstruction of individual neurons. *Elife* 5, 13 (2016).

Espina, V., Wulfkuhle, J. D., Calvert, V. S., VanMeter, A., Zhou, W., Coukos, G., Geho, D. H., Petricoin, E. F., and Liotta, L. A., Laser-capture microdissection. *Nature Protocols* 1, 586-603 (2006).

Fairless, R. et al. Polarized targeting of neurexins to synapses is regulated by their C-terminal sequences. *The Journal of Neuroscience* 28(48), 12969-12981 (2008).

Foote, S. L., Bloom, F. E. & Aston-Jones, G. Nucleus ceruleus: new evidence of anatomical and physiological specificity. *Physiol. Rev.* 63, 844-914 (1983).

Foote, S. L. & Morrison, J. H. Extrathalamic modulation of cortical function. *Annu. Rev. Neurosci.* (1987).

Furuta, T. et al. In vivo transduction of central neurons using recombinant Sindbis virus: Golgi-like labeling of dendrites and axons with membrane-targeted fluorescent proteins. *J. Histochem. Cytochem.* 49, 1497-1508 (2001).

Ghosh, S. et al. Sensory maps in the olfactory cortex defined by long-range viral tracing of single neurons. *Nature* 472, 217-220 (2011).

Glickfeld, L. L., Andermann, M. L., Bonin, V., and Reid, R. C. Cortico-cortical projections in mouse visual cortex are functionally target specific. *Nat Neurosci* 16, 219-226 (2013).

Herculano-Houzel, S., Mota, B. & Lent, R. Cellular scaling rules for rodent brains. *Proceedings of the National Academy of Sciences* 103, 12138-12143 (2006).

Kawamura, M. et al. *Characterization of novel bicistronic sindbis virus vectors, SinEGdsp and SinIRES-EG, in cultured neurons.* 105-120 (Recent Res. Dev. Neurochem., 2003). doi:10.1046/j.1471-4159.2003.01875.x/full Kebschull, J. M., da Silva, P. G. & Zador, A. M. A new Defective Helper RNA to produce Sindbis virus that infects neurons but does not propagate. *Biorxiv* 033738-16 (2015).

Kebschull, J. M. & Zador, A. M. Sources of PCR-induced distortions in high-throughput sequencing data sets. *Nucleic Acids Research* gkv717 (2015).

Kennedy, A., Asahina, K., Hoopfer, E., Inagaki, H., Jung, Y., Lee, H., Remedios, R., and Anderson, D. J. Internal States and Behavioral Decision-Making: Toward an Integration of Emotion and Cognition. *Cold Spring Harbor Symposia on Quantitative Biology* 79, 199-210 (2014).

Kim, J. et al. mGRASP enables mapping mammalian synaptic connectivity with light microscopy. *Nat Meth* 9, 96-102 (2011).

Larson, D. R. et al. Real-Time Observation of Transcription Initiation and Elongation on an Endogenous Yeast Gene. *Science* 332, 475-478 (2011).

Lee, J. H. et al. Highly multiplexed subcellular RNA sequencing in situ. *Science* 343, 1360-1363 (2014).

Livet, J. et al. Transgenic strategies for combinatorial expression of fluorescent proteins in the nervous system. *Nature* 450, 56-62 (2007).

Loughlin, S. E., Foote, S. L. & Bloom, F. E. Efferent projections of nucleus locus coeruleus: Topographic organization of cells of origin demonstrated by three-dimensional reconstruction. *Neuroscience* 18, 291-306 (1986).

Loughlin, S. E., Foote, S. L. & Fallon, J. H. Locus coeruleus projections to cortex: Topography, morphology and collateralization. *Brain Research Bulletin* 9, 287-294 (1982).

Lovatt, D. et al. Transcriptome in vivo analysis (TIVA) of spatially defined single cells in live tissue. *Nat Meth* 11, 190-196 (2014).

Mayer, C. et al. Clonally Related Forebrain Interneurons Disperse Broadly across Both Functional Areas and Structural Boundaries. *Neuron* 87, 989-998 (2015).

Morris, J., Singh, J. M. & Eberwine, J. H. Transcriptome Analysis of Single Cells. *JoVE (Journal of Visualized Experiments)* e2634-e2634 (2011). doi:10.3791/2634

Movshon, J. A., and Newsome, W. T. Visual response properties of striate cortical neurons projecting to area MT in macaque monkeys. *Journal of Neuroscience* 16, 7733-7741. (1996).

Navin, N. et al. Tumour evolution inferred by single-cell sequencing. *Nature* 472, 90-94 (2012).

Oh, S. W. et al. A mesoscale connectome of the mouse brain. *Nature* 508, 207-214 (2014).

Reuter, J. A., Spacek, D. V., and Snyder, M. P. High-throughput sequencing technologies. *Molecular Cell* 58, 586-597 (2015).

Room, P., Postema, F. & Korf, J. Divergent axon collaterals of rat locus coeruleus neurons: Demonstration by a fluorescent double labeling technique. *Brain Research* 221, 219-230 (1981).

Schüz, A. & Palm, G. Density of neurons and synapses in the cerebral cortex of the mouse. *J. Comp. Neurol.* 286, 442-455 (1989).

Schwarz, L. A. et al. Viral-genetic tracing of the input-output organization of a central noradrenaline circuit. *Nature* 524, 88-92 (2015).

Shipley, M. T., Halloran, F. J., and la Torre, de, J. Surprisingly rich projection from locus coeruleus to the olfactory bulb in the rat. *Brain Research* 329, 294-299 (1985).

Simpson, K. L., Altman, D. W., Wang, L., Kirifides, M. L., Lin, R. C., and Waterhouse, B. D. Lateralization and functional organization of the locus coeruleus projection to the trigeminal somatosensory pathway in rat. *J. Comp. Neurol.* 385, 135-147 (1997).

Steindler, D. A. Locus coeruleus neurons have axons that branch to the forebrain and cerebellum. *Brain Research* 223, 367-373 (1981).

Sternson, S. M. Hypothalamic survival circuits: blueprints for purposive behaviors. *Neuron* 77, 810-824 (2013).

Sugino, K. et al. Molecular taxonomy of major neuronal classes in the adult mouse forebrain. *Nat Neurosci* 9, 99-107 (2006).

Tasic, B., Menon, V., Nguyen, T. N., Kim, T. K., Jarsky, T., Yao, Z., Levi, B., Gray, L. T., Sorensen, S. A., Dolbeare, T., et al. Adult mouse cortical cell taxonomy revealed by single cell transcriptomics. *Nat Neurosci* 19, 335-346 (2016).

Walsh, C. & Cepko, C. L. Widespread dispersion of neuronal clones across functional regions of the cerebral cortex. *Science* 255, 434-440 (1992).

Waterhouse, B. D., Lin, C. S., Burne, R. A. & Woodward, D. J. The distribution of neocortical projection neurons in the locus coeruleus. *Journal of Comparative Neurology* 217, 418-431 (1983).

Zador, A. M. et al. Sequencing the connectome. *PLoS Biol* 10, e1001411 (2012).

Zingg, B. et al. Neural networks of the mouse neocortex. *Cell* 156, 1096-1111 (2014).

---

What is claimed is:

1. A composition comprising a plurality of labeled neurons, each of which contains
   (a) a barcoded nucleic acid which serves as a label; and
   (b) a chimeric protein containing
      (i) a nucleic acid binding domain that is specifically bound to the barcoded nucleic acid in the labeled neuron; and
      (ii) a synaptic trafficking signal sequence capable of directing transport of the barcoded nucleic acid to the axon terminals of the labeled neuron, wherein at least 50% of the plurality of labeled neurons are labeled with a unique barcoded nucleic acid, and wherein the barcoded nucleic acid contains a binding region that is specifically recognized by the nucleic acid-binding domain of the chimeric protein.

2. The composition of claim 1, wherein the binding region is a boxB motif or an MS-2 stem-loop motif.

3. The composition of claim 1, wherein the chimeric protein is a modified presynaptic protein.

4. The composition of claim 1, wherein the presynaptic protein is pre-mGRASP.

5. The composition of claim 1, wherein the nucleic acid-binding domain is an nλ domain or a portion of the MS-2 coat protein.

6. The composition of claim 1, wherein the chimeric protein further comprises a Myc epitope tag and/or a CLIP-tag domain.

7. The composition of claim 1, wherein the chimeric protein is MAPP-nλ or CLAP-1x-nλ.

8. The composition of claim 1, wherein the barcoded nucleic acid and chimeric protein are encoded by a modified Sindbus virus expression construct.

9. The composition of claim 8, wherein the modified Sindbus virus is produced using a defective helper RNA which produces virions that are and neurotropic propagation-incompetent.

10. The composition of claim 9, wherein the modified Sindbus virus is produced using the defective helper RNA DH-BB (5' SIN;TE12ORF).

11. The composition of claim 1, wherein the barcode in each of the barcoded nucleic acids has a length of (k) nucleotides, wherein $4^k$ is greater than the number of neurons to be labeled.

12. The composition of claim 1, wherein the barcoded nucleic acid contains a barcode region that is about 30 nucleotides in length.

13. The composition of claim 1, wherein the barcoded nucleic acid encodes a fluorescent marker.

14. The composition of claim 1, wherein the barcoded nucleic acid is RNA.

15. A method for obtaining a plurality of labeled neurons according to claim 1, comprising infecting neurons with a modified, barcoded Sindbus virus library.

16. The composition of claim 1, wherein at least 75% of the plurality of labeled neurons are labeled with a unique barcoded nucleic acid.

17. The composition of claim 1, wherein at least 95% of the plurality of labeled neurons are labeled with a unique barcoded nucleic acid.

* * * * *

SEQUENCE LISTING

```
<160> NUMBER OF SEQ ID NOS: 16

<210> SEQ ID NO 1
<211> LENGTH: 120
<212> TYPE: DNA
<213> ORGANISM: Artificial Sequence
<220> FEATURE:
<223> OTHER INFORMATION: Seqence used to create a diverse pool of double
      stranded ultramers
<220> FEATURE:
<221> NAME/KEY: misc_feature
<222> LOCATION: (71)..(100)
<223> OTHER INFORMATION: n is a, c, g, or t

<400> SEQUENCE: 1
aagtaaacgc gtaatgatac ggcgaccacc gagatctaca ctctttccct acacgacgct        60
cttccgatct nnnnnnnnnn nnnnnnnnnn nnnnnnnnnn yygtactgcg ccgctacct       120

<210> SEQ ID NO 2
<211> LENGTH: 200
<212> TYPE: DNA
<213> ORGANISM: artificial sequence
<220> FEATURE:
<223> OTHER INFORMATION: double stranded ultramer sequence used to
      produce spike-in RNA
<220> FEATURE:
<221> NAME/KEY: misc_feature
<222> LOCATION: (113)..(136)
<223> OTHER INFORMATION: n is a, c, g, or t

<400> SEQUENCE: 2
gtcatgatca taatacgact cactataggg gacgagctgt acaagtaaac gcgtaatgat        60
acggcgacca ccgagatcta cactctttcc ctacacgacg ctcttccgat ctnnnnnnnn       120
nnnnnnnnnn nnnnnnatca gtcatcggag cggccgctac ctaattgccg tcgtgaggta       180
cgaccaccgc tagctgtaca                                                   200

<210> SEQ ID NO 3
<211> LENGTH: 20
<212> TYPE: DNA
<213> ORGANISM: Artificial Sequence
<220> FEATURE:
<223> OTHER INFORMATION: qPCR primer for barcode DNA

<400> SEQUENCE: 3
gacgacggca actacaagac                                                    20

<210> SEQ ID NO 4
<211> LENGTH: 21
<212> TYPE: DNA
<213> ORGANISM: Artificial Sequence
<220> FEATURE:
<223> OTHER INFORMATION: qPCR primer for barcode DNA

<400> SEQUENCE: 4
```
tagttgtact ccagcttgtg c                                              21

<210> SEQ ID NO 5
<211> LENGTH: 24
<212> TYPE: DNA
<213> ORGANISM: Artificial Sequence
<220> FEATURE:
<223> OTHER INFORMATION: qPCR primer for beta-actin cDNA

<400> SEQUENCE: 5
cggttccgat gccctgaggc tctt                                           24

<210> SEQ ID NO 6
<211> LENGTH: 24
<212> TYPE: DNA
<213> ORGANISM: Artificial Sequence
<220> FEATURE:
<223> OTHER INFORMATION: qPCR primer for beta-actin cDNA

<400> SEQUENCE: 6
cgtcacactt catgatggaa ttga                                           24

<210> SEQ ID NO 7
<211> LENGTH: 58
<212> TYPE: DNA
<213> ORGANISM: Artificial Sequence
<220> FEATURE:
<223> OTHER INFORMATION: MapSeq Method ds-cDNA gene specific primer
<220> FEATURE:
<221> NAME/KEY: misc_feature
<222> LOCATION: (21)..(38)
<223> OTHER INFORMATION: n is a, c, g, or t

<400> SEQUENCE: 7
cttggcaccc gagaattcca nnnnnnnnnn nnnnnnnntg tacagctagc ggtggtcg     58

<210> SEQ ID NO 8
<211> LENGTH: 20
<212> TYPE: DNA
<213> ORGANISM: Artificial Sequence
<220> FEATURE:
<223> OTHER INFORMATION: MapSeq Method amplifying PCR primer

<400> SEQUENCE: 8
ctcggcatgg acgagctgta                                                20

<210> SEQ ID NO 9
<211> LENGTH: 63
<212> TYPE: DNA
<213> ORGANISM: Artificial Sequence
<220> FEATURE:
<223> OTHER INFORMATION: MapSeq Method amplifying PCR primer

<400> SEQUENCE: 9
caagcagaag acggcatacg agatcgtgat gtgactggag ttccttggca cccgagaatt   60
cca                                                                  63

<210> SEQ ID NO 10
<211> LENGTH: 20
<212> TYPE: DNA
<213> ORGANISM: Artificial Sequence
<220> FEATURE:
<223> OTHER INFORMATION: MapSeq Method amplifying PCR primer

<400> SEQUENCE: 10
aatgatacgg cgaccaccga                                              20

<210> SEQ ID NO 11
<211> LENGTH: 21
<212> TYPE: DNA
<213> ORGANISM: Artificial Sequence
<220> FEATURE:
<223> OTHER INFORMATION: MapSeq Method amplifying PCR primer

<400> SEQUENCE: 11
caagcagaag acggcatacg a                                            21

<210> SEQ ID NO 12
<211> LENGTH: 44
<212> TYPE: DNA
<213> ORGANISM: Artificial Sequence
<220> FEATURE:
<223> OTHER INFORMATION: qPCR primer
<220> FEATURE:
<221> NAME/KEY: misc_feature
<222> LOCATION: (22)..(22)
<223> OTHER INFORMATION: n is a, c, g, or t

<400> SEQUENCE: 12
aatgatacgg cgaccaccga andcaagcag aagacggcat acga                   44

<210> SEQ ID NO 13
<211> LENGTH: 21
<212> TYPE: DNA
<213> ORGANISM: Artificial Sequence
<220> FEATURE:
<223> OTHER INFORMATION: qPCR primer

<400> SEQUENCE: 13
caagcagaag acggcatacg a                                            21

<210> SEQ ID NO 14
<211> LENGTH: 736
<212> TYPE: PRT
<213> ORGANISM: Artificial Sequence
<220> FEATURE:
<223> OTHER INFORMATION: MAPP-nlamda protein

<400> SEQUENCE: 14

Met Pro Pro Ser Thr Ser Leu Leu Leu Ala Ala Leu Leu Pro Phe
1               5                   10                  15

Ala Leu Pro Ala Ser Asp Trp Lys Thr Gly Glu Val Thr Ala Ser Arg
            20                  25                  30

Asp His Met Val Leu His Glu Tyr Val Asn Ala Ala Gly Ile Thr Gly
        35                  40                  45

Gly Gly Gly Ser Gly Gly Gly Gly Ser Val Asp Glu Gln Lys Leu Ile
    50                  55                  60

Ser Glu Glu Asp Leu Gln Phe Met Asp Lys Asp Cys Glu Met Lys Arg
65                  70                  75                  80

Thr Thr Leu Asp Ser Pro Leu Gly Lys Leu Glu Leu Ser Gly Cys Glu
                85                  90                  95

Gln Gly Leu His Arg Ile Ile Phe Leu Gly Lys Gly Thr Ser Ala Ala
            100                 105                 110

Asp Ala Val Glu Val Pro Ala Pro Ala Ala Val Leu Gly Gly Pro Glu
        115                 120                 125

Pro Leu Ile Gln Ala Thr Ala Trp Leu Asn Ala Tyr Phe His Gln Pro
    130                 135                 140

-continued

```
Glu Ala Ile Glu Glu Phe Pro Val Pro Ala Leu His His Pro Val Phe
145                 150                 155                 160
Gln Gln Glu Ser Phe Thr Arg Gln Val Leu Trp Lys Leu Leu Lys Val
                165                 170                 175
Val Lys Phe Gly Glu Val Ile Ser Glu Ser His Leu Ala Ala Leu Val
            180                 185                 190
Gly Asn Pro Ala Ala Thr Ala Ala Val Asn Thr Ala Leu Asp Gly Asn
        195                 200                 205
Pro Val Pro Ile Leu Ile Pro Cys His Arg Val Val Gln Gly Asp Ser
210                 215                 220
Asp Val Gly Pro Tyr Leu Gly Gly Leu Ala Val Lys Glu Trp Leu Leu
225                 230                 235                 240
Ala His Glu Gly His Arg Leu Gly Lys Pro Gly Leu Gly Gly Gly
                245                 250                 255
Gly Ser Val Asp Phe Gln Lys Ala Ser Ser Ile Val Tyr Lys Lys Glu
                260                 265                 270
Gly Glu Gln Val Glu Phe Ser Phe Pro Leu Ala Phe Thr Val Glu Lys
                275                 280                 285
Leu Thr Gly Ser Gly Glu Leu Trp Trp Gln Ala Glu Arg Ala Ser Ser
290                 295                 300
Ser Lys Ser Trp Ile Thr Phe Asp Leu Lys Asn Lys Glu Val Ser Val
305                 310                 315                 320
Lys Arg Val Thr Gln Asp Pro Lys Leu Gln Met Gly Lys Lys Leu Pro
                325                 330                 335
Leu His Leu Thr Leu Pro Gln Ala Leu Pro Gln Tyr Ala Gly Ser Gly
                340                 345                 350
Asn Leu Thr Leu Ala Leu Glu Ala Lys Thr Gly Lys Leu His Gln Glu
                355                 360                 365
Val Asn Leu Val Val Met Arg Ala Thr Gln Leu Gln Lys Asn Leu Thr
                370                 375                 380
Cys Glu Val Trp Gly Pro Thr Ser Pro Lys Leu Met Leu Ser Leu Lys
385                 390                 395                 400
Leu Glu Asn Lys Glu Ala Lys Val Ser Lys Arg Glu Lys Ala Val Trp
                405                 410                 415
Val Leu Asn Pro Glu Ala Gly Met Trp Gln Cys Leu Leu Ser Asp Ser
                420                 425                 430
Gly Gln Val Leu Leu Glu Ser Asn Ile Lys Val Leu Pro Thr Trp Ser
                435                 440                 445
Thr Pro Val Gln Pro Met Ala Leu Ile Val Leu Gly Gly Val Ala Gly
            450                 455                 460
Leu Leu Leu Phe Ile Gly Leu Gly Ile Phe Phe Cys Val Arg Tyr Lys
465                 470                 475                 480
Tyr Arg Asn Arg Asp Glu Gly Ser Ser Ala Pro Pro Leu Asp Gly Ala
                485                 490                 495
Gly Ala Gly Ala Gly Ala Gly Ala Gly Gly Leu Ala Thr Met
            500                 505                 510
Asp Ala Gln Thr Arg Arg Glu Arg Arg Ala Glu Lys Gln Ala Gln
                515                 520                 525
Trp Lys Ala Ala Asn Pro Pro Leu Asp Gly Ala Gly Ala Gly Ala Gly
            530                 535                 540
Ala Gly Ala Gly Ala Gly Gly Leu Ala Thr Met Asp Ala Gln Thr Arg
545                 550                 555                 560
Arg Arg Glu Arg Arg Ala Glu Lys Gln Ala Gln Trp Lys Ala Ala Asn
```

```
                    565                 570                 575
Pro Pro Leu Asp Gly Ala Gly Ala Gly Ala Gly Ala
            580                 585                 590

Gly Gly Leu Ala Thr Met Asp Ala Gln Thr Arg Arg Glu Arg Arg
            595                 600                 605

Ala Glu Lys Gln Ala Gln Trp Lys Ala Ala Asn Pro Pro Leu Asp Gly
            610                 615                 620

Ala Gly Ala Gly Ala Gly Ala Gly Ala Gly Gly Leu Ala Thr
625                 630                 635                 640

Met Asp Ala Gln Thr Arg Arg Glu Arg Arg Ala Glu Lys Gln Ala
                    645                 650                 655

Gln Trp Lys Ala Ala Asn Pro Pro Leu Glu Pro Pro Leu Asp Gly Ala
                    660                 665                 670

Gly Ala Gly Ala Gly Ala Gly Ala Gly Gly Leu Ala Thr Pro
            675                 680                 685

Pro Ser Ala Tyr His Val Asp Glu Ser Arg Asn Tyr Ile Ser Asn Ser
            690                 695                 700

Ala Gln Ser Asn Gly Ala Val Val Lys Glu Lys Gln Pro Ser Ser Ala
705                 710                 715                 720

Lys Ser Ala Asn Lys Asn Lys Lys Asn Lys Asp Lys Glu Tyr Tyr Val
                    725                 730                 735

<210> SEQ ID NO 15
<211> LENGTH: 710
<212> TYPE: PRT
<213> ORGANISM: Artificial Sequence
<220> FEATURE:
<223> OTHER INFORMATION: CLAP-1x-nlamda protein

<400> SEQUENCE: 15

Met Tyr Gln Arg Met Leu Arg Cys Gly Ala Asp Leu Gly Ser Pro Gly
1               5                   10                  15

Gly Gly Ser Gly Gly Ala Gly Gly Arg Leu Ala Leu Ile Trp Ile
            20                  25                  30

Val Pro Leu Thr Leu Gly Gly Leu Leu Gly Val Ala Trp Gly Glu Phe
            35                  40                  45

Glu Gln Lys Leu Ile Ser Glu Glu Asp Leu Gln Phe Met Asp Lys Asp
        50                  55                  60

Cys Glu Met Lys Arg Thr Thr Leu Asp Ser Pro Leu Gly Lys Leu Glu
65                  70                  75                  80

Leu Ser Gly Cys Glu Gln Gly Leu His Arg Ile Ile Phe Leu Gly Lys
                85                  90                  95

Gly Thr Ser Ala Ala Asp Ala Val Glu Val Pro Ala Pro Ala Ala Val
            100                 105                 110

Leu Gly Gly Pro Glu Pro Leu Ile Gln Ala Thr Ala Trp Leu Asn Ala
            115                 120                 125

Tyr Phe His Gln Pro Glu Ala Ile Glu Glu Phe Pro Val Pro Ala Leu
        130                 135                 140

His His Pro Val Phe Gln Gln Glu Ser Phe Thr Arg Gln Val Leu Trp
145                 150                 155                 160

Lys Leu Leu Lys Val Val Lys Phe Gly Glu Val Ile Ser Glu Ser His
                165                 170                 175

Leu Ala Ala Leu Val Gly Asn Pro Ala Ala Thr Ala Ala Val Asn Thr
            180                 185                 190

Ala Leu Asp Gly Asn Pro Val Pro Ile Leu Ile Pro Cys His Arg Val
```

```
            195                 200                 205
Val Gln Gly Asp Ser Val Gly Pro Tyr Leu Gly Leu Ala Val
210                 215                 220

Lys Glu Trp Leu Leu Ala His Glu Gly His Arg Leu Gly Lys Pro Gly
225                 230                 235                 240

Leu Gly Val Asp Gly Thr Ala Ser Ser Leu Gly Ala His His Ile His
                    245                 250                 255

His Phe His Gly Ser Ser Lys His His Ser Val Pro Ile Ala Ile Tyr
                260                 265                 270

Arg Ser Pro Ala Ser Leu Arg Gly Gly His Ala Gly Thr Thr Tyr Ile
                275                 280                 285

Phe Ser Lys Gly Gly Gly Gln Ile Thr Tyr Lys Trp Pro Pro Asn Asp
                290                 295                 300

Arg Pro Ser Thr Arg Ala Asp Arg Leu Ala Ile Gly Phe Ser Thr Val
305                 310                 315                 320

Gln Lys Glu Ala Val Leu Val Arg Val Asp Ser Ser Ser Gly Leu Gly
                325                 330                 335

Asp Tyr Leu Glu Leu His Ile His Gln Gly Lys Ile Gly Val Lys Phe
                340                 345                 350

Asn Val Gly Thr Asp Asp Ile Ala Ile Glu Glu Ser Asn Ala Ile Ile
                355                 360                 365

Asn Asp Gly Lys Tyr His Val Val Arg Phe Thr Arg Ser Gly Gly Asn
370                 375                 380

Ala Thr Leu Gln Val Asp Ser Trp Pro Val Ile Glu Arg Tyr Pro Ala
385                 390                 395                 400

Gly Arg Gln Leu Thr Ile Phe Asn Ser Gln Ala Thr Ile Ile Ile Gly
                405                 410                 415

Gly Lys Glu Gln Gly Gln Pro Phe Gln Gly Gln Leu Ser Gly Leu Tyr
                420                 425                 430

Tyr Asn Gly Leu Lys Val Leu Asn Met Ala Ala Glu Asn Asp Ala Asn
                435                 440                 445

Ile Ala Ile Val Gly Asn Val Arg Leu Val Gly Glu Val Pro Ser Ser
                450                 455                 460

Met Thr Thr Glu Ser Thr Ala Thr Ala Met Gln Ser Glu Met Ser Thr
465                 470                 475                 480

Ser Ile Met Glu Thr Thr Thr Thr Leu Ala Thr Ser Thr Ala Arg Arg
                485                 490                 495

Gly Lys Pro Pro Thr Lys Glu Pro Ile Ser Gln Thr Thr Asp Asp Ile
                500                 505                 510

Leu Val Ala Ser Ala Glu Cys Pro Ser Asp Glu Asp Ile Asp Pro
                515                 520                 525

Cys Glu Pro Ser Ser Gly Gly Leu Ala Asn Pro Thr Arg Val Gly Gly
                530                 535                 540

Arg Glu Pro Tyr Pro Gly Ser Ala Glu Val Ile Arg Glu Ser Ser Ser
545                 550                 555                 560

Thr Thr Gly Met Val Val Gly Ile Val Ala Ala Ala Leu Cys Ile
                565                 570                 575

Leu Ile Leu Leu Tyr Ala Met Tyr Lys Tyr Arg Asn Arg Asp Glu Gly
                580                 585                 590

Ser Ser Ala Pro Pro Leu Asp Gly Ala Gly Ala Gly Ala Gly
                595                 600                 605

Ala Gly Ala Gly Gly Leu Ala Thr Met Asp Ala Gln Thr Arg Arg Arg
610                 615                 620
```

```
Glu Arg Arg Ala Glu Lys Gln Ala Gln Trp Lys Ala Ala Asn Leu Glu
625                 630                 635                 640

Pro Pro Leu Asp Gly Ala Gly Ala Gly Ala Gly Ala Gly Ala
            645                 650                 655

Gly Gly Leu Ala Thr Pro Pro Ser Ala Tyr His Val Asp Ser Arg
            660                 665                 670

Asn Tyr Ile Ser Asn Ser Ala Gln Ser Asn Gly Ala Val Val Lys Glu
        675                 680                 685

Met Gln Pro Ser Ser Ala Lys Ser Ala Asn Lys Asn Lys Lys Asn Lys
690                 695                 700

Asp Lys Glu Tyr Tyr Val
705                 710

<210> SEQ ID NO 16
<211> LENGTH: 4844
<212> TYPE: DNA
<213> ORGANISM: Artificial Sequence
<220> FEATURE:
<223> OTHER INFORMATION: Defective helper RNA DH-BB(5'SIN;TE12ORF) used
      to produce modified Sindbus virus

<400> SEQUENCE: 16
tatagattga cggcgtagta cacactattg aatcaaacag ccgaccaatt gcactaccat        60
cacaatggag aagccagtag taaacgtaga cgtagacccc cagagtccgt ttgtcgtgca       120
actgcaaaaa agcttcccgc aatttgaggt agtagcacag caggtcactc caaatgacca       180
tgctaatgcc agagcatttt cgcatctggc cagtaaaacta atcgagctgg aggttcctac       240
cacagcgacg atcttggaca taggcagcgc accggctcgt agaatgtttt ccgagcacca       300
gtatcattgt gtctgcccca tgcgtagtcc agaagacccg accgcatga tgaaatacgc        360 cagtaaactg gcggaaaaag cgtgcaagat tacaaacaag aacttgcatg aagagattaa       420
ggatctccgg gatcccctga aaaggctgtt taagttgggt aaaccgctcc cagccgacga       480
cgagcaagac gaagacagaa gacgcgctct gctagatgaa acaaaggcgt ggtttagagt       540
aggtataaca ggcactttag cagtggccgt gacgacccgg tatgaggtag acaatattac       600
acctgtccta ctggcattga gaacttttgc ccagagcaaa agagcattcc aagccatcag       660
agggaaaata aagcatctct acggtggtcc taaaatagtca gcatagtaca tttcatctga       720
ctaatactac aacaccacca ccatgaatag aggattcttt aacatgctcg ccgccgccc        780 cttcccggcc cccactgcca tgtggaggcc gcggagaagg aggcaggcgg ccccgatgcc       840
tgcccgcaac gggctggctt ctcaaatcca gcaactgacc acagccgtca gtgccctagt       900
cattggacag gcaactagac ctcaaccccc acgtccacgc ccgccaccgc gccagaagaa       960
gcaggcgccc aagcaaccac cgaagccgaa gaaaccaaaa acgcaggaga agaagaagaa      1020
gcaacctgca aaacccaaac ccggaaagag acagcgcatg gcacttaagt tggaggccga      1080
cagattgttc gacgtcaaga cgaagacgg agatgtcatc gggcacgcac tggccatgga       1140
aggaaaggta atgaaacctc tgcacgtgaa aggaaccatc gaccaccctg tgctatcaaa      1200
gctcaaattt accaagtcgt cagcatacga catggagttc gcacagttgc cagtcaacat      1260
gagaagtgag gcattcacct acaccagtga acacccgaa ggattctata ctggcacca        1320 cggagcggtg cagtatagtg gaggtagatt taccatccct cgcggagtag gaggcagagg      1380
agacagcggt cgtccgatca tggataactc cggtcgggtt gtcgcgatag tcctcggtgg      1440
cgctgatgaa ggaacacgaa ctgcccttt ggtcgtcacc tggaatagta aagggaagac       1500
```

-continued

```
aattaagacg accccggaag ggacagaaga gtggtccgca gcaccactgg tcacggcaat    1560
gtgtttgctc ggaaatgtga gcttcccatg cgaccgcccg cccacatgct atacccgcga    1620
accttccaga gccctcgaca tccttgaaga gaacgtgaac catgaggcct acgatacccct   1680 gctcaatgcc atattgcggt gcggatcgtc tggcagaagc aaaagaagcg tcactgacga    1740
cttacccctg accagcccct acttgggcac atgctcgtac tgccaccata ctgaaccgtg    1800 cttcagcct gttaagatcg agcaggtctg ggacgaagcg gacgataaca ccatacgcat     1860
acagacttcc gcccagtttg gatacgacca tagcggagca gcaagcgcaa acaagtaccg    1920
ctacatgtcg cttaagcagg atcacaccgt taaagaaggc accatggatg acatcaagat    1980
tagcacctca ggaccgtgta gaaggcttag ctacaaagga tactttctcc tcgcaaaatg    2040
ccctccaggg gacagcgtaa cggttagcat agtgagtagc aactcagcaa cgtcatgtac    2100
actggcccgc aagataaaac caaaattcgt gggacgggaa aaatatgatc tacctcccgt    2160
tcacggtaaa aaaattcctt gcacagtgta cgaccgtctg aaagaaacaa ctgcaggcta    2220
catcactatg cacaggccgg gaccgcacgc ttatacatcc tacctggaag aatcatcagg    2280
gaaagtttac gcaaagccgc catctgggaa gaacattacg tatgagtgca agtgcggcga    2340
ctacaagacc ggaaccgttt cgacccgcac cgaaatcact ggttgcaccg ccatcaagca    2400
gtgcgtcgcc tataagagcg accaaacgaa gtgggtcttc aactcaccgg acttgatcag    2460
acatgacgac cacacggccc aagggaaatt gcatttgcct ttcaagttga tcccgagtac    2520
ctgcatggtc cctgttgccc acgcgccgaa tgtaatacat ggctttaaac acatcagcct    2580
ccaattagat acagaccact tgacattgct caccaccagg agactagggg caaacccgga    2640
accaaccact gaatggatcg tcggaaagac ggtcagaaac ttcaccgtcg accgagatgg    2700
cctggaatac atatggggaa atcatgagcc agtgagggtc tatgcccaag agtcagcacc    2760
aggagaccct cacggatggc cacacgaaat agtacagcat tactaccatc gccatcctgt    2820
gtacaccatc ttagccgtcg catcagctac cgtggcgatg atgattggcg taactgttgc    2880
agtgttatgt gcctgtaaag cgcgccgtga gtgcctgacg ccatacgccc tggccccaaa    2940
cgccgtaatc ccaacttcgc tggcactctt gtgctgcgtt aggtcggcca atgctgaaac    3000
gttcaccgag accatgagtt acttgtggtc gaacagtcag ccgttcttct gggtccagtt    3060
gtgcatacct ttggccgctt tcatcgttct aatgcgctgc tgctcctgct gcctgccttt    3120
tttagtggtt gccggcgcct acctggcgaa ggtagacgcc tacgaacatg cgaccactgt    3180
tccaaatgtg ccacagatac cgtataaggc acttgttgaa agggcagggt atgccccgct    3240
caatttggag atcactgtca tgtcctcgga ggttttgcct tccaccaacc aagagtacat    3300
tacctgcaaa ttcaccactg tggtcccctc cccaaaaatc aaatgctgcg gctccttgga    3360
atgtcagccg gccgctcatg cagactatac ctgcaaggtc ttcggagggg tctacccctt    3420
tatgtgggga ggagcgcaat gttttttgcga cagtgagaac agccagatga gtgaggcgta    3480
cgtcgaattg tcagcagatt gcgcgtctga ccacgcgcag gcgattaagg tgcacactgc    3540
cgcgatgaaa gtaggactgc gtatagtgta cgggaacact accagtttcc tagatgtgta    3600
cgtgaacgga gtcacaccag gaacgtctaa agacttgaaa gtcatagctg gaccaatttc    3660
agcatcattt acgccattcg atcataaggt cgttatccat cgcggcctgg tgtacaacta    3720
tgacttcccg gaatatggag cgatgaaacc aggagcgttt ggagacattc aagctacctc    3780
cttgactagc aaggatctca tcgccagcac agacattagc tactcaagcc ttccgccaag    3840
```

```
aatgtgcatg tcccgtacac gcaggccgca tcaggatttg agatgtggaa aaacaactca    3900
ggccgcccat tgcaggaaac cgcaccttttc gggtgtaaga ttgcagtaaa tccgctccga    3960
gcggtggact gttcatacgg gaacattccc atttctattg acatcccgaa cgctgccttt    4020
atcaggacat cagatgcacc actggtctca acagtcaaat gtgaagtcag tgagtgcact    4080
tattcagcag acttcgacgg gatggccacc ctgcagtatg tatccgaccg cgaaggtcaa    4140
tgccccgtac attcgcattc gagcacagca actctccaag agtcgacagt acatgtcctg    4200
gagaaaggag cggtgacagt acactttagc accgcgagtc cacaggcgaa ctttatcgta    4260
tcgctgtgtg ggaagaagac aacatgcaat gcagaatgta aaccaccagc tgaccatatc    4320
gtgagcaccc cgcacaaaaa tgaccaagaa tttcaagccg ccatctcaaa aacatcatgg    4380
agttggctgt ttgcccttttt cggcggcgcc tcgtcgctat taattatagg acttatgatt    4440
tttgcttgca gcatgatgct gactagcaca cgaagatgac cgctacgccc caatgatccg    4500
accagcaaaa ctcgatgtac ttccgaggaa ctgatgtgca taatgcatca ggctggtaca    4560
ttagatcccc gcttaccgcg ggcaatatag caacactaaa aactcgatgt acttccgagg    4620
aagcgcagtg cataatgctg cgcagtgttg ccacataacc actatattaa ccatttatct    4680
agcggacgcc aaaaactcaa tgtatttctg aggaagcgtg gtgcataatg ccacgcagcg    4740
tctgcataac ttttattatt tctttttatta atcaacaaaa ttttgttttt aacatttcaa    4800
aaaaaaaaaa aaaaaaaaaa aaaaaaaaaa aaaagggaa ttcc                      4844
```